US010088419B2

(12) United States Patent
Tajima et al.

(10) Patent No.: US 10,088,419 B2
(45) Date of Patent: Oct. 2, 2018

(54) LIGHT MEASUREMENT APPARATUS FOR REACTION VESSEL AND LIGHT MEASUREMENT METHOD

(71) Applicant: Universal Bio Research Co., Ltd., Matsudo-shi, Chiba (JP)

(72) Inventors: Hideji Tajima, Matsudo (JP); Takaki Sugimoto, Matsuda (JP); Yu Matsukubo, Matsudo (JP); Shuuichi Kobayashi, Matsudo (JP); Tetsuya Ueda, Matsudo (JP)

(73) Assignee: UNIVERSAL BIO RESEARCH CO., LTD., Matsudo-Shi, Chiba (JP)

( * ) Notice: Subject to any disclaimer, the term of this patent is extended or adjusted under 35 U.S.C. 154(b) by 36 days.

(21) Appl. No.: 15/388,602

(22) Filed: Dec. 22, 2016

(65) Prior Publication Data
US 2017/0160196 A1    Jun. 8, 2017

Related U.S. Application Data

(63) Continuation of application No. 14/415,072, filed as application No. PCT/JP2013/069385 on Jul. 17, 2013, now Pat. No. 9,556,477.

(30) Foreign Application Priority Data

Jul. 17, 2012 (JP) ................................. 2012-159088

(51) Int. Cl.
*G01N 21/00* (2006.01)
*G01N 21/64* (2006.01)
(Continued)

(52) U.S. Cl.
CPC ....... *G01N 21/645* (2013.01); *G01N 21/6428* (2013.01); *G01N 35/0098* (2013.01);
(Continued)

(58) Field of Classification Search
CPC ......... B01L 2300/0654; B01L 3/50825; C12Q 1/686; G01N 2021/6439;
(Continued)

(56) References Cited

U.S. PATENT DOCUMENTS 6,359,284 B1    3/2002   Hayashi et al.
7,148,043 B2   12/2006   Kordunsky et al.
(Continued)

FOREIGN PATENT DOCUMENTS

EP    1548481 A1   6/2005
EP    1803805 A1   7/2007
(Continued)

OTHER PUBLICATIONS

International Search Report for PCT/JP2013/069385 by ISA/JP, and English translation, dated Oct. 29, 2013.
(Continued)

*Primary Examiner* — Tri T Ton
(74) *Attorney, Agent, or Firm* — Haynes and Boone, LLP

(57) ABSTRACT

The invention relates to a method and apparatus for measuring the optical state on the inside of a reaction vessel. The apparatus includes: linking portions that optically connect with the interior of the reaction vessel that is linkable with reaction vessels, a connecting end arranging body having an arranging surface that arranges and supports along a predetermined path, connecting ends to which is provided back ends of the light guide portions, the front ends thereof being provided to the linking portions, the connecting ends being provided to the linking portions; a measurement device having measuring ends that are successively optically connectable with the connecting ends, and in which light based on the optical state is receivable by optical connections between the connecting ends and the measuring ends; and a light guide switching mechanism that successively optically connects the connecting ends and the measuring ends.

14 Claims, 40 Drawing Sheets

(51) Int. Cl.
*G01N 35/00* (2006.01)
*G01N 35/10* (2006.01)

(52) U.S. Cl.
CPC ... *G01N 35/00722* (2013.01); *G01N 35/1002* (2013.01); *G01N 35/1083* (2013.01); *G01N 2021/6417* (2013.01); *G01N 2021/6463* (2013.01); *G01N 2021/6482* (2013.01); *G01N 2021/6484* (2013.01); *G01N 2035/103* (2013.01); *G01N 2201/08* (2013.01)

(58) Field of Classification Search
CPC ... G01N 2021/6482; G01N 2021/6484; G01N 2035/103; G01N 21/6428; G01N 21/645; G01N 21/78; G01N 35/0098; G01N 35/10
USPC .............................. 356/432–444, 243.2–246
See application file for complete search history.

(56) References Cited

U.S. PATENT DOCUMENTS

| | | |
|---|---|---|
| 7,749,736 B2 | 7/2010 | Kordunsky et al. |
| 2010/0137165 A1 | 6/2010 | Tajima |
| 2012/0085933 A1 | 4/2012 | Doi et al. |
| 2012/0190034 A1 | 7/2012 | Tajima |
| 2012/0221252 A1 | 8/2012 | Heinz et al. |
| 2012/0295249 A1 | 11/2012 | Cherubini et al. |

FOREIGN PATENT DOCUMENTS

| | | |
|---|---|---|
| EP | 1845367 A1 | 10/2007 |
| EP | 1962084 A1 | 8/2008 |
| EP | 2463643 A1 | 6/2012 |
| JP | 62-106347 | 5/1987 |
| JP | 2002-10777 | 1/2002 |
| WO | WO 96/29602 | 9/1996 |
| WO | WO 2010/110096 | 9/2010 |
| WO | WO 2012/105712 | 8/2012 |
| WO | WO 2012/157685 | 11/2012 |

OTHER PUBLICATIONS

International Preliminary Report on Patentability Chapter II for PCT/JP2013/069385 by IPEA/JP, and English translation, dated Nov. 11, 2014.

Supplementary European Search Report, issued from the European Patent Office regarding European Application No. EP13819199, dated Feb. 5, 2016, 1 page.

Non-Final Rejection dated May 19, 2016 in U.S. Appl. No. 14/415,072, USPTO (10 pages).

Notice of Allowance dated Sep. 21, 2016 in U.S. Appl. No. 14/415,072, USPTO (7 pages).

(4)

LIGHT MEASUREMENT APPARATUS FOR REACTION VESSEL AND LIGHT MEASUREMENT METHOD

CROSS REFERENCE

This application is a continuation of U.S. patent application Ser. No. 14/415,072, which is a United States national phase application of co-pending international patent application number PCT/JP2013/069385, filed Jul. 17, 2013, which claims priority to Japanese patent application number 2012-159088, filed Jul. 17, 2012, the entire disclosures of which are hereby incorporated herein by reference.

TECHNICAL FIELD

The present invention relates to a light measurement apparatus for a reaction vessel, and a light measurement method therefor.

BACKGROUND ART

At the time reactions such as amplification of nucleic acids (DNA, RNA, and the like) and the fragments thereof (oligonucleotides, nucleotides, and the like) are performed, in tests that require quantitativeness, such as the analysis of gene expression levels, it becomes necessary to perform the amplification such that the ratio of the relative amounts of the respective nucleic acids can be known. Consequently, by using the real-time PCR method, and by using an apparatus provided with a thermal cycler and a fluorescence spectrophotometer, analysis by electrophoresis is made unnecessary as a result of the generation process of the DNA amplification products in PCR being detected and analyzed in real time. Furthermore, as a DNA amplification method that performs amplification while maintaining the quantitativeness with respect to the ratio of the relative amounts of the DNA or RNA contained in the sample before amplification, the SPIA (Single Primer Isothermal Amplification) method is used. In the SPIA method, the linear DNA amplification method resulting from an isothermal reaction utilizing DNA/RNA chimera primer, DNA polymerase, and RNaseH has become used.

In a case where processing such as nucleic acid amplification, and measurements thereof are performed, conventionally, the target nucleic acid is separated and extracted from the sample by using a filter by means of a manual method, by using magnetic particles and adsorption on an inner wall of a vessel or a pipette tip by means of a magnetic field, or by using a centrifuge. The separated and extracted target compound is transferred and introduced into a reaction vessel together with a reaction solution by a manual method and the like, and upon sealing of the reaction vessel using a manual method and the like, at the time reactions are performed using a temperature control device for reactions, optical measurements are performed with respect to the reaction vessel using a light measuring device (Patent Document 1).

In a case where the processing is executed by a manual method, a large burden is forced on the user. Furthermore, in a case where the processing is executed by combining a dispenser, a centrifuge, a magnetic force device, a temperature controller, a device for sealing the reaction vessel, a light measurement device, and the like, there is a concern of the scale of the utilized devices increasing and of the work area expanding. In particular, in a case where a plurality of samples is handled, since it becomes necessary to separate and extract a plurality of target nucleic acids and for amplification to be to respectively performed, the labor thereof becomes even greater, and furthermore, there is a concern of the work area also expanding further.

Specifically, in a case where reactions of the nucleic acids (DNA, RNA, and the like) to be amplified, and the like, are performed within a plurality of reaction vessels and these reactions are monitored by optical measurements, the measurements are performed by successively moving a single measuring device to the respective reaction vessels by a manual method, or the measurements are performed by providing a measuring device to each of the respective reaction vessels beforehand.

In the former case where a single measuring device is used, when the measuring device is attempted to be manually moved to the apertures of the reaction vessels, there is a concern of subtle differences occurring in the measurement conditions for each reaction vessel as a result of subtle displacements or relative motions between the reaction vessel and the measuring device.

In the latter case where a measuring device is provided to each of the respective reaction vessels, although the positioning accuracy becomes high, there is a concern of the devices scale expanding, and of the manufacturing costs increasing. Furthermore, although it is preferable to seal the apertures of the reaction vessels at the time of temperature control and the measurements, it is time-consuming to perform sealing, or opening and closing, with respect to a plurality of reaction vessels by a manual method with a lid, and in particular, there is a concern of the lid becoming adhered to the vessel apertures such that it becomes difficult to easily open the lid, and of contamination occurring from the liquid attached to the inside of the lid dripping or splashing. Furthermore, there is a concern of providing a dedicated opening and closing mechanism of the lid, complicating the apparatus, and increasing the manufacturing costs (Patent Document 2).

As a device that automatically performs measurements without providing a measurement device for each of the respective reaction vessels, there is an device that, at the time temperature control of a microplate having a plurality of wells is performed by a thermal cycler, successive light measurements of the respective wells is performed by moving a detection module over the microplate (Patent Documents 3 and 4).

In this device, since the detection module itself is moved in a state in which it is supported by the thermal cycler, a load that accompanies the acceleration from the movement is imparted on the detection module, which has precision optical system elements and electronic circuits such as a photomultiplier tube, thus becoming the cause of noise or breakdowns of the measurement device, and furthermore, there is a concern of the device lifetime being shortened.

Moreover, since the detection module is supported by the microplate, or is supported by a lid body sealing the respective wells of the microplate and only moves in a horizontal direction, a fixed spacing between the respective wells and the measuring end of the measurement device is necessary. Therefore, since attenuation from the scattering of light, and the leakage or entry of light with respect to the adjacent wells cannot be completely blocked and prevented, there is a concern of a measurement with a high accuracy not being able to be performed.

Furthermore, since the detection module divides the light path using a half mirror at the time light from the vessels is received or is irradiated, there is a need to take a long light path length within the measurement device, and it has a problem in that there is a concern of the device scale becoming large.

In a case where the detection module is one that moves such that it passes the respective wells that are arranged on the microplate and the number of wells becomes large, there is a concern of the processing time becoming long due to the movement distance being long, and in addition, there is also a concern of the problems of the measurement device mentioned above occurring.

Moreover, at the time an optical measurement is performed on a sealed reaction vessel, there is a concern of the lid which has transparency, or the optical system elements, becoming cloudy from condensation, and the measurements becoming difficult.

Consequently, in order to perform nucleic acid amplification and the like, as a precondition thereof, specialized researchers or technicians become necessary, and this situation is preventing the generalization of genetic analysis and the expansion of clinical applications in hospitals, and the like.

Therefore, at the time of clinical use and the like, in order to prevent cross-contamination and to reduce user labor, and to easily perform the genetic analysis of nucleic acids from the extraction, the amplification, and further, by means of a measurement, then consistently automating the steps from extraction of the target compound, reacting such as amplifying, up to measurement, and miniaturization of the device, and the provision of an inexpensive, high-accuracy device are important.

PRIOR ART DOCUMENTS

Patent Documents

[Patent Document 1] International Publication WO96/29602
[Patent Document 2] Japanese Unexamined Patent Publication No. 2002-10777
[Patent Document 3] United States Patent No. 7148043
[Patent Document 4] United States Patent No. 7749736

SUMMARY OF THE INVENTION

Problems to be Solved by the Invention

Therefore, the present invention is one that has been achieved in order to solve the problems mentioned above. A first object thereof is in providing a light measurement apparatus for a reaction vessel, and a method thereof that, with regard to the optical state within a reaction vessel with respect to nucleic acids and the like, makes rapid and efficient measurements with a high accuracy and reliability possible.

A second object is in providing a light apparatus for a reaction vessel, and a method thereof that, by simplifying the construction of the optical system and performing measurements using a small number of measurement devices with respect to a plurality of reaction vessels, prevents the expansion of the apparatus scale and increases in the complexity of the apparatus construction, and can be inexpensively manufactured and utilized.

A third object is in providing a light measurement apparatus for a reaction vessel, and a method thereof that, by consistently automating in parallel the optical measurements with respect to the plurality of reaction vessels, in which reactions such as amplification of nucleic acids are performed, and the associated processing therein, processing with a high reliability can be performed by preventing with certainty; contaminations due to the entry of contaminants into the plurality of reaction vessels from the exterior, or liquid leakage from the plurality of reaction vessels, and the cross talk of light between adjacent measurement devices at the time of measurement.

Means for Solving the Problem

A first aspect of the invention is a light measurement apparatus for a reaction vessel comprising: two or more linking portions to which is provided front ends of one or two or more light guide portions that are directly or indirectly linkable with two or more reaction vessels and optically connect with the interior of the reaction vessel to which it is linked;

a connecting end arranging body that has an arranging surface that arranges and supports along a predetermined path, two or more connecting ends, to which is provided back ends of the light guide portions, in which the front ends thereof are provided to the linking portions, the connecting ends are provided corresponding to the respective linking portions;

a measurement device that has one or two or more measuring ends that are successively optically connectable with the respective connecting ends along a predetermined path, and in which light based on an optical state within the reaction vessels is receivable by means of optical connections between the connecting ends and the measuring ends, the measuring ends are provided approaching or making contact with the arranging surface; and a light guide switching mechanism that relatively moves the respective connecting ends arranged on the connecting end arranging body and the respective measuring ends such that they are successively optically connected. In a case where the measurement device comprises a plurality of types of measurement devices, it is preferable to provide with respect to the respective measurement devices, and at the very least between adjacent measurement devices, a modulator that modulates the intensity of the light to be received by the measurement devices at mutually different predetermined frequencies, and a tuner that, with regard to the light received by the measurement devices, performs tuning to the predetermined frequencies, and obtains the corresponding intensity of the received light.

It is preferable for the vessel group, to which the reaction vessels are provided, to have in addition to the reaction vessels, two or more liquid housing parts that house liquids such as samples, reagents, and the like. Furthermore, the vessel group includes a microplate in which wells representing a plurality of liquid housing parts are arranged in a matrix form or a column (row) form, or a cartridge form vessel in which wells representing a plurality of liquid housing parts are arranged in a row form. In a case where amplification of nucleic acids is performed, the vessel group is provided with two or more liquid housing parts housing for example; a sample, a magnetic particle suspension in which magnetic particles that are able to capture the nucleic acids or the fragments thereof, which represent the amplification subject, are suspended, a solution for separating and extracting used for the separation and the extraction of the amplification subject, and an amplification solution used in nucleic acid amplification.

Furthermore, it is preferable for the two or more linking portions to be provided such that they are arranged on the light guide stage.

Here, the "amplification solution" represents, in a case where amplification is performed by the PCR method for example, a template DNA solution which is the amplification subject, a primer solution, a DNA polymerase solution, a nucleotide solution, a reaction buffer solution, and the like. In a case where amplification is performed by the SPIA method, it represents a DNA/RNA chimera primer solution, a DNA polymerase solution, an RNaseH solution, and the like. Furthermore, generally, methods for performing real-time PCR using fluorescent reagents containing a fluorescent compound include the intercalation method, the hybridization method, and the LUX method. In the "intercalation method", a fluorescent compound such as SYBR (registered trademark) GREEN I or ethidium bromide, enters into double-stranded DNA at the time of the elongation reaction, and is a method in which the DNA amount is measured by irradiating an excitation light and utilizing the fluorescent light-emitting characteristics. Therefore, at the very least, the fluorescent material and a quencher that suppresses the light emission of the fluorescent material must be contained within the amplification solution. The "hybridization method" is a method that detects only a target PCR product by using a DNA probe labeled with a fluorescent material in addition to a PCR primer. That is to say, as a result of the DNA probe labeled by the fluorescent light fluorescent material hybridizing with the target PCR product, the hybridized DNA (amount) thereof is detected. The "LUX method" is one that utilizes a property in which the fluorescent light signal of the fluorescent compound labeling the oligonucleotide is affected by the shape (such as a sequence, a single-strand, or a double-strand) of the oligonucleotide thereof. In actual real-time PCR, a PCR primer (LUX primer) that is labeled with one type of a fluorescent compound and a contrastingly unlabeled PCR primer are used to perform real-time PCR. The LUX primer thereof is labeled with a fluorescent compound in the vicinity of the 3'-terminus, and is designed such that it takes a hairpin structure in the interval between the 5'-terminus. When the LUX primer takes a hairpin structure, the quenching effect is resolved, and the fluorescent light signal becomes increased. By measuring this signal increase, the amount of the PCR product can be measured.

Examples of the material of the vessels, which includes the reaction vessels, the lid, and the like, include resins such as polyethylene, polypropylene, polystyrene and acrylic, glass, metals, and metal compounds. The size of the vessels is, in addition to several μL to several 100 μL of liquid being storable, a size in which the ends of the dispensing tips are insertable for example. In the case of a cylindrical shape, the diameter of the size of one vessel is several mm to several 10 mm, and the depth is several mm to several 10 mm for example.

It is preferable for the interior of the reaction vessels to be temperature controllable by a temperature controller.

The "temperature controller" has a temperature source that is able to lower the temperature within the reaction vessels, which house the liquids that become subjected to temperature control, based on a signal from the exterior for example. The temperature source is one in which, for example, a Peltier element, a heater, a cooling device, and the like is provided on a block-shaped member. In order to perform processing such as PCR, the temperature controller is preferably a thermal cycler using a Peltier element. That is to say, it is preferable for temperature control to be achieved by providing a block for temperature control as a temperature source to the vessel group or on the stage, in which temperature is raised and lowered by means of a Peltier element, that makes contact with or is adjacent to a portion (a lower side wall section for example) or the entirety of the reaction vessel. Furthermore, it is also possible to perform temperature control of an isothermal amplification by means of the LAMP method.

"Temperature control" represents, with respect to a liquid or a vessel that becomes the subject thereof, the maintaining of one or two or more set predetermined temperatures for set time periods, according to a specified sequence, and the execution at a specified frequency. The instructions to the temperature controller are carried out by sending a corresponding signal based on a program.

The "predetermined temperature" is a target temperature that an object, such as a liquid that becomes the subject, is to reach. In a case where nucleic acids, such as the DNA contained in a liquid, or oligonucleotides and the like, which represent fragments of nucleic acids, are amplified by the PCR method for example, the predetermined temperature that is set is a temperature cycle performed in the PCR method. That is to say, it represents temperatures that are respectively necessary for the denaturation, the annealing or the hybridization, and the elongation of DNA of approximately 94° C., a temperature in the interval from 50° C. to 60° C., and a temperature of approximately 72° C. for example. On the other hand, in the case of the SPIA method (trademark), it becomes set at a fixed temperature, such as 55° C. for example.

Furthermore, the predetermined temperature includes a temperature for transition acceleration that shortens the transition time and keeps the single cycle time within a predetermined cycle time as a result of, in the case of a transition from a high-temperature predetermined temperature to a low-temperature predetermined temperature, performing cooling at a temperature for transition acceleration that is lower than these predetermined temperatures by means of the temperature controller, or, at the time of a transition from a low-temperature predetermined temperature to a high-temperature predetermined temperature, by performing heating at a temperature for transition acceleration that is even higher than these predetermined temperatures for example. The "predetermined time" is the time necessary for maintaining the respective temperatures, and although it depends on the type of the amplification method, the reagents and the amount of liquid used in the PCR method, and the shape, the material, the size, the thickness, and the like, of the nozzles, a single cycle is, in total, from several seconds to several 10 seconds for example, and the processing time for the PCR method as a whole is of the order of approximately several minutes to several 10 minutes for example. The transition time is also included in the predetermined time.

The "linking portion" is a member that is able to be releasably linked with the reaction vessel directly, or indirectly via the sealing lid and the like. Provided to the linking portion is the end of a light guide portion that is able to guide the light based on the optical state within the reaction vessel, by optically connecting with the interior of the reaction vessel. Here, the "linking with the reaction vessel" represents approaching or joining with the aperture, the outer wall, or the outer bottom portion of the reaction vessel or a mounted sealing lid or sleeve and the like. Furthermore, "approaching" represents, without making contact, an approach to an extent that optical connection of the interval with the light guide portions is possible. Moreover, "joining" includes making contact, close contact, adhesion, fitting, and mounting, and at the very least represents making contact such that optical connection of the interval between the light guide portions is possible. As a result of this linking, the light guide portion provided to the linking portion and the interior of the reaction vessel are optically connected. The linking portion is a plate-shaped section of the light guide stage mentioned below to which the light guide portion is provided for example. The "light guide portion" is an optical system element, or a combination thereof, in which light is able to pass through. The end of the light guide portion is a hole piercingly provided in the plate-shaped section thereof, a transparent section such as an optical fiber, or an optical system element such as a lens. Alternatively, for example, it is a member of a cylindrical shape, and the like, provided such that it protrudes from the light guide stage, and the end of the light guide portion is a cavity provided in the member of a cylindrical shape, and the like, a transparent section such as an optical fiber, or an optical system element such as a lens, or one end thereof. It is preferable for the light guide portion to be such that a portion thereof has a flexibility. In this case, it represents an optical fiber or an optical fiber bundle, or a combination of these with an optical element such as a lens for example. If fluorescent light is measured, there is a case where two or more light guide portions are provided, and in such a case, they can be used such that a portion thereof are for irradiation, and the others are for receiving light. The connecting ends are provided with these optical elements, or the other ends thereof. Furthermore, a case where it is directly linked with the aperture of the reaction vessel represents a case in which the interior of the reaction vessel is sealed using mineral oil and the like, and in this case, it is preferable to form the linking portion such that it is able to directly seal the reaction vessel. Furthermore, in a case where the linking is performed outside of the aperture, there is a need for the reaction vessel or the linking section thereof to have a transparency. It is preferable, in order to prevent condensation, for the material of the linking portion to be formed by a resin such as a PEEK material, which has a low heat conductivity and has a rigidity, such that the heat from the heating portion is not released through the linking portions. Furthermore, if the heat from the heating portion is not released through the linking portions, it is possible to prevent the effects of heat toward the optical system elements, such as an optical fiber or a lens, that are provided to the linking portion. The spacing between adjacent connecting ends on the arranging surface of the connecting end arranging body is preferably formed such that it becomes smaller than the spacing between adjacent linking portions on the light guide stage. Consequently, it becomes possible integrate the arrangement of the connecting ends with respect to the arrangement of the linking portions.

The "predetermined path" represents, as a result of the measuring ends and the connecting end arranging body relatively moving, a path on a plane surface or a curved surface whereby the measuring ends are able to scan all of the connecting ends arranged therealong. Furthermore, the path that connects all of the connecting ends represents a single or multiple line segments that do not intersect (including zigzag lines and closed straight lines), curved lines (including spirals and closed curved lines), or a path along a combination of these and the like. Preferably, the respective single or multiple paths are continuous, and paths along straight line segments without cusps or corners, or smooth curves that have a curvature that the measuring ends are able to follow, are preferable.

There is a case where the linking portions and the connecting ends correspond one-to-one, a case where they correspond many-to-one, and a case where they correspond one-to-many. Here, midway, it is possible for the light guide portions to be branched or joined, or a light guide portion bundle comprising a plurality of light guide portions to be branched or joined.

It is preferable for the predetermined path to be determined based on the number, the shape, the arrangement, or the size of the measuring ends on the measuring device, such that smooth scanning is possible. For example, a predetermined path along a straight line in which, for the movement of the connecting ends with respect to the measuring ends, there are no sudden changes in direction, such as changes to an obtuse angle or a right angle direction with respect to the traveling direction, is preferable.

The arrangement pattern of the linking portions is a matrix form, a column form, or a row form for example. The arrangement pattern of the connecting ends is the same arrangement, or a similar arrangement that differs only in size for example, or in a case where the arrangement pattern is different, examples include the case of a circular form, other closed curved forms, a single column form, or a matrix form having a smaller number of columns or rows. The predetermined path is determined such that it passes through all of the arranged connecting ends. The connecting ends also include a case where they are mutually movably provided with respect to the linking portions, and a case where they are immobile with respect to the linking portions, and are provided as a connecting end arranging body on a connecting end arranging surface on the opposite side of the arranging surface of the linking portions of the same light guide stage.

Furthermore, it is preferable for the arrangement of the connecting ends to be such that they are integrated with respect to the arrangement of the linking portions. In this case, it is preferable for the light guide portion to have a flexibility. "Integration" is preferably performed by means of the predetermined path (or the arrangement pattern of the connecting ends) representing a smaller region area or a smaller spacing than the region area that encloses the arrangement pattern of the linking portions on the light guide stage or the spacing between adjacent linking portions, and by making the total scanning distance short. Consequently, in a case where the speed is made the same, processing within a shorter time than a case where the linking portions directly scan the measuring ends is possible. Furthermore, the scale of the apparatus is also made spatially smaller, which is of benefit for reducing manufacturing costs and the effective use of a workspace.

For example, in a case where "integration" is performed by making the spacing of adjacent connecting ends on the arranging surface of the connecting end arranging body smaller than the spacing of adjacent linking portions on the light guide stage, it was experimentally confirmed that when the plurality of reaction vessels were arranged with a spacing of 9 mm pitch, and when the external diameter of the optical fiber of the light guide portion was 1.5 mm, the pitch of the arrangement of the connecting ends could be set to 3.75 mm.

The extent of integration is such that the greater it becomes, the more preferable it is. This is because the processing time is shortened and the scale of the apparatus is spatially compressed. However, at the very least, it is at most an extent in which the relative movement or scanning of the connecting end arranging body and the measuring device is able to complete the receiving of the light from all of the reaction vessels to be measured within the stable light receivable time. Here, the "stable light receivable time" represents the time in which the optical state within the reaction vessels, for which the light is receivable, is stably maintained. In the case of the intercalation method or the LUX method of real-time PCR, or the TaqMan probe of the hybridization method for example, it corresponds to the time in which the elongation reaction of the respective cycles of PCR is performed. In a case where a FRET probe is used in the hybridization method, it corresponds to the time in which annealing is performed.

Consequently, it can be applied with respect to a light emitter with a short stable light receivable time and the like, and the versatility is high.

If the time taken for a single cycle is made several 10 seconds or several minutes for example, the stable light receivable time becomes several seconds or 10 seconds. However, the fluorescent light detection amount of the initial cycles of a PCR reaction is below the detection limit, and the later cycles of the PCR reaction become a plateau state, and in order to secure quantitativeness by a strict definition, it must be within a range of the amplification curve in which an exponential PCR amplification can be observed. The present invention is one in which the stable light receivable time utilizes the fact that the movement time of the measuring end between the reaction vessels can be used, and by performing the relative movement necessary for receiving the light from the respective reaction vessels within the stable light receivable time, the receiving of the light from the plurality of reaction vessels can be performed approximately in parallel by means of a single measuring device, or a sufficiently small number in comparison to the number of reaction vessels, without using complicated optical system elements and without expanding the scale of the apparatus.

The "optical state" represents a state such as light emissions, colors, color changes, or light variations. The light based on the optical state represents light from light emissions or light variations, or reflected light from light irradiated with respect to colors or color changes, or transmitted light, scattered light and the like.

The "connecting ends and the measuring ends are successively optically connected" represents that the connecting ends and the measuring ends are optically connected by becoming opposed at a close proximity. Since the amount of light received by the measuring device at the moment of connection corresponds to a maximum value, the measurement control portion specifies the data to be measured by calculating the maximum value of the amount of light.

The "measuring device" is one that makes fluorescence and chemiluminescence measurements possible for example, and in the former case, it has a filter for the irradiation of one or two or more types of excitation light and the receiving of fluorescent light having one or two or more types of wavelengths. It is preferable for these to be guided using an optical fiber. Furthermore, there is a case where they are provided to the plurality of types of measurement devices such that they correspond to the magnitude and the range of wavelengths (or frequencies).

The "measuring end" has, at the very least, an inlet for the light to be received provided to the measuring device, and in the case of a fluorescence measurement, has an outlet for the light to be irradiated. These can be provided as separate measuring ends. The inlet and the outlet are respectively optically connected to a light receiving portion comprising a photoelectric element provided in the interior, or to an irradiation source. At that time, they can be respectively connected via the light guide portion for receiving light and the light guide portion for irradiation. Furthermore, the connecting end arranging body, the measuring ends, and the measurement device are preferably provided at separated locations such that they do not directly make contact or are not in the vicinity of the reaction vessels or the stage for mounting, in which heating control or temperature control is performed.

The light measurement apparatus for a reaction vessel, although not explicitly specified, additionally has "a measurement control portion". The "measurement control portion" controls the measuring device and a light guide switching mechanism, comprises a computer (CPU) built into the light measurement apparatus for a reaction vessel and a program that drives the computer, and achieves measurement control by transmitting a signal through a DA converter to the respective control portions that drive the transfer mechanisms for example.

Here, the "modulator" represents a device that modulates the strength of the light to be received by the respective measurement devices at predetermined frequencies. For example, in a case where the optical state within the reaction vessels represents the emission of fluorescent light, it has an excitation light modulation portion as described below. The excitation light modulation portion includes a drive circuit, such as an oscillating voltage supply circuit that makes a voltage applied to an irradiation source, which is for generating an excitation light to be irradiated to a fluorescent compound, an oscillating voltage having a predetermined frequency, and various devices for blinking of the light to be received at the predetermined frequency, such as an optical shutter, a rotating polygon mirror, and an optical chopper formed by a light transmitting-hole type rotating body. Examples of the "oscillating voltage of the predetermined frequency" include sinusoidal oscillation, and pulse wave-type variations including blinking of the light. The "tuner" represents a device that, with respect to the received light, obtains the corresponding light intensity of the received light by performing tuning to the predetermined frequency. For example, it has a bandpass filter circuit that extracts the frequency or a frequency band. This is generally because the wavelength of the excitation light is shorter than the wavelength of the fluorescent light, and the intensity is higher. Therefore, it is possible that measurements are performed where a plurality of types of fluorescent light and a plurality of types of excitation light are used in a state where they are mutually similar. In such a case, if the wavelength of a given excitation light and the wavelength of the fluorescent light overlap, the extraction of the fluorescent light from the excitation light becomes difficult. Therefore, at the very least between adjacent measurement devices, they can both be discriminated by performing modulation to different predetermined frequencies. Consequently, other optical noise, such as natural light, can be excluded.

The "predetermined frequency" is in a range from 1 Hz to 1 MHz, and is preferably from approximately 1 kHz to 10 kHz. Since it is "at the very least between adjacent measurement devices", it is possible to use the same frequency between measurement devices that are separated by a fixed distance or more.

A second aspect of the invention is a light measurement apparatus for a reaction vessel in which, at the time light is received by the measurement device, at the very least, a measurement device body excluding the measuring ends is immovably provided with respect to the light guide stage, which is provided with the reaction vessels and the linking portions linked with the same.

Therefore, there is a case where the connecting end arranging body moves with respect to the measuring ends, or the measuring ends move with respect to the connecting end arranging body, and the measurement device body may be movably provided with respect to the reaction vessels or the light guide stage until the light guide stage is linked with the reaction vessels. The former case represents a case where the measurement device body is linked with the light guide stage or a case where it is linked with movements in a portion of the directions for example. Furthermore, the latter case represents a case where the measurement device body is linked with the reaction vessels, or is fixed to the stage together with the reaction vessels. The measuring ends, in a case where they are present, include light guide portions, which are on the exterior of the measurement device body, up to the measuring ends.

A third aspect of the invention is a light measurement apparatus for a reaction vessel, wherein the measurement device comprises a plurality of types of specific wavelength measurement devices that are able to receive light of specific wavelengths or specific wavelength bands, the specific wavelength measurement devices having at least one measuring end that is successively optically connectable with the connecting ends along the predetermined path, and the frequencies of the modulators provided to the specific wavelength measurement devices being mutually different, at least between adjacent predetermined specific wavelength measurement devices. In a case where the light based on the optical state is a fluorescent light, the specific wavelength measurement devices are provided with an irradiation source that irradiates a predetermined excitation light that excites the corresponding fluorescent light of a specific wavelength or a specific wavelength band, and a light receiving portion that is able to receive the fluorescent light of the specific wavelength or the specific wavelength band, and the modulators that correspond to the respective specific wavelength measurement devices are provided with an excitation light modulation portion that modulates the excitation light at the predetermined frequency, and the tuners are provided with a bandpass filter circuit or a lock-in amplifier that, with respect to the light received by the light receiving portion, extracts the intensity data of the light having the predetermined frequencies.

Here, the measuring end is provided with a cavity, an optical element such as a lens, or a light guide portion such as an optical fiber for example. Furthermore, the measuring end is provided with an irradiation aperture that connects with the irradiation source, and a light receiving aperture that connects with the light receiving portion. The "bandpass filter circuit" represents a circuit that extracts from a measurement subject signal only the light signal that possesses a frequency band that contains the (modulated) predetermined frequency, and removes signals of all other frequencies. Furthermore, a filter circuit in which a high-pass filter and a low-pass filter are combined is exemplified. The "lock-in amplifier" represents a circuit that takes a measurement subject signal and a reference signal having the modulated predetermined frequency, multiplies the two by means of a multiplier (Phase Sensitive Detector), and by smoothing thereafter, obtains an output signal possessing the intensity component of the signal having the predetermined frequency.

A fourth aspect of the invention is a light measurement apparatus for a reaction vessel, that has two or more linking portions provided on the light guide stage, and a stage transfer mechanism that relatively moves the light guide stage with respect to the reaction vessels such that the linking portion is simultaneously directly or indirectly linked with the two or more reaction vessels.

Preferably, the spacing between adjacent connecting ends on the arranging surface of the connecting end arranging body is formed such that it becomes smaller than the spacing between adjacent linking portions on light guide stage.

In a case where the stage transfer mechanism makes the light guide stage relatively movable in the vertical direction with respect to the vessel group, the sealing lids that are mounted such that they cover the apertures of the reaction vessels can be pressed or shaken. That is to say, it is preferable for the measurement control portion, following indirectly linking with the linking portions via the sealing lids such that it covers the apertures of the reaction vessels, to perform control such that it presses or shakes the sealing lids. By pressing, the sealing of the reaction vessels can be performed with certainty. In addition, by shaking, the sealed state between the apertures of the reaction vessels and the sealing lids can be rapidly and easily removed and released. Therefore, a high processing efficiency and reliability can be obtained.

In a case where the linking portions are not linked by joining, such as by directly or indirectly fitting with the apertures of the reaction vessels, but by linking with the reaction vessels by approaching the reaction vessels, it is possible to successively and smoothly repeat the linking between the linking portions and the reaction vessels, and the releasing thereof, by means of horizontal movements without performing relative movements in the vertical direction.

Furthermore, the two or more linking portions provided to the light guide stage are arranged on a linking portion arranging body that is movable in the horizontal direction with respect to the light guide stage in a state in which they are directly or indirectly simultaneously linkable with two or more reaction vessels. Moreover, by moving the linking portion arranging body with respect to the light guide stage, a light measurement apparatus for a reaction vessel that, without moving the light guide stage, makes more reaction vessels linkable than the number of reaction vessels that are simultaneously linkable by the linking portion arranging body, can be provided. In this case, it is preferable for the linking between the respective linking portions and the reaction vessels to be performed within shielded regions that are mutually shielded, such as within two or more grooves or two or more regions that are mutually separated by a partition wall, to which the respective linking portions are insertable, that extend in a horizontal direction in which the linking portion arranging body thereof is movable, and are also provided to the light guide stage for each of the linking portions. Consequently, the contamination of light from other reaction vessels can be prevented with certainty.

In this case, the linking portions can be easily and rapidly linked with the reaction vessels by merely moving in the horizontal direction without movements of the light guide stage in the vertical direction. Therefore, by setting the speed of the linking portion arranging body such that it includes the horizontal movements of the linking portion arranging body and can be performed within the stable light receivable time, it becomes possible to receive light and perform measurements essentially in parallel with respect to an even greater number of reaction vessels by means of a single set of measurement devices.

In a case where the measurement device has one or two or more measuring ends that are optically connectable with the connecting ends, and a plurality of types specific wavelength measurement devices that are able to receive light of specific wavelengths or specific wavelength bands, then preferably provided is a measuring end aligning portion that aligns the plurality of measuring ends such that they are optically connectable with the respective connecting ends along the predetermined path.

The "aligning" is integrally or linkingly performed. "Integrally" represents arrangement such that the intervals between the measuring ends are mutually fixed and do not have any degrees of freedom. "Linkingly" represents arrangement such that the intervals between the measuring ends have degrees of freedom to some extent, such as in a chain. There is a case where the "aligning" is such that the respective measuring ends are lined up along the scanning direction of the predetermined path, or a direction perpendicular to the scanning direction. In the latter case, the predetermined path is such that a plurality of paths are lined up in parallel.

According to the present aspect of the invention, by using a plurality of types of luminescent compounds, colored compounds, color changing compounds, or light variation compounds, and performing amplification processing in parallel under the same conditions on a plurality of types of amplification subjects in a single reaction vessel, it is possible to perform multiplex PCR amplification or multiplex real-time PCR on a plurality of types of amplification subjects by using a primer labeled with a plurality of types of luminescent compounds for example.

Since it is "light of a specific wavelength or a specific wavelength band", it represents, in terms of visible light, a range of wavelengths such as a red light, a yellow light, a green light, a blue light or a violet light for example.

A fifth aspect of the invention is a light measurement apparatus for a reaction vessel wherein the vessel group is provided with sealing lids, which have transparency, that are mounted on apertures of one or two or more of the reaction vessels, and seal the reaction vessels.

Here, the "sealing lid" includes, in addition to those that are inflexible and a plate form or block form, those that are a film form or a membrane form and have a flexibility. The "mounting" includes fitting, threading, friction, adsorption, attachment, adhesion, and the like. In these cases, detachable mounting is preferable.

Furthermore, in a case where the respective linking portions of the light guide stage are linked at the apertures of the respective reaction vessels, it is preferable to make the linking portions or the nozzles pressable or shakable with respect to the sealing lids covering the apertures of the reaction vessels.

It is preferable for the linking portions to be provided such that they downwardly protrude from the light guide stage. In this case, the linking portions, for example, have a shape such as a rod shape, a cylinder shape, a cone shape, and the like, and the lower end portions of the members are preferably able to make contact with the sealing lids.

The sealing lids singularly cover the apertures of one or two or more reaction vessels. The sealing lids are moved by being mounted to the nozzles mentioned below, and cover the apertures of the reaction vessels by using the tip detaching mechanism for example. To accomplish this, one or two or more indentations for mounting that are mountable on the one or two or more nozzles are provided on the upper side of the sealing lids. The one or two or more linking portions can be linked with the reaction vessels by being inserted within these indentations (which are also indentations for linking) by means of vertical direction movements of the light guide stage.

It also is possible, without moving the sealing lids by means of the nozzles, to provide a dedicated sealing lid transport mechanism. As the sealing lid transport mechanism, the light measurement apparatus for a reaction vessel has a transporting body that is movable with respect to the vessel group, and one or two or more grippers arranged on the transporting body according to the arrangement of the reaction vessels that, with respect to the cover plate that covers the apertures of the respective reaction vessels, and the sealing lids having mounting portions that protrude on the lower side of the cover plate excluding the center portion, in which light is able to pass through, and to which the cover plate is mountable to the reaction vessel, grips the cover plate such that the mounting portions are exposed on the lower side in a state in which they are mountable to the reaction vessels for example. Furthermore, if the sealing lid transporting body is made to be linked with the light guide stage, the apparatus construction is simplified, and the expansion of the apparatus scale can be prevented.

In this case, since it is not necessary to provide an indentation for mounting the nozzles and the like on the upper side of the sealing lid, the linking portion can be easily linked by just horizontal direction movement between the apertures of the reaction vessels on the sealing lid without vertical direction movements of the light guide stage. In this case, if the horizontal direction movement of the linking portion can be performed within the stable light receivable time, it becomes possible to receive light and perform measurements essentially in parallel with respect to an even greater number of reaction vessels.

A sixth aspect of the invention is a light measurement apparatus for a reaction vessel, wherein the light guide stage is provided with a heating portion that is able to heat the sealing lids.

The measurement control portion, after simultaneously mounting the sealing lids to the linking portions, and following control of the stage transfer mechanism such that the optical linking portions are simultaneously indirectly linked with the two or more reaction vessels, controls the heating portion such that the sealing lids are heated for example. The "heating portion" has a heating function at a temperature that is set based on the magnitude of an applied electric current or by an ON/OFF control for example.

Here, the heating of the sealing lids by the heating portion is performed for preventing condensation at the time of temperature control of the reaction vessels sealed by the sealing lids.

A seventh aspect of the invention is a light measurement apparatus for a reaction vessel provided with a temperature controller having a temperature source that is provided making contact with or approaching the lower side wall sections of the reaction vessels, and a heating portion provided such that it is able to make contact with or approach the upper side wall sections of the reaction vessels positioned further on an upper side than the lower side wall sections of the reaction vessels, and that has a heat source that is able to heat the upper side wall sections.

Here, the "lower side wall section" represents a wall section or a portion thereof including the bottom portion that encloses a volume section, which is a portion (1% to 90% for example) of the entire volume of the reaction vessel in which a predetermined liquid amount determined beforehand is housable. The lower side wall section represents the section of the wall section in which the rated liquid amount of liquid is housable for example. In a case where the reaction vessels comprise wide-mouthed piping parts that are linked with the linking portions, and a narrow-mouthed piping part, it is provided on the narrow-mouthed piping part for example. The "upper side wall section" represents, within the entire volume of the reaction vessel, a vessel section enclosing the remaining volume of the lower side vessel section, in which the rated liquid amount is housed, or a portion thereof The "upper side wall section" is normally preferably provided on the upper side of the reaction vessels leaving a spacing with the lower side wall section. The upper side wall section becomes closer to the aperture, the sealing lid, or the linking portion than the lower side wall section. In the case of the vessel comprising the wide-mouthed piping part and the narrow-mouthed piping part, and in a case where the linking portion is linked by fitting with the wide-mouthed piping part, the upper side wall section is provided on the wall section of the wide-mouthed piping part for example. The upper side wall section is a section that corresponds to a band shape along the circumference of the vessel wall for example.

The measurement control portion, following controlling the stage transfer mechanism such that the linking portions are simultaneously directly or indirectly linked with the reaction vessels, controls the heating portion such that direct or indirect condensation on the linking portions is prevented. "Indirectly linked" represents a case where the linking portions are linked with the reaction vessels via the sealing lids, the outer walls of the reaction vessels, and the like. "Control of the heating portion" is performed according to the "temperature control" for preventing condensation. For example, the heating temperature is controlled such that it is set from several degrees (a temperature exceeding the dew point of water vapor that is necessary for preventing condensation) to several 10° C. (a temperature that is sufficiently lower than the melting point of the raw material of the reaction vessels), for example, 1° C. to 60° C., or preferably approximately 5° C., higher than the respective predetermined temperatures set by the temperature control for example. In a case where the amplification is by PCR, heating is performed at a temperature that is several degrees higher than 94° C., such as 100° C., and in an isothermal case, in a case where the predetermined temperature is approximately 55° C., heating is performed at a temperature that is several degrees higher than this for example, such as from approximately 60° C. to 70° C. The heating temperature depends on the amount of liquid representing the subject of temperature control, and also the positions of the arranged reaction vessels. For example, according to experiments, when the temperature set by temperature control was 95° C. and the amount of liquid was 25 μL, condensation disappeared at 113° C.

As a result of the heating portion performing heating directly with respect to the reaction vessels and not the linking portions or the sealing portions, thermal effects toward the optical system elements provided to the linking portion, or the measuring ends near the linking portions, are reduced or removed. Therefore, the degradation of optical system elements such as prisms, optical fibers, various lenses, such as concavoconvex lenses, ball lenses, aspheric lenses, drum lenses, and graded index rod lenses, mirrors, waveguide tubes, and the like, is prevented, and the reliability of the image that can be obtained through the optical system elements can be increased. For the linking portions, by using various lenses, such as ball lenses and aspheric lenses, which represent the optical system elements, the light that is generated within the reaction vessels and is outgoing in the aperture direction is focused with certainty, and can be guided by being incident to the light guide portion, such as an optical fiber.

Here, the reaction vessels; the temperature controller, which has a temperature source provided such that it is making contact with or approaching the lower side wall sections of the reaction vessels, and performs temperature control of the interior of the reaction vessels; and the heating portion provided such that it is making contact with or approaching the upper side wall section, which has a heat source that is able to heat the upper side wall section, configure the reaction vessel control system.

In that case, the reaction vessel preferably comprises a wide-mouthed piping part, and a narrow-mouthed piping part that is formed narrower than the wide-mouthed piping part and is provided on a lower side of the wide-mouthed piping part and communicated with the wide-mouthed piping part. The end of the linking portion is fittable to the wide-mouthed piping part, liquids are housable in the narrow-mouthed piping part, and the lower side wall section is provided to the narrow-mouthed piping part, and the upper side wall section to the wide-mouthed piping part. Furthermore, it is preferable for the contact surfaces between the linking portion and the upper side wall section of the reaction vessel, which is heated by the heating portion, or the sealing lid which makes contact therewith, to be made as small as possible. Consequently, the effects of the heating portion toward the optical system elements of the linking portions can be reduced or removed.

An eighth aspect of the invention is a light measurement apparatus for a reaction vessel wherein a linking portion, which is directly or indirectly linkable with the reaction vessels and is provided with an optical element in the interior, is a material that is usable to a temperature higher than the dew point of water vapor, and has a thermal conductivity smaller than 1.0 W/(m·K) (W: watt, K: kelvin, m: meter).

Here, if the material is a resin for example, in a case where heating control by the heating portion is performed at 113° C., then as is clear from the Tables below, examples of materials that are applicable to these conditions include PEEK, MC nylon, fluororesins, and PBT. However, when rigidity is considered, PEEK is preferable.

Thermal Properties of Plastics

|  | Thermal conductivity [W/m · K] | Continuous usage temperature [° C.] | Coefficient of linear expansion [1/° C.] |
| --- | --- | --- | --- |
| PEEK | 0.25 | −50 to 250 | 5.0 × 10$^{-5}$ |
| MC nylon | 0.233 | −40 to 120 | 9.0 × 10$^{-5}$ |
| Polyacetal | 0.233 | −45 to 95 | 9.0 × 10$^{-5}$ |
| Fluororesin | 0.25 | −40 to 250 | 1.0 × 10$^{-4}$ |
| PET | 0.24 | room temperature to 100 | 5.5 × 10$^{-5}$ |
| PBT | 0.27 | room temperature to 120 | 1.0 × 10$^{-4}$ |
| ABS | 0.3 | room temperature to 50 | 9.5 × 10$^{-5}$ |

Numerical values are representitive values

A ninth aspect of the invention is a light measurement apparatus for a reaction vessel, wherein the light guide stage is provided to a nozzle head having a suction-discharge mechanism that performs suction and discharge of gases, and one or two or more nozzles that detachably mount dispensing tips in which the suction and the discharge of liquids is possible by means of the suction-discharge mechanism, and has a nozzle head transfer mechanism that makes the nozzle head relatively movable between the vessel groups.

In this case, in addition to further providing a magnetic force part that is able to apply or remove a magnetic force within the dispensing tips mounted on the nozzles or liquid housing parts provided in the vessel group, and which is able to adsorb the magnetic particles on an inner wall of the dispensing tips or the liquid housing parts, it is preferable to provide an extraction control part that controls the suction-discharge mechanism, the transfer mechanism, and the magnetic force part, and for the reaction solution, separates and extracts the solution of the amplification subject from the sample and houses it within the liquid housing parts as a portion of the amplification solution.

Here, the "solution for separating and extracting" includes a dissolving solution that breaks down or dissolves the protein forming the cell walls and the like contained in the sample and discharges the nucleic acids or the fragments thereof to the outside of the bacteria or the cell, a buffer solution that simplifies the capture of the nucleic acids or the fragments thereof by the magnetic particles, and additionally, a solution that dissociates from the magnetic particles, the nucleic acids or the fragments of nucleic acids captured by the magnetic particles. In order to perform the separation of the nucleic acids or the fragments thereof, it is preferable to repeat the suction and the discharge of the mixed solution.

The "dispensing tip" comprises for example a thick diameter portion, a narrow diameter portion, and a transition portion that communicates between the thick diameter portion and the narrow diameter portion. The thick diameter portion has an aperture for mounting, into which the lower end of the nozzle is inserted and the nozzle is mounted, and the narrow diameter portion has an end mouth portion in which liquids can flow in and flow out by means of the suction and discharge of gases by the suction-discharge mechanism. The dispensing tip and the nozzle are manufactured from organic substances such as resins of polypropylene, polystyrene, polyester, acrylic, and the like, and inorganic substances such as glass, ceramics, metals including stainless steel, metal compounds, and semiconductors.

The "suction-discharge mechanism" is for example a mechanism formed by a cylinder, a piston that slides within the cylinder, a nut portion joined to the piston, a ball screw on which the nut portion is threaded, and a motor that rotatingly drives the ball screw in both forward and reverse directions.

In a case where two or more nozzles are used, by respectively arranging two or more vessel groups so as to correspond to the respective nozzles within two or more exclusive regions corresponding to the respective nozzles, in which a single nozzle enters and the other nozzles do not enter, and by setting the respective exclusive regions for each different sample, cross-contamination between samples can be prevented with certainty.

The stage transfer mechanism at least partly utilizes the nozzle head transfer mechanism. It is preferable for the nozzle transfer mechanism, which moves the nozzles themselves in the Z axis direction, to also at least partly utilize the nozzle head transfer mechanism, and for the stage transfer mechanism and the nozzle transfer mechanism to be independently movable with respect to the Z axis direction movement.

A tenth aspect of the invention is a light measurement apparatus for a reaction vessel, wherein the nozzle is such that a sealing lid is retainable by mounting, and by detaching the sealing lid, the sealing lid is mountable on an aperture of the reaction vessel. The detaching of the sealing lid can be combined with the tip detaching mechanism that detaches from the nozzle the dispensing tip mounted on the nozzle. In this case, the "sealing lid" has a sealing portion that is mountable on the aperture of the reaction vessel, and an indentation for linking that is mountable on the nozzle. Furthermore, in the case of the linking portion indirectly linking with the reaction vessel by being mounted on the sealing lid, in a case where the outer diameter of the nozzle and the outer diameter of the linking portion are different, it is preferable for the indentation for linking of the sealing lid to be fitted with the end of the linking portion in place of the nozzle, be mounted, and make the linking portion able to retain the sealing lid. In this case, for the detaching of the sealing lid from the linking portion, it is preferable to provide a dedicated sealing lid detaching mechanism.

An eleventh aspect of the invention is a light measurement apparatus for a reaction vessel, wherein front ends of a light guide portion bundle, which comprises a plurality of light guide portions, are provided to the respective linking portions, back ends of a light guide portion bundle of a portion of the light guide portion bundle are provided to first connecting ends of the connecting end arranging body, a portion or all of the remainder of the light guide portion bundle is provided to second connecting ends of the connecting end arranging body, the predetermined path comprises a first path and a second path, and by means of movement of the connecting end arranging body, first measuring ends provided on the measurement device respectively relatively move along a first path comprising the first connecting ends, and second measuring ends along a second path comprising the second connecting ends.

A twelfth aspect of the invention is a light measurement apparatus for a reaction vessel, wherein the first measuring end optically connects with an irradiation source of the measurement device, the second measuring end connects with a light receiving portion of the measurement device, and the first measuring end is connectable with the first connecting end, and the second measuring end is connectable with the second connecting end.

Here, the connecting end arranging body has a plurality of pairs of first connecting ends and second connecting ends that are optically connected with the linking portion, and a single pair of a third connecting end and a fourth connecting end that is optically mutually connected by means of the light guide portion. The first measuring ends provided to the measurement device are relatively movable along a first path comprising a plurality of first connecting ends and a single third connecting end, and the second measuring ends provided to the measurement device are relatively movable along a second path comprising a plurality of second connecting ends and a single fourth connecting end. The first measuring ends optically connect with the irradiation source of the measurement device, and the second measuring ends connect with the light receiving portion of the measurement device. It is preferable for each pair to be such that the first measuring end is successively connectable with the plurality of first connecting ends and the single third connecting end, and the second measuring ends are successively connectable with the plurality of second connecting ends and the single fourth connecting end.

In this case, the excitation light emitted by the irradiation source is directly received by the light receiving portion via the light guide portion without being diverted to the linking portion and the reaction vessel, and the intensity thereof can be measured. Generally, in semiconducting light emitting elements that are used as excitation light sources, such as LEDs, the emission intensity can change depending on the temperature. On the other hand, the fluorescence intensity emitted by a fluorescent material dissolved in a solution is proportional to the fluorescent material concentration and the excitation light intensity. Many fluorescence measurements utilize the fluorescent material concentration dependence on the fluorescence intensity, and it is a measurement for estimating the fluorescent material concentration in a solution. However, fluctuations in the excitation light intensity also changes the fluorescence intensity in the same manner as fluctuations in the fluorescent material concentration. Consequently, by measuring the intensity of the excitation light and removing the effects toward the fluorescence intensity based on the fluctuations thereof, a high-accuracy measurement can be performed.

Furthermore, it is preferable for the front ends corresponding to the first connecting ends and the front ends corresponding to the second connecting ends to be arranged such that they are mixed. The "mixing of front ends" is, for a light guide portion bundle comprising a plurality of light guide portions, preferably an arrangement in which the front ends of two or more types of light guide portions are mixed such that they become uniform, such that uniform irradiation, and uniform receiving of light, are performed.

A thirteenth aspect of the invention is a light measurement apparatus for a reaction vessel, wherein the vessel group comprises two or more exclusive regions corresponding to nozzles of respective groups, which comprise one or two or more nozzles, in which nozzles of a single group enter and nozzles of other groups do not enter, and the respective exclusive regions at the very least have at least one of the reaction vessels, one or two or more liquid housing parts that house reaction solutions used in the reactions, and sealing lids that are transportable to the reaction vessels using the nozzles and are able to seal the reaction solutions housed in the reaction vessels, and the light guide stage is extendingly provided across all of the exclusive regions such that linking portions of the light guide stage are associated such that linking portions of a single group, which comprises one or two or more linking portions, enter the respective exclusive regions and linking portions of other groups do not enter.

In order to make "the nozzles of a single group enter and the nozzles of the other groups not enter" or "the linking portions of a single group enter and the linking portions of the other groups not enter", for example, this is performed by providing an exclusive region control part that controls the nozzle head transfer mechanism such that nozzles of a single group enter the respective exclusive regions and the nozzles of the other groups do not enter, and performs control such that the linking portions of a single group enter the respective exclusive regions and the linking portions of the other groups do not enter.

A fourteenth aspect of the invention is a light measurement apparatus for a reaction vessel that is further provided with a set of traversable nozzles comprising one or two or more nozzles that are movable such that they traverse the respective exclusive regions, and are able to enter the respective exclusive regions.

A fifteenth aspect of the invention is a light measurement apparatus for a reaction vessel, wherein inspection information that identifies samples or shows managed sample information and testing content is visibly displayed at the respective exclusive regions, and a digital camera, which obtains image data by imaging the content displayed at the respective exclusive regions, which includes the sample information and the testing content, is provided to the traversable nozzles.

Here, the "sample information" represents the information necessary for identifying or managing the sample, and examples of the information for identifying the sample include the attributes of the sample, such as the patient, the animal, the food, the soil, the polluted water, or the like, from which the sample was collected, and includes the name, the age, the sex, and the ID number of the patient, the sales location of the food, and the collection location and the collection date and time of the soil, or the physical properties of the collected sample, including the classification of the blood, the urine, the faeces, the bodily fluid, the cells, or the like, of the patient, the classification of the food, the classification of the soil, or the classification of the polluted water for example. Examples of the information that manages the samples include the collector and the collection date of the sample thereof, the contact person for the sample, and the inspection date of the sample thereof for example.

The "inspection information" represents information showing the content of the inspection performed with respect to the sample, and can include inspection items such as various genetic information (SNPs, base sequence determination for example), genetic testing, or other various protein information or the types of reagents utilized in the inspection, the production lot number of the reagents, the calibration curves for the reagents, the type and the structure of the instruments for testing, or the type of biological material fixed to a carrier and the like, for example. This information is displayed in a handwritten case, a printed case, a case where it is a barcode, or a case where it is a QR (registered trademark) code (a matrix type two-dimensional code) for example. The image data is analyzed, converted to analysis data corresponding to the code data, and output.

A sixteenth aspect of the invention is a light measurement apparatus for a reaction vessel comprising: a nozzle head provided with a suction-discharge mechanism that performs suction and discharge of gases, and one or two or more nozzles that detachably mount dispensing tips in which the suction and the discharge of liquids is possible by means of the suction-discharge mechanism; a vessel group having at the very least one or two or more liquid housing parts that house reaction solutions used for various reactions, a liquid housing part that houses a magnetic particle suspension in which magnetic particles that are able to capture a target compound are suspended, a liquid housing part that houses a sample, one or two or more liquid housing parts that house a solution for separating and extracting of the target compound, and two or more reaction vessels; a nozzle head transfer mechanism that makes an interval between the nozzle head and the vessel group relatively movable; a magnetic force part that is able to adsorb the magnetic particles on an inner wall of dispensing tips mounted on the nozzles; a light guide stage provided to the nozzle head and having two or more linking portions to which ends of one or two or more light guide portions, that are directly or indirectly linkable with the respective reaction vessels and optically connect with the interior of the linked reaction vessels, are provided; a connecting end arranging body having an arranging surface that arranges and supports along a predetermined path two or more connecting ends, to which back ends of the light guide portions, in which front ends thereof are provided to the linking portions, are provided, the connecting ends are provided corresponding to the respective linking portions; a measurement device having one or two or more measuring ends that are successively optically connectable with the respective connecting ends along the predetermined path, that is able to receive light based on an optical state within the reaction vessels by means of optical connections between the connecting ends and the measuring ends, the measuring ends are provided approaching or making contact with the arranging surface; and a light guide switching mechanism provided along the predetermined path of the connecting end arranging body that relatively moves the respective connecting ends and the respective measuring ends such that they become successively optically connected.

In a case where the measurement device comprises a plurality of types of measurement devices, it is preferable to provide with respect to the respective measurement devices, and at the very least between adjacent measurement devices, a modulator that modulates the intensity of the light to be received by the respective measurement devices at mutually different predetermined frequencies, and a tuner that, with regard to the light received by the respective measurement devices, performs tuning to the predetermined frequencies, and obtains the corresponding intensity of the received light.

Here, the "reaction solution" is for example an amplification solution used for nucleic acid amplification. Furthermore, the "target compound" represents nucleic acids or the fragments thereof, which is the amplification subject. It is preferable to provide a tip detaching mechanism that detaches the sealing lids or the dispensing tips from the nozzles. In the present apparatus, it is preferable to provide a sample supplying device having a dispensing function that supplies the samples, the reagents, the washing liquids, the buffers, and the like that are necessary for the vessel group at a position separate to the stage of the light measurement apparatus for a reaction vessel, and to make the whole stage, to which the supplied vessel group is built-in, be automatically moved to the position of the stage of the light measurement apparatus for a reaction vessel and to be made exchangeable. Consequently, processing, including preparation processing such as the dispensing processing or the supplying processing with respect to the vessel group, can be consistently performed.

It is possible to respectively combine the second aspect of the invention through to the thirteenth aspect of the invention with the present aspect of the invention.

A seventeenth aspect of the invention is a light measurement method for a reaction vessel comprising: moving a linking portion provided with an end of one or two or more light guide portions, with respect to two or more reaction vessels; simultaneously directly or indirectly linking the reaction vessels and the linking portions and optically connecting the interior of the linked reaction vessels and the light guide portions; performing temperature control within the reaction vessels; guiding light from the reaction vessels to a connecting end arranging body having an arranging surface that arranges and supports along a predetermined path two or more connecting ends, to which back ends of the light guide portions, in which front ends thereof are provided to the linking portions, are provided, the connecting ends are provided corresponding to the respective linking portions; and successively optically connecting along the predetermined path the one or two or more measuring ends provided to a measurement device, which are provided approaching or in contact with the arranging surface, and the respective connecting ends, by moving the connecting end arranging body, to thereby make the measurement device receive light based on an optical state within the reaction vessels.

In a case where the measurement device comprises a plurality of types of measurement devices, it is preferable, at the very least between adjacent measurement devices, to modulate the intensity of the light to be received by the measurement devices at mutually different predetermined frequencies, and with regard to the light received by the measurement devices, to perform tuning to the predetermined frequencies, and to obtain the corresponding intensity of the received light.

Furthermore, it is preferable for the front ends of a light guide portion bundle comprising a plurality of light guide portions to be provided to the respective linking portions, the light guide portion bundle to be such that the rear ends of a portion of the light guide portion bundle are provided to first connecting ends of the connecting end arranging body, a portion or all of the remaining rear ends of the light guide portion bundle to be provided to second ends of the connecting end arranging body, the predetermined path to comprise a first path and a second path, the connecting end arranging body to have a plurality of pairs of first connecting ends and second connecting ends that are optically connected with the linking portion, and a single pair of a third connecting end and a fourth connecting end that is optically mutually connected by means of the light guide portion, and at the time the first measuring end provided to the measurement device relatively moves along the first path, which comprises a plurality of first connecting ends and a single third connecting end, and the second measuring end relatively moves along the second path, which comprises the second connecting ends and the fourth connecting end, for the first measuring ends to optically connect with the irradiation source of the measurement device, and the second measuring ends to connect with the light receiving portion of the measurement device, and for each pair, for the first measuring end to successively connect with the plurality of first connecting ends and the single third connecting end, and the second measuring end to successively connect with the plurality of second connecting ends and the single fourth connecting end. The effects described above are also achieved in this case.

It is possible to respectively combine the second aspect of the invention through to the fifteenth aspect of the invention with the present aspect of the invention.

An eighteenth aspect of the invention is a light measurement method for a reaction vessel, wherein the measurement device has a plurality of types of specific wavelength measurement devices that are able to receive light of specific wavelengths or specific wavelength bands, and the respective specific wavelength measurement devices have at least one measuring end that is successively optically connectable with the connecting ends along the predetermined path. The method comprises aligning measuring ends of a plurality of types by a measuring end aligning portion, and successively optically connecting the measuring ends with the connecting ends along the path, to thereby make the respective specific wavelength measurement devices receive the light of specific wavelengths or specific wavelength bands based on an optical state within the reaction vessels.

A nineteenth aspect of the invention is a light measurement method for a reaction vessel comprising simultaneously mounting two or more sealing lids, which have transparency, that are arranged in the vessel group and are finable with apertures of the reaction vessels, on reaction vessels, and then moving the light guide stage with respect to the sealing lids of the reaction vessels.

A twentieth aspect of the invention is a light measurement method for a reaction vessel comprising pressing or shaking with respect to the sealing lids covering the apertures of the reaction vessels.

A twenty-first aspect of the invention is a light measurement method for a reaction vessel comprising heating the sealing lids sealing the reaction vessels through the light guide stage.

A twenty-second aspect of the invention is a light measurement method for a reaction vessel comprising: directly or indirectly linking apertures of the reaction vessels and the linking portions; and at the time of performing temperature control within the reaction vessels, according to temperature control by a temperature controller, which has a temperature source provided making contact with or approaching lower side wall sections of the reaction vessels, heating upper side wall sections of the reaction vessels, which are positioned further on an upper side than the lower side wall sections, by means of a heat source of a heating portion, which is provided making contact with or approaching the upper side wall sections, and thereby preventing direct or indirect condensation of the linking portions.

A twenty-third aspect of the invention is a light measurement method for a reaction vessel comprising: detachably mounting dispensing tips on respective nozzles, which are provided to a nozzle head and perform the suction and the discharge of gases; separating a target compound by using a magnetic force part, a nozzle head transfer mechanism that relatively moves an interval between the nozzle head and a vessel group, a magnetic particle suspension housed within a vessel group, in which magnetic particles that are able to capture a target compound are suspended, a sample, and a solution for separating and extracting of a target compound; introducing the separated target compound and a reaction solution used for reactions to a plurality of reaction vessels provided to a vessel group; moving a light guide stage, which has two or more linking portions that are provided to the nozzle head and in which front ends of one or two or more light guide portions are also provided, with respect to apertures of the reaction vessels by means of, at the very least, the nozzle head transfer mechanism; directly or indirectly simultaneously linking the respective apertures of the reaction vessels and the linking portions, and optically connecting the interior of the reaction vessels and the light guide portions that are linked; performing temperature control within the reaction vessels; guiding light from the reaction vessels to a connecting end arranging body that arranges and supports along a predetermined path two or more connecting ends, to which back ends of the light guide portions, in which front ends thereof are provided to the linking portions, are provided, the connecting ends are provided corresponding to the respective linking portions; and successively optically connecting one or two or more measuring ends that are provided to a measurement device, and provided approaching or making contact with an arranging surface, and the connecting ends, along the predetermined path by relatively moving them, to thereby make the respective measurement devices receive the light based on an optical state within the reaction vessels.

It is possible to respectively combine the second aspect of the invention through to the fifteenth aspect of the invention with the present aspect of the invention.

Furthermore, in a case where the measurement device comprises a plurality of types of measurement devices, it is preferable at the time the light from the reaction vessels is guided to the connecting end arranging body, at the very least between adjacent measurement devices, for the intensity of the light to be received by the respective measurement devices to be modulated at mutually different predetermined frequencies, and with regard to the light received by the respective measurement devices, for tuning to be performed to the predetermined frequencies, and for the corresponding intensity of the received light to be obtained.

According to the first aspect of the invention, the sixteenth aspect of the invention, the seventeenth aspect of the invention, or the twenty-third aspect of the invention, as a result of linking with the plurality of reaction vessels by means of the linking portions provided to the light guide stage and optically connecting with the interior of the reaction vessels, the optical state within the reaction vessels is transmitted via the plurality of reaction vessels, the light guide stage, and the light guide portion, to the connecting ends of the arranging surface of the connecting end arranging body, and the connecting ends arranged along the predetermined path on the arranging surface of the connecting end arranging body and the measuring ends of the measuring device are successively optically connected. Therefore, compared to a case where the measuring ends are directly scanned with respect to the apertures of the reaction vessels, then in addition to preventing the attenuation or the leakage of light from the scattering of light at the interval between the measuring ends and the liquid surface, the arrangement of the connecting ends is such that it can be rearranged in order to perform the connection with the measuring ends rapidly and smoothly, and with certainty. Therefore, measurements with a high reliability, and more efficient and rapid measurements of the optical state within the reaction vessels, can be performed.

Consequently, with consideration of the stable light receivable time, the structure of the measuring ends, and the like, then the arranging region of the connecting ends as a whole, or the distance between adjacent connecting ends can be achieved by integration that makes the arranging region or the adjacent distances of the linking portions smaller, and, in comparison to the arrangement of the linking portion, by the smoothing of the movement of the measuring ends as a result of the linearization or the expansion of the radius of curvature of the predetermined path.

Switching of the optical system is performed by means of the movement between the measuring ends and the connecting ends on the arranging surface along the predetermined path. Therefore, the structure of the optical system can be simplified. Furthermore, by separating the connecting ends, the measuring ends, and the measurement device from the reaction vessels or the light guide stage, in which temperature control or heating control is performed, thermal effects on the optical system elements are excluded, and processing with a high reliability can be performed.

The movement of the connecting ends with respect to the measuring ends includes continuous or intermittent movement. As a result of the measurement by real-time PCR, an amplification curve is created, which can be utilized in various analyses, such as the determination of the initial concentration of DNA.

Moreover, since the measurement of the plurality of reaction vessels can be performed in parallel with a single measuring device by utilizing the stable light receivable time, the expansion of the scale of the apparatus is suppressed by reducing the number of measuring devices, and the manufacturing costs can be reduced. Further, since it is possible to measure, by successively moving the interval between the measuring ends and the connecting ends through the shortest distance along the predetermined path determined beforehand, the measurements can be performed in parallel by a simple mechanism of only a transfer mechanism.

In a case where the reactions and the measurements are performed by sealing the reaction vessels by directly or indirectly linking the apertures of the reaction vessels with the linking portions, automatic measurements with a high reliability in which cross-contaminations and the contamination of light can be prevented with certainty can be performed.

Furthermore, according to the first aspect of the invention, the sixteenth aspect of the invention, the seventeenth aspect of the invention, or the twenty-third aspect of the invention, in a case where with respect to a plurality of measurement devices, at the very least between adjacent measurement devices, the intensity of the light to be received by the respective measurement devices is modulated at mutually different predetermined frequencies, and the light intensity is demodulated from the received light, the measurement devices are such that optical cross-talk mainly due to the entry of excitation light from adjacent measurement devices is prevented, and optical measurements with a high reliability can be performed. Consequently, since the arrangement of the connecting ends can be integrated even further, compact and rapid measurements can be performed.

According to the second aspect of the invention, at the time of movement with respect to the connecting ends arranged on the connecting end arranging body and the measuring ends, the measurement device is immovable with respect to the reaction vessels and the light guide stage that is linked with the same. Therefore, at the time of a measurement, a load from an inertia force due to acceleration accompanying the movement, and the like, is not placed on the optical system elements or the electronic elements built into the measurement device body, displacements of the optical system elements and destruction of the electronic elements are prevented, and an accurate measurement with a high reliability can be performed. In cases other than a measurement, the measurement device body is movable with respect to the reaction vessels and the like. Therefore, it is possible to transport the measurement device close to the reaction vessels and perform a measurement.

According to the third aspect of the invention, in the case where the light based on the optical state is a fluorescent light, the respective specific wavelength measurement devices are provided with irradiation sources of excitation light. Therefore, as the power source for the irradiation sources of the excitation light, an alternating current voltage of the predetermined frequency is applied, and excitation light that changes the intensity of light at the predetermined frequency can be easily obtained. By so doing, fluorescent light having an intensity corresponding to the irradiation of the excitation light, and that changes at the same frequency can be easily obtained. As a result, it becomes possible to perform highly reliable measurement without cross talk of light between adjacent measuring devices, with a simple configuration.

According to the fourth aspect of the invention, the sixteenth aspect of the invention, or the twenty-third aspect of the invention, by providing a stage transfer mechanism that moves the light guide stage, it is possible to simultaneously directly or indirectly link the linking portions with the reaction vessels without human intervention. Therefore, cross-contamination is prevented, and processing can be efficiently performed.

According to the third aspect of the invention or the eighteenth aspect of the invention, by using a plurality of types of luminescent compounds, colored compounds, color changing compounds, or light variation compounds, within a single reaction vessel, then for example in a case where amplification processing is performed in parallel under the same conditions on a plurality of types of amplification subjects, it is possible to perform multiplex PCR amplification or multiplex real-time PCR on a plurality of types of amplification subjects by using a primer labeled with a plurality of types of luminescent compounds and the like. At that time, by combining the switching of the receiving of the light of a plurality of types of specific wavelengths or specific wavelength bands from the plurality of types of luminescent compounds and the like, with a mechanism utilizing the stable light receivable time that is used at the time of movement between the plurality of reaction vessels, it is not necessary to separately provide a special light switching mechanism, and the apparatus mechanism can be simplified and manufacturing costs can be reduced. Furthermore, since the respective specific wavelength measuring devices each receive light of a specific wavelength or a specific wavelength band, the effects of other specific wavelengths or specific wavelength bands are not received, and high-accuracy measurements can be performed. Moreover, since the respective specific wavelength measuring devices are each modularized such that removal and addition can be performed, processing with a high versatility according to the processing aims can be performed.

According to the fifth aspect of the invention or the nineteenth aspect of the invention, by mounting the sealing lids arranged in the vessel group to the linking portions or the nozzles, it is possible to perform mounting to the apertures of the reaction vessels by means of movement of the nozzle head and the like. Therefore the housed substances within the reaction vessels do not make direct contact with the linking portions of the stage, and hence cross-contaminations can be effectively prevented. Furthermore, since it is not necessary to provide a dedicated mechanism for mounting the sealing lids on the reaction vessels, the scale of the apparatus is not expanded, and the manufacturing costs are reduced.

According to the twentieth aspect of the invention, the sealing of the reaction vessels can be performed with certainty by controlling the sealing lids covering the apertures of the reaction vessels such that they are pressed. Furthermore, by shaking the sealing lids, the sealed state between the apertures of the reaction vessels and the sealing lids can be rapidly and easily removed and released. Therefore, a high processing efficiency and reliability can be obtained.

According to the sixth aspect of the invention or the twenty-first aspect of the invention, by performing control such that the linking portions are heated, condensation at the time of temperature control of the reaction vessels that are sealed by the sealing lids is prevented, and measurements via the sealing lids, which have transparency, can be performed with certainty and a high accuracy.

According to the seventh aspect of the invention or the twenty-second aspect of the invention, by performing heating of the upper side wall sections of the reaction vessels according to the temperature control of the lower side wall sections of the reaction vessels, the direct or indirect condensation of the linking portions can be prevented. In this case, the linking portions and the sealing lids are not directly heated, and heating is performed at the upper side wall sections of the reaction vessels. Therefore, the effects of direct heating toward the optical system elements provided to the linking portions can be reduced or removed. Consequently, in addition to reducing or removing image distortions and the like due to the degradation or the change in properties of the optical system elements, various optical system elements can be provided to the linking portions. Therefore, precise measurements with a high versatility can be performed. Furthermore, it is not necessary to provide a heating portion directly above the vessels, and the structure directly above the vessels, and therefore the structure of the apparatus as a whole is simplified, and it is possible to further approach the linking portions possessing optical system elements, to the vessels and to perform the optical measurements with certainty. With respect to the lower side wall sections, according to the heating of the upper side wall sections, temperature control is performed such that the temperatures are guided to the respective predetermined temperatures set using a coolable Peltier element and the like, and measurements with a high reliability can be performed.

According to the eighth aspect of the invention, by using a material for the linking portion that is usable to a temperature higher than the dew point of water vapor, has a low thermal conductivity, and a high rigidity, prevention of condensation is achieved. Furthermore, the effects of heat toward the optical elements provided to the linking portion are reduced, and optical processing with a high reliability can be performed.

According to the ninth aspect of the invention, the thirteenth aspect of the invention, or the sixteenth aspect of the invention, as a result of the light guide stage being built into the nozzle head to which the nozzles are provided, a transfer mechanism (at the very least for the X axis and Y axis directions) between the reaction vessels of the measuring device is not separately provided, and since it can be combined with the transfer mechanism of the nozzles, the expansion of the scale of the apparatus can be prevented. Furthermore, since the transfer to the reaction vessel of the sample solution, the reagent solutions, and the reaction solutions, which are to be housed within the reaction vessels, and which represent the measurement subject, and the preparation, can be performed using the functions of the nozzles, steps from the processing to the measurement of the measurement subject can be consistently, efficiently, and rapidly performed.

According to the tenth aspect of the invention, since the sealing lids are transferred by being mounted on the nozzles, a new, dedicated lid transfer mechanism is not provided, and the expansion of the apparatus scale can be prevented by using existing mechanisms. On the other hand, in a case where the sealing lids are transferred or retained by being mounted on the linking portions, it is possible to make the diameters of the linking portions and the nozzles different. Therefore, it becomes possible to provide various optical system elements within the linking portions that are not limited by the size of the nozzles, and processing with a high versatility and with reliability can be performed.

According to the eleventh aspect of the invention, by providing the front end of a light guide portion bundle comprising a plurality of light guide portions to the linking portions, dividing the light guide portion bundle into a plurality of bundles, and separating the back end of the light guide portions to a plurality of connecting ends, and by simultaneously connecting with a plurality of measuring ends having one or a plurality of measurement devices, the receiving of light of a plurality of types of wavelengths or wavelength bands, or the irradiation of excitation light with respect to the reaction vessels and the receiving of light can be simultaneously performed. Therefore, processing of multiple fluorescent lights can be performed.

According to the twelfth aspect of the invention, the first measuring ends optically connect with the irradiation source of the measurement device, and the second measuring ends optically connect with the light receiving portion of the measurement device, and in addition, the ends of the light guide portions that are connectable with the irradiation source and the light receiving portion are mixed. Therefore, at the time of a measurement of fluorescent light, it is possible to irradiate excitation light within the reaction vessel without unevenness, and to measure the strength corresponding to the amount of fluorescence with certainty.

According to the fourteenth aspect of the invention, by providing traversable nozzles that are movable such that they traverse the respective exclusive regions, and dispensing target compounds or samples of the same nucleic acids and the like with respect to a plurality of exclusive regions, the same target compounds or samples can be utilized in reactions in which the conditions are changed. Furthermore, by combining the movement of the traversable nozzles with the transfer mechanism of the connecting end arranging body, the expansion of the apparatus scale can be suppressed.

According to the fifteenth aspect of the invention, by displaying information at the respective exclusive regions, and together with the movement of the traversable nozzles, reading in the information displayed at the respective exclusive regions with a camera, reaction and measurement processing with a high reliability can be performed without expanding the apparatus scale.

BEST MODE FOR CARRYING OUT THE INVENTION

Next, an embodiment of the present invention is described with reference to the drawings. This embodiment is not to be interpreted as limiting the present invention unless particularly specified. Furthermore, in the embodiments or in the exemplary embodiments, the same objects are denoted by the same reference symbols, and the descriptions are omitted.

Figure 1:
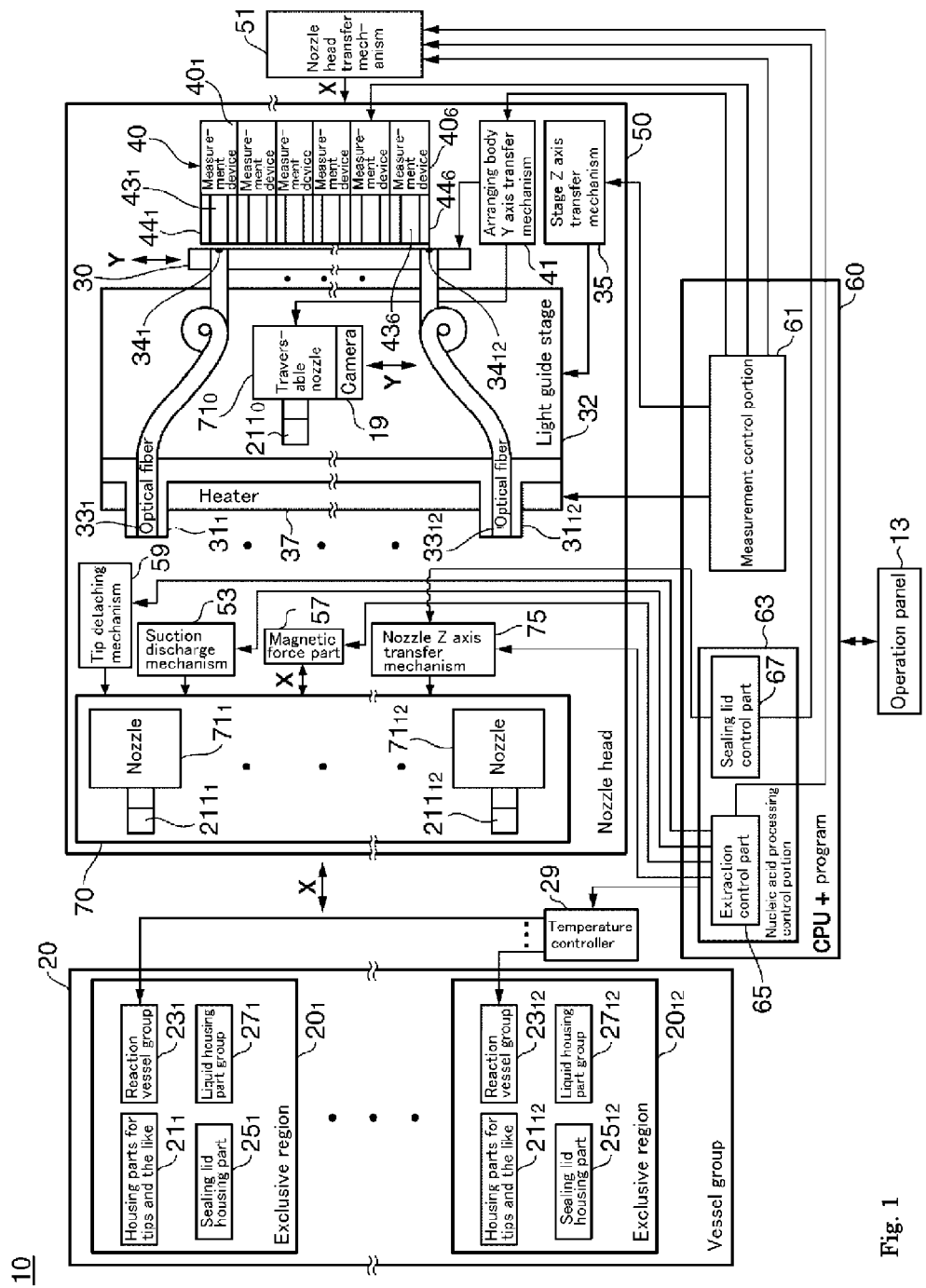
FIG. 1 is an overall block-diagram showing a light measurement apparatus for a reaction vessel according to a first embodiment of the present invention.

FIG. 1 is shows a block-diagram of a light measurement apparatus for a reaction vessel 10 according to a first embodiment of the present invention.

The light measurement apparatus for a reaction vessel 10 broadly has: a vessel group 20 in which a plurality (twelve in this example) of reaction vessel groups $23_i$ (i=1, ..., 12, omitted hereunder) are arranged; a nozzle head 50 that has a nozzle arrangement portion 70 in which a plurality (twelve in this example) of nozzles $71_i$ that detachably mount dispensing tips are arranged, and a light guide stage 32 that has a plurality (twelve in this example) of linking portions $31_i$ provided with the ends of two or more light guide portions, which have a flexibility, that are directly or indirectly linkable with the apertures of the reaction vessels and optically connect to the linked reaction vessel interior; a measurement device 40 that is provided fixed to the nozzle head 50; a nozzle head transfer mechanism 51 that makes the nozzle head 50 movable in the X axis direction for example; a temperature controller 29 that performs predetermined temperature control with respect to the reaction vessel group $23_i$ of the vessel group; a CPU+program 60 composed of a CPU, a ROM, a RAM, various types of external memory, communication functions such as a LAN, and a program stored in the ROM, and the like; and a control panel 13 having a display portion such as a liquid crystal display, and an operation portion, such as operation keys or a touch panel.

The nozzle head 50 has: a stage Z axis transfer mechanism 35 that makes the light guide stage 32 movable in the Z axis direction with respect to the vessel group 20 independent of the nozzle arrangement portion 70; a nozzle Z axis transfer mechanism 75 that makes the nozzle arrangement portion 70 movable in the Z axis direction with respect to the vessel group 20 independent of the stage 30; a magnetic force part 57 that, by means of a magnet 571 provided on a narrow diameter portion $211ia$ of a dispensing tip $211i$ detachably mounted on the nozzle $71i$ such that it can approach and separate, is able to apply and remove a magnetic field with respect to the interior; a suction-discharge mechanism 53 that makes the suction and the discharge of liquids with respect to the dispensing tip $211i$ mounted on the nozzle $71i$ possible by performing the suction and the discharge of gases with respect to the nozzle $71i$; and a punching mechanism 55 which is driven by the suction-discharge mechanism 53, for punching a film that covers the apertures of the liquid housing parts of the vessel group 20 to seal various liquids in advance. The stage transfer mechanism corresponds to the nozzle head transfer mechanism and the stage Z axis transfer mechanism.

The nozzle head 50 further has a connecting end arranging body 30 that arranges and supports a plurality (twelve in this example) of connecting ends $34_i$, which are provided corresponding to the respective linking portions $31_i$ and are provided with the back ends of optical fibers (bundle) $33_i$, which represent light guide portions in which the front ends thereof are provided to the linking portions $31_i$, such that, as an arranging surface, they are integrated along a predetermined path (a linear path along the Y axis direction in this example) provided on a vertical plane at a narrower spacing than the spacing between the linking portions $31_i$. Furthermore, the connecting end arranging body 30 is provided at a position that is separated from the light guide stage 32 and the reaction vessel group $23_i$.

The measurement device 40 is able to respectively receive the light of specific wavelengths or specific wavelength bands of six types of fluorescent light, and also has six types of specific wavelength measurement devices $40_j$ (j=1, ..., 6, omitted hereunder) that are able to irradiate excitation light of six types of specific wavelengths or specific wavelength bands that are irradiated for the emission of light.

The respective specific wavelength measurement devices $40_j$ have measuring ends $44_j$ that are provided approaching or making contact with the arrangement surface, and are successively connectable with the respective connecting ends $34_i$ along the predetermined path (a linear path along the Y axis direction). Furthermore, the respective measuring ends $44_j$ have two ends, namely a first measuring end $42_j$ and a second measuring end $43_j$ arranged along the Y axis direction. The first measuring ends $42_j$ optically connect with an irradiation source provided to the specific wavelength measurement devices $40_j$. The second measuring ends $43_j$ optically connect with a photoelectric device, such as a photomultiplier tube, provided to the specific wavelength measurement devices $40_j$.

Furthermore, the nozzle head 50 has an arranging body Y axis transfer mechanism 41, which represents a light guide switching mechanism, that moves the connecting end arranging body 30 along the Y axis direction on the nozzle head 50 such that the respective connecting ends $34_i$ arranged on the connecting end arranging body 30 and the respective measuring ends $44_j$ are successively connected.

Moreover, the light guide stage 32 has a heater 37, which represents the heating portion, for preventing condensation of the ends of the linking portions $31_i$ or the mounted sealing lids $251_i$, which have transparency, by heating.

The vessel group 20 comprises a plurality (twelve in this example) of exclusive regions $20_i$, in which one (in this example, one group corresponds to one) nozzle enters and the other nozzles do not enter, that correspond to the respective nozzles. The respective exclusive regions $20_i$ have: a liquid housing part group $27_i$ comprising a plurality of housing parts in which reagent solutions and the like are housed or are housable; a sealing lid housing part $25_i$ in which one or two or more sealing lids $251_i$, which have transparency, that are detachably mounted on the nozzles are housed or are housable; and housing parts for tips and the like $21_i$ that house, a plurality of dispensing tips $211_i$ that are detachably mounted on the nozzles, and the samples, and the like. The liquid housing part group $27_i$ has, at the very least, one or two or more liquid housing parts that house a magnetic particle suspension, and two or more liquid housing parts that house a solution for separating and extracting used for the separation and the extraction of nucleic acids or the fragments thereof If necessary, it further has two or more liquid housing parts that house a solution for amplification used for the amplification of nucleic acids, and a liquid housing part that houses a sealing liquid for sealing the solution for amplification housed in a PCR tube $231_i$, which represents the reaction vessel, within the PCR tube $231_i$.

It is preferable for the exclusive regions $20_i$ to display a barcode as the sample information and the inspection information for identifying the exclusive regions $20_i$. Furthermore, the nozzle head 50 is provided with a single traversable nozzle $71_0$ in which liquids are transportable or dispensable by traversing (moving in the Y axis direction) the exclusive regions $20_i$, and suction and discharge is made to be performed by a traversable nozzle suction-discharge mechanism 17 that is separate from the suction-discharge mechanism 53. Consequently, the solution of DNA and the like housed in a given exclusive region $20_i$ can be dispensed or delivered to the other exclusive regions $20_k$ ($k \neq i$). It is preferable for this movement in the Y axis direction to be also used by the arranging body Y axis transfer mechanism 41.

The CPU+program 60 has, at the very least: a nucleic acid processing control portion 63 that performs instructions for a series of processes, such as extraction and amplification with respect to nucleic acids or the fragments thereof, and sealing of the solution for amplification, with respect to the temperature controller 29, the nozzle head transfer mechanism 51, the tip detaching mechanism 59, the suction-discharge mechanism 53, the magnetic force part 57, and the nozzle Z axis transfer mechanism 75; and a measurement control portion 61 that, after the nozzle head transfer mechanism 51 and the stage Z axis transfer mechanism 35 are controlled such that the linking portions $31_i$ are simultaneously directly or indirectly linked with the apertures of the plurality (twelve in this example) of PCR tubes $231_i$, instructs a measurement by the measurement devices $40_j$ by controlling the arranging body Y axis transfer mechanism 41 such that the optical fibers (bundle) $33_i$, which represent the light guide portions of the linking portions $31_i$, and the first measuring ends $42_j$ and the second measuring ends $43_j$ of the measuring ends $44_j$ of the measurement devices $40_j$ mentioned below are optically connected.

Furthermore, the nucleic acid processing control portion 63 has an extraction control part 65 and a sealing lid control part 67. The nucleic acid processing control portion 63 has the extraction control part 65 that performs instructions with respect to the tip detaching mechanism 59, the suction-discharge mechanism 53, the magnetic force part 57, the nozzle Z axis transfer mechanism 75, the nozzle head transfer mechanism 51, and the stage Z axis transfer mechanism 35, for a series of processes with respect to the nucleic acids or the fragments thereof, and the sealing lid control part 67 that performs instructions with respect to the stage Z axis transfer mechanism 35 and the nozzle head transfer mechanism 51 for a sealing process by the sealing lids.

Figure 2:
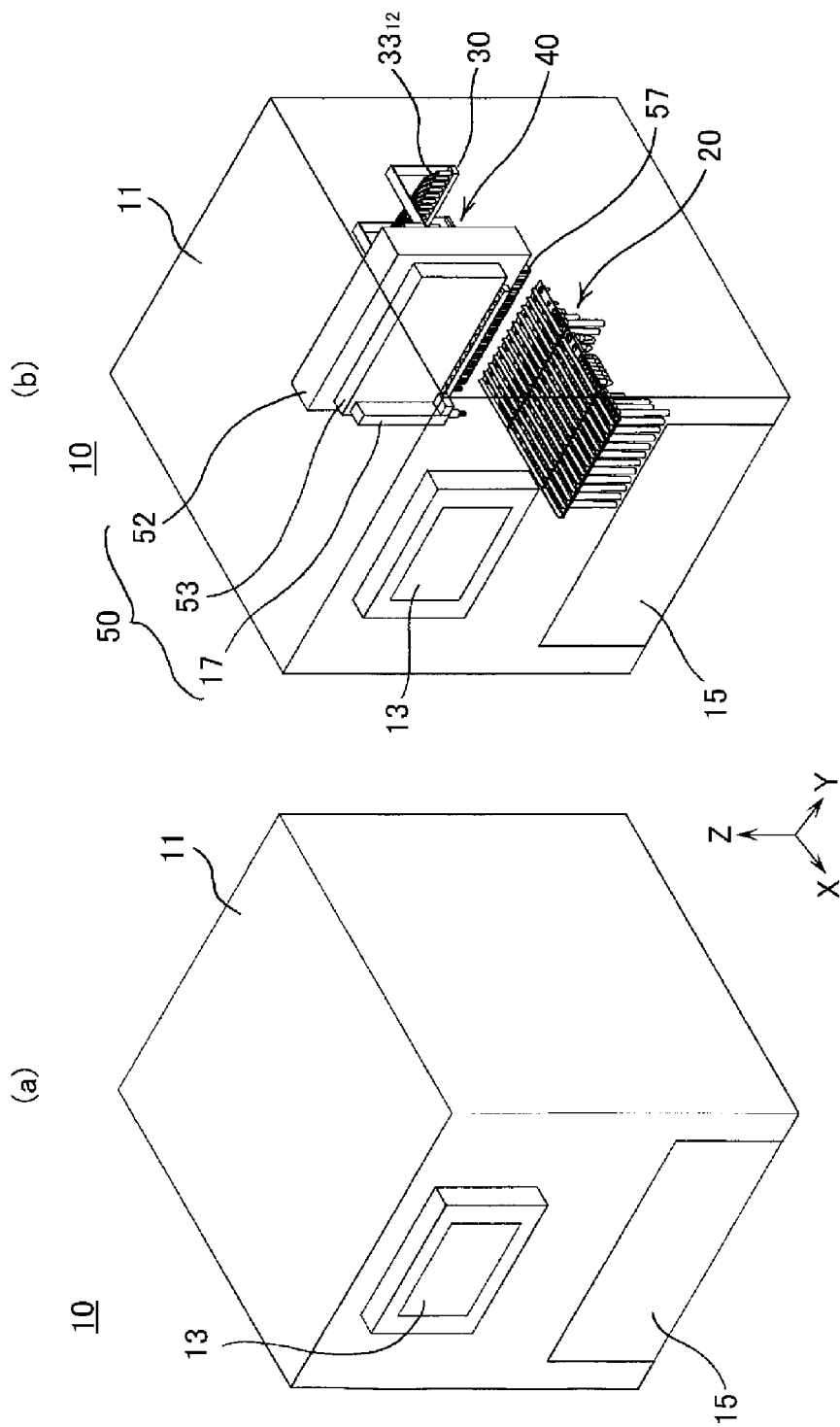
FIG. 2 is an overall perspective view showing the light measurement apparatus for a reaction vessel according to a first exemplary embodiment.

Hereunder, a more specific first embodiment of the light measurement apparatus for a reaction vessel 10 mentioned above according to an embodiment of the present invention, is described with reference to FIG. 2 to FIG. 10. FIG. 2 is a see-through perspective view showing an external view of the light measurement apparatus for a reaction vessel 10 according to the first embodiment of the present invention.

FIG. 2A is a drawing showing an external view of the light measurement apparatus for a reaction vessel 10, which has: an enclosure 11 with a size of 500 mm in depth (Y axis direction), 600 mm in width (X axis direction), and 600 mm in height (Z axis direction) for example, in which the vessel group 20, the nozzle head a nozzle head transfer mechanism 51 described in FIG. 1, and a CPU+program 60 are housed in the interior; a control panel 13 provided on the enclosure 11; and a drawer 15 to which a stage is provided.

FIG. 2B is a perspective view that sees through the interior of the enclosure 11, wherein the stage, into which the vessel group 20 is built-in, is able to be drawn out to the exterior by means of the drawer 15, and further, the nozzle head 50 is movably provided in the X axis direction with respect to the vessel group 20 by means of the nozzle head transfer mechanism 51 of FIG. 1.

FIG. 2B is a drawing showing that the nozzle head 50 is largely provided with: various transfer mechanisms 52 having an arranging body Y axis transfer mechanism 41, a stage Z axis transfer mechanism 35, and a nozzle Z axis transfer mechanism 75; a traversable nozzle suction-discharge mechanism 17; the measuring device 40; a connecting end arranging body 30; an optical fiber (bundle) $33_i$; and the magnetic force part 57. The traversable nozzle suction-discharge mechanism 17 and the traversable nozzles $71_0$ are supported such that they are movable in the Y axis direction by means of the arranging body Y axis transfer mechanism 41 such that they traverse the exclusive regions $20_i$.

Figure 3:
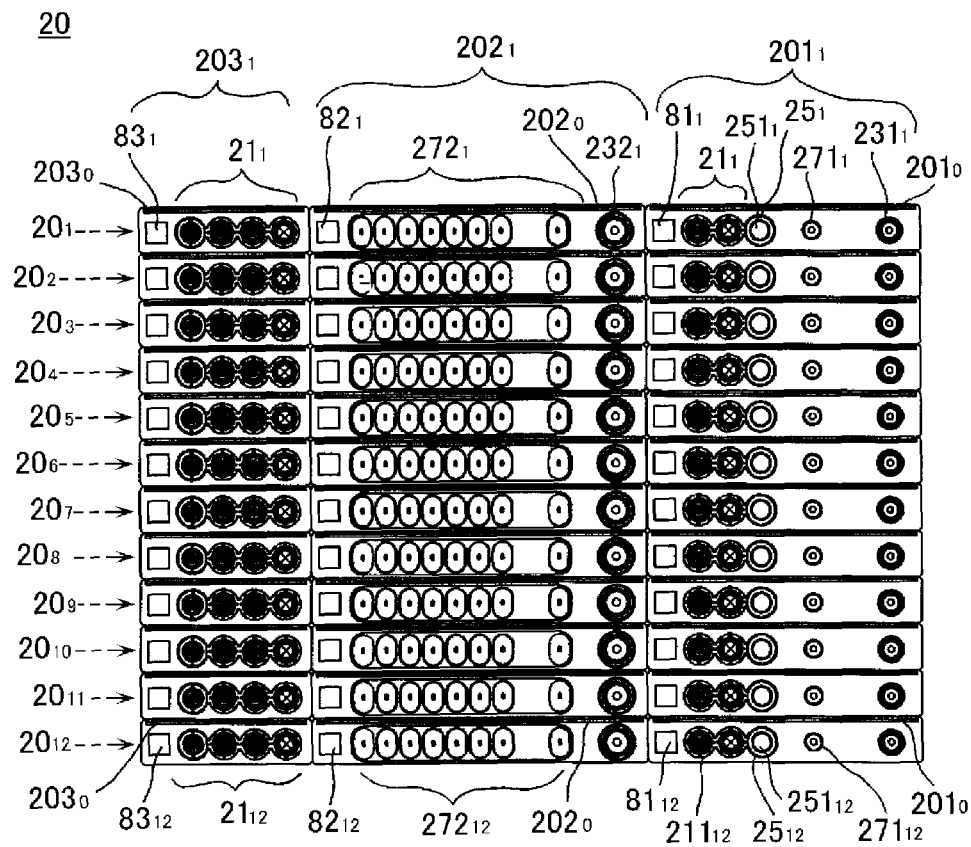
FIG. 3 is a plan view showing enlarged, a vessel group of the light measurement apparatus for a reaction vessel shown in FIG. 2.
Figure 3:
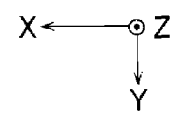

FIG. 3 is a plan view showing enlarged, the vessel group 20 shown in FIG. 2. The vessel group 20 is one in which twelve exclusive regions $20i$ ($i=1, \ldots, 12$), wherein the longitudinal direction thereof is along the X axis direction and housing parts are arranged in a single row form, are arranged in parallel along the Y axis direction at a pitch of 18 mm for example. The exclusive regions $20_i$ are separately provided with a cartridge vessel for PCR amplification $201_i$, a cartridge vessel for nucleic acid extraction $202_i$, and a cartridge vessel for housing tips $203_i$. The prevention of cross-contaminations between the exclusive regions $20_i$ is achieved by providing partition walls $201_0$, $202_0$, and $203_0$ on the cartridge vessels $201_i$, $202_i$, and $203_i$ of the exclusive regions $20_i$ on the edge of one side along the X axis direction.

The cartridge vessel for PCR amplification $201_1$ has: the PCR tubes $231_1$, which represent the reaction vessel that are detachably linked with the twelve linking portions $31_i$ provided to the light guide stage 32, via a single sealing lid $251_i$ which has transparency; the liquid housing parts $271_i$ which house a buffer solution necessary for the PCR reaction; the sealing lid housing parts $25_i$ which house the sealing lids $251_i$; the housing part for tips and the like $21_i$ that house the tips for punching for punching the film covering the PCR tubes $231_i$ and the liquid housing parts $271_i$, and the dispensing tips $211_i$, and barcodes $81_i$ that display the sample information and the inspection information relating to the cartridge vessels for PCR amplification $201_i$.

The cartridge vessels for nucleic acid extraction $202_i$ has: seven liquid housing parts $272_i$ for example, that house various reagents for nucleic acid extraction; reaction vessels $232_i$ that house the extracted nucleic acids; and barcodes $82_i$ that display various information, such as the sample information and the inspection information, related to the cartridge vessel. The PCR tubes $231_i$ and the reaction vessels $232_i$ are temperature controllable by means of the temperature controller 29.

The cartridge vessels for housing tips $203_i$ has: a tip for punching that is able to punch the film covering the cartridge vessel for nucleic acid extraction $202_i$; two small-quantity dispensing tips that perform the dispensing of small quantities of liquids; housing parts for tips and the like $21_i$ that house dispensing tips for separations that are able to perform separation by adsorbing magnetic particles on an inner wall by applying and removing a magnetic force from the exterior, and a barcode $83_i$ that displays various information relating to the cartridge vessel $203_i$.

The capacity of the PCR tube $231_i$, which represents the reaction vessel, is of the order of approximately 200 μL, and the capacity of the other reaction vessels, liquid housing parts, and tubes is of the order of approximately 2 mL.

Figure 9:
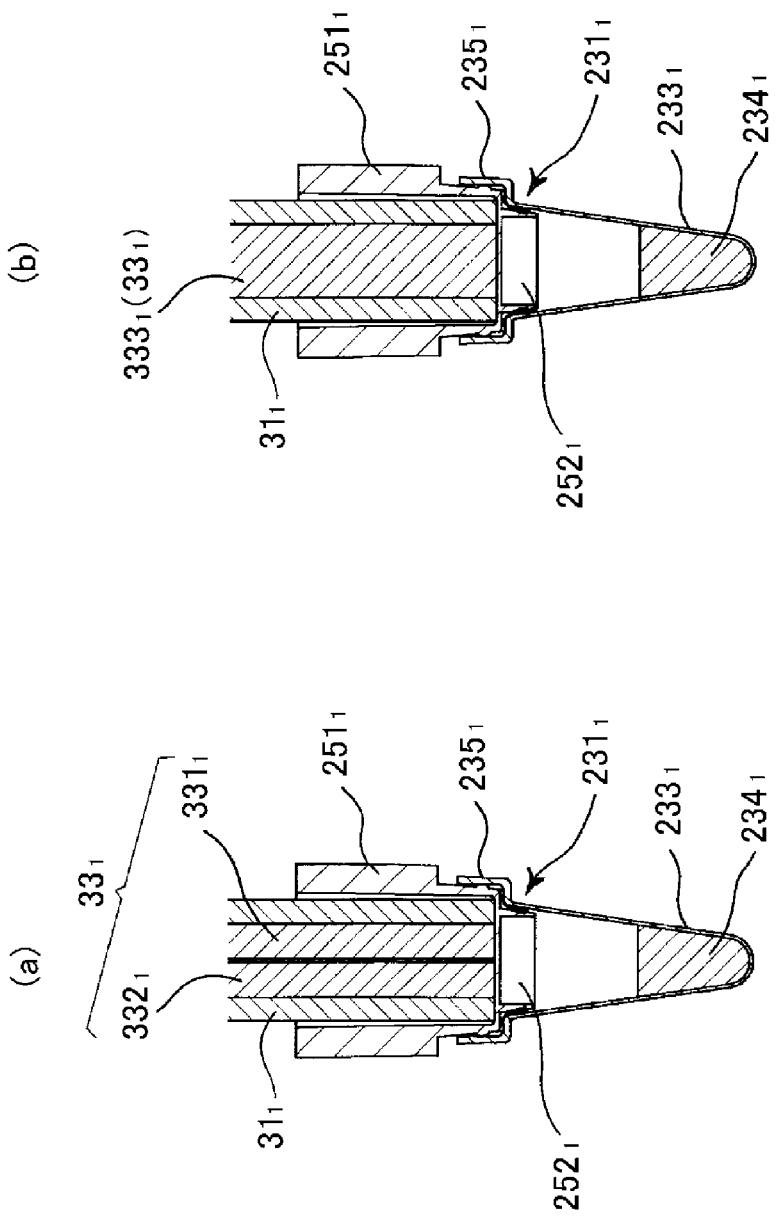
FIG. 9 is a cross-sectional view showing a state in which the linking portion shown in FIG. 4 is linked with a reaction vessel.

The PCR tube $231_i$ is used for the amplification of nucleic acids or the fragments thereof, and temperature control is performed by means of the temperature controller 29 based on a predetermined amplification method, such as a thermal cycle (from 4° C. to 95° C.) for example. The PCR tube $231_i$ is formed with two levels as shown in FIG. 9 for example, and has a narrow-mouthed piping part 233 provided on the lower side in which the solution for amplification $234_i$ is housed, and a wide-mouthed piping part $235_i$ provided on the upper side in which the sealing lid $251_i$ is fittable. The inner diameter of the wide-mouthed piping part $235_i$ is 8 mm for example, and the inner diameter of the aperture of the narrow-mouthed piping part $233_i$ is approximately 5 mm for example. The reaction vessels $232_i$ housed in the reaction tube housing holes are temperature controlled for incubation to a constant temperature of 55° C. for example.

The liquid housing part group $272_i$ houses the solutions for separating and extracting as follows. A first liquid housing part houses 40 μL of Lysis 1, a second liquid housing part houses 200 μL of Lysis 2, a third liquid housing part houses 500 μL of a binding buffer solution, a fourth liquid housing part houses a magnetic particle suspension, a fifth liquid housing part houses 700 μL of a washing liquid 1, a sixth liquid housing part houses 700 μL of a washing liquid 2, a seventh liquid housing part houses 50 μL of distilled water as a dissociation liquid, and an eighth liquid housing part, which is slightly separated, houses 1300 μL of isopropyl alcohol (isopropanol) used for the removal of protein and the like, as a portion of the solution for separating and extracting protein. The respective reagents and the like are prepacked as a result of the punchable film covering the respective apertures thereof.

In addition, 1.2 mL of distilled water is housed in a separate distilled water reservoir, and tubes that house suspensions of bacteria, cells, and the like, or samples such as whole blood, are separately prepared for each of the respective exclusive regions $20_i$.

Figure 4:
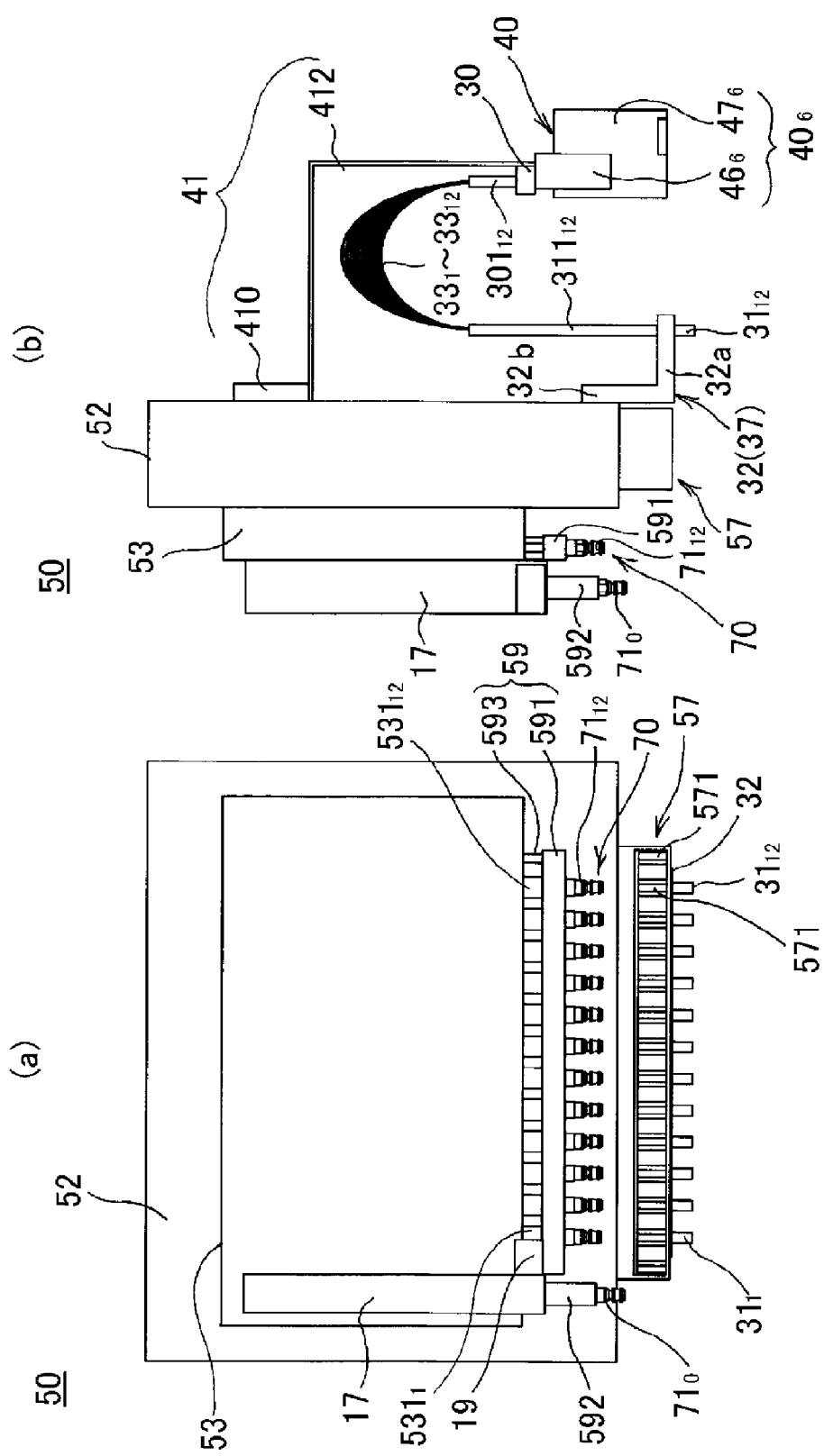
FIG. 4 is a front view and a side view showing enlarged, a nozzle head of the light measurement apparatus for a reaction vessel shown in FIG. 2.
Figure 5:
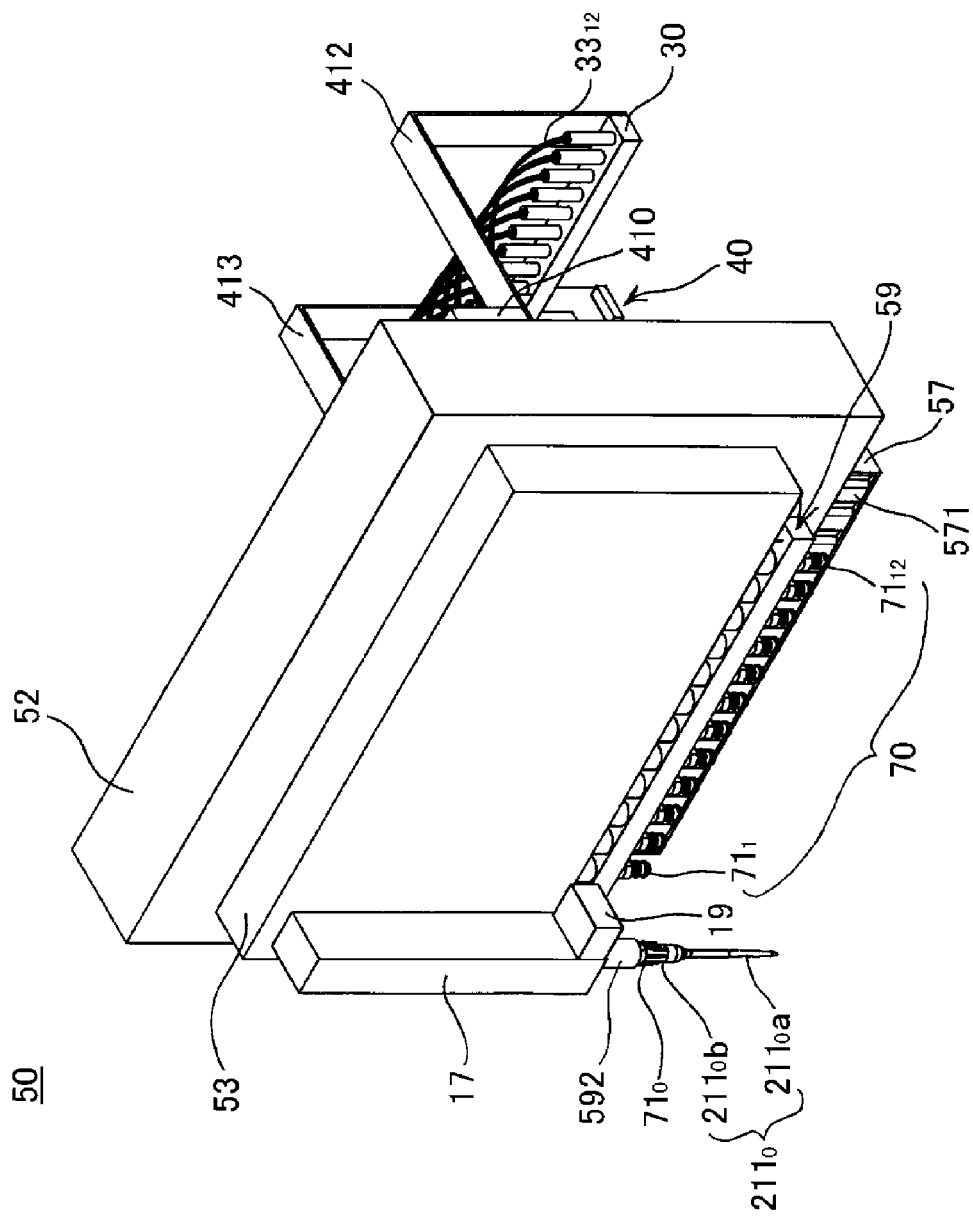
FIG. 5 is a perspective view as viewed from the front side of the nozzle head shown in FIG. 4.

FIG. 4 is a front view and a side view of the nozzle head 50 according to the first embodiment of the present invention, and FIG. 5 is a perspective view from the front side.

The nozzle head 50 is one having: a nozzle arranging portion 70 in which twelve nozzles $71_i$ are arranged; a tip detaching mechanism 59 that is able to detach dispensing tips $211_i$ mounted on the nozzles $71_i$; a suction-discharge mechanism 53; a magnetic force part 57 having twelve magnets 571 provided such that they are able to approach and separate with respect to the dispensing tips $211_i$; a light guide stage 32; twelve linking portions $31_i$ provided to the light guide stage 32; a transfer mechanism portion 52 having a nozzle Z axis transfer mechanism 75 and a stage Z axis transfer mechanism 35; optical fibers (bundles) $33_i$ representing flexible light guide portions that extend to the rear side from the linking portions $31_i$; a connecting end arranging body 30; the arranging body Y axis transfer mechanism 41; a measuring device 40 having a measuring end 44; a traversable nozzle $71_0$; and a suction-discharge mechanism 17 thereof.

The nozzle arranging portion 70 is provided with a cylinder supporting member 73 that supports twelve cylinders $531_i$ such that they are arranged along the Y axis direction at a predetermined pitch of 18 mm for example. The nozzles $71_i$ are provided on the downward end of the cylinders $531_i$ such that they are communicated with the cylinders $531_i$.

The tip detaching mechanism 59 is provided with detaching shafts 593 on both sides, and has a tip detaching member 591 that detaches the twelve dispensing tips $211_i$ from the nozzles $71_i$ by sliding in the vertical direction.

Figure 6:
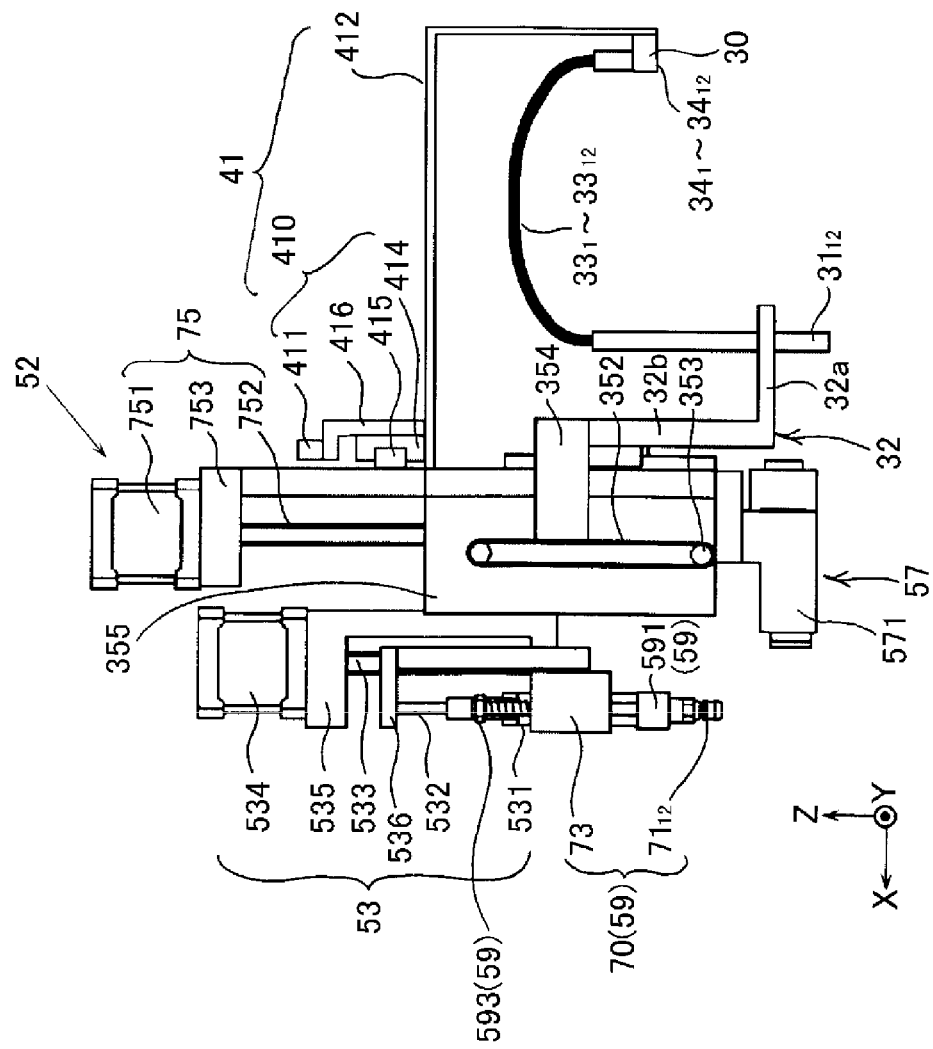
FIG. 6 is a side view showing more specifically, the transfer mechanisms and the suction-discharge mechanism shown in FIG. 4.
Figure 7:
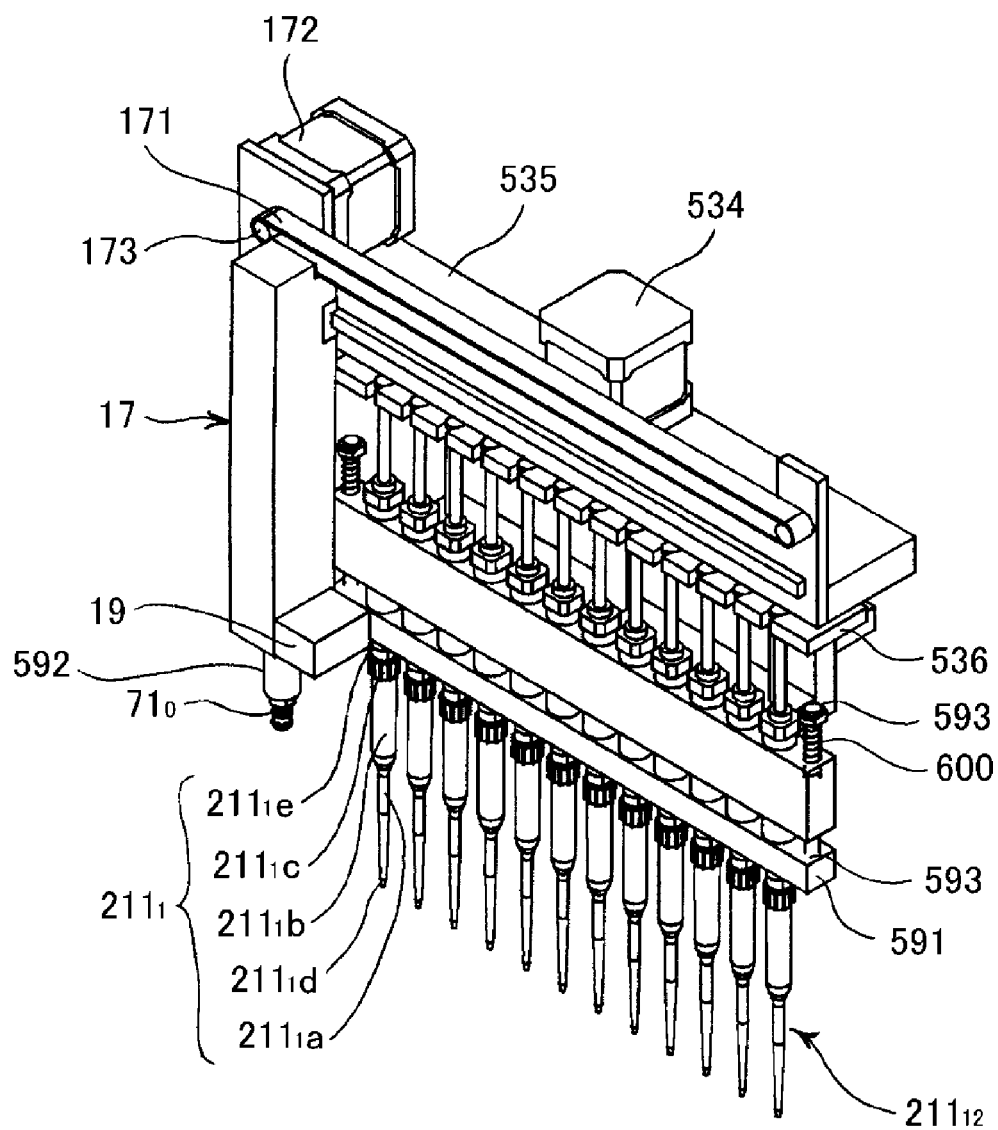
FIG. 7 is a perspective view showing more specifically, the suction-discharge mechanism 53 and the like shown in FIG. 4.

As shown specifically in FIG. 6 and FIG. 7, the tip detaching member 591 is interlocked with the lowering of two tip detaching shafts 593 and detaches the dispensing tips $211_i$ from the nozzles $71_i$. The tip detaching shaft 593 is elastically supported by the cylinder support member 73 by means of a spring 600 wrapped around the outer periphery such that it is biased in the upward direction, and the upper end thereof is positioned above the upper ends of the cylinders $531_i$ but below the lower limit position of the vertical movement range of the normal suction and discharge of a cylinder drive plate 536 mentioned below. The two tip detaching shafts 593 are pushed in the downward direction by means of the cylinder drive plate 536 exceeding the vertical movement range and being lowered near the upper end of the cylinder $531_i$, thus lowering the tip detaching member 591. The tip detaching member 591 has twelve holes having an inner diameter that is larger than the outer diameter of the nozzles $71_i$ but smaller than the mounting portions $211_ic$, which represents the largest outer diameter of the dispensing tips $211_i$, arranged at the pitch mentioned above such that the nozzles $71_i$ pass therethrough.

As shown specifically in FIG. 6 and FIG. 7, the suction-discharge mechanism 53 has: the cylinders $531_i$ for performing suction and discharge of gases with respect to the dispensing tips $211_i$ which are communicated with the nozzles $71_i$ and mounted on the nozzles $71_i$, and a piston rod 532 that slides within the cylinders $531_i$; a drive plate 536 that drives the piston rod 532; a ball screw 533 that threads with the drive plate 536; a nozzle Z axis movable body 535 that, in addition to axially supporting the ball screw 533, is integrally formed with the cylinder support member 73; and a motor 534 mounted on the nozzle Z axis movable body 535 that rotatingly drives the ball screw 533.

The magnetic force part 57 has a magnet 571 that is provided such that it can approach and separate with respect to the narrow diameter portions $211_i a$ of the dispensing tips $211_i$ detachably mounted on the nozzles $71_i$, and is able to apply and remove a magnetic field in the interior of the dispensing tips $211_i$.

As shown specifically in FIG. 6, the nozzle Z axis transfer mechanism 75 has: a ball screw 752 that threads with the Z axis movable body 535 and vertically moves the Z axis movable body 535 along the Z direction; a nozzle head substrate 753 that axially supports the ball screw 752, and in addition to axially supporting the magnet 571 on the lower side thereof such that it is movable in the X axis direction, is itself movable in the X axis direction by means of the nozzle head transfer mechanism 51 mentioned below; and a motor 751 provided on the upper side of the nozzle head substrate 753 that rotatingly drives the ball screw 752.

As shown specifically in FIG. 6, the light guide stage 32 comprises a horizontal plate 32a and a vertical plate 32b, which are letter-L shaped plates in cross-section, and is provided with twelve cylinder-shaped linking portions $31_i$ having front ends of optical fibers (bundles) $33_i$, which are directly or indirectly linkable with the apertures of the PCR tubes $231_i$ and are optically connected with the interior of the linked PCR tubes $231_i$, protruding in the downward direction from the horizontal plate 32a. Furthermore, a heater 37 that heats the sealing lids $251_i$ mounted on the linking portions $31_i$ and prevents condensation, is built into the bases of the linking portions $31_i$. The temperature of the heater is set to approximately 105° C. for example. Since the light guide stage 32 is supported by the nozzle head substrate 753 by means of the nozzle head stage Z axis transfer mechanism 35 such that it is movable in the Z axis direction, it is movable in the nozzle X axis direction and Z axis direction.

The stage Z axis transfer mechanism 35 has: a side plate 355 provided on the nozzle head substrate 753; a mount driving band-shaped member 354 that is supported by a timing belt 352 spanning between two sprockets 353 arranged in the vertical direction axially supported by the side plate 355, and vertically moves in the Z axis direction; and a motor attached to the rear side of the nozzle head substrate 753 that rotatingly drives the sprockets 353.

As shown in FIG. 7, the traversable nozzle suction-discharge mechanism 17 is provided with a tip detaching mechanism 592 on the lower side of the suction-discharge mechanism 17 and on the upper side of the nozzle $71_0$. Furthermore, the suction-discharge mechanism 17 is provided with a digital camera 19. The suction-discharge mechanism 17 is movably provided in the Y axis direction by being attached to a timing belt 171 spanning between two sprockets 173 that are rotatingly driven by a motor 172.

Figure 8:
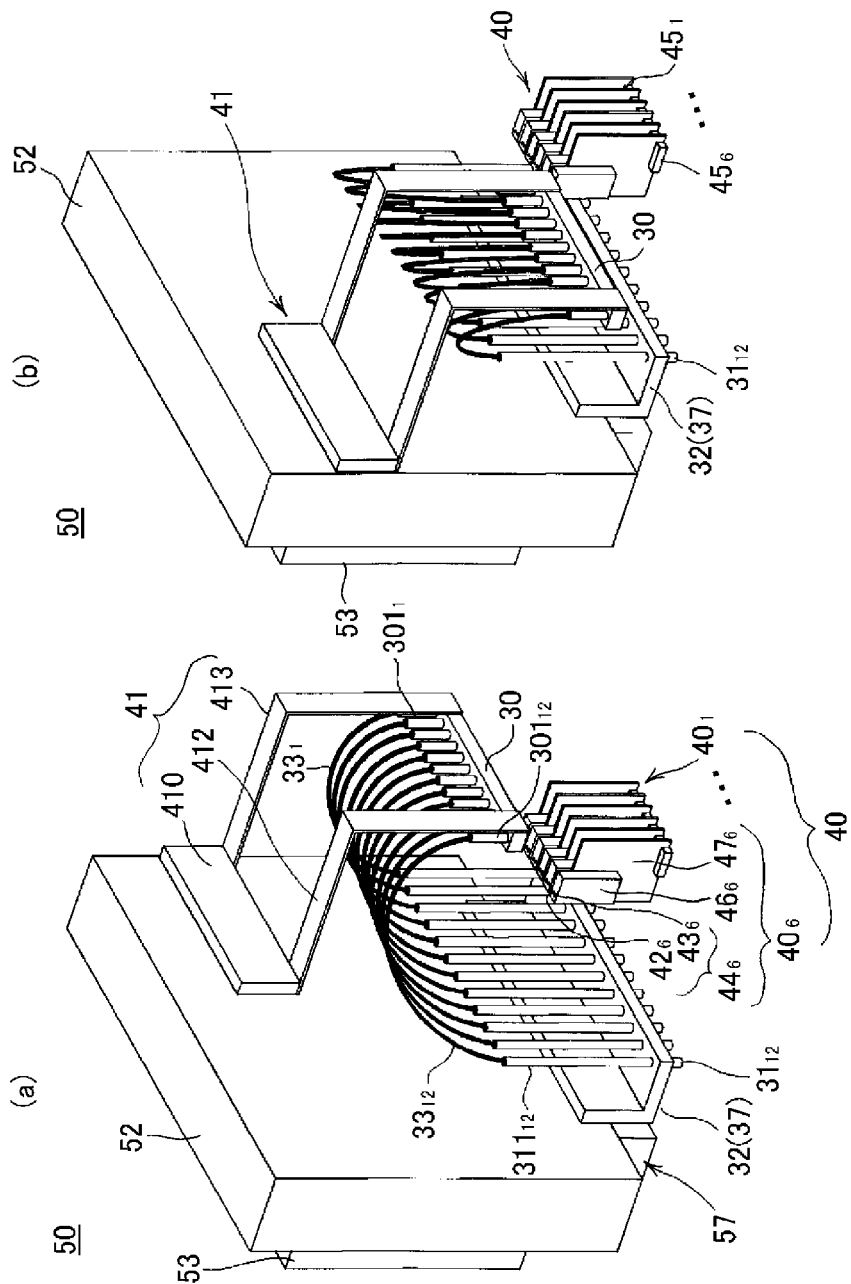
FIG. 8 is a perspective view as viewed from the rear side of the nozzle head shown in FIG. 4.

FIG. 8 represents two perspective views of the nozzle head according to the first embodiment viewed from the rear side, which show the connection starting position (FIG. 8A) and the connection finishing position (FIG. 8B) at the time the respective connecting ends of the connecting end arranging body 30 and the respective measuring ends are successively optically connected.

There are provided a connecting end arranging body 30 in which the connecting ends 34, provided corresponding to the respective linking portions 31, to which the front ends of the optical fibers (bundles) $33_i$ which pass through the horizontal plate 32a of the light guide stage 32, are provided, and provided with the back ends thereof, are arranged on an arranging surface on a path along a straight line in the Y axis direction, which represents a predetermined path, at a shorter spacing than the spacing of the linking portions $31_i$; and six measuring ends that are provided in the vicinity of, or making contact with, the arranging surface, and are successively optically connectable with the connecting ends $34_i$ along the straight line. There is also provided a measuring device 40 in which, by means of optical connections between the connecting ends and the measuring ends, the fluorescent light within the PCR tubes $231_i$, which represents the optical state, is receivable, and excitation light is also able to be irradiated.

Furthermore, the light guide stage 32 has a cylinder-shaped body $311_i$, which retains the optical fibers (bundles) $33_i$ extending to the rear side from the linking portions $31_i$ such that they pass through the interior in order to prevent folding, protrudingly provided upward from the horizontal plate 32a directly above the linking portions $31_i$. In the same manner, the connecting end arranging body 30 is also provided with a cylinder-shaped body $301_i$, which retains the optical fibers (bundles) $33_i$ extending from the connecting ends $34_i$ such that they pass through the interior in order to prevent folding, on the connecting end $34_i$ side.

The arranging body Y axis transfer mechanism 41 that moves the connecting end arranging body 30 in the Y axis direction has: arms 412 and 413 provided to the connecting end arranging body 30; a joining body 411 that joins the arms 412 and 413 and the timing belt; a guide rail 414 that guides the Y axis movement of the joining body 411; and two sprockets spanned by the timing belt and arranged along the Y axis direction.

The measuring device 40 is one that supports the measurement of fluorescent light and comprises six types of specific wavelength measuring devices $40_j$ that are linearly aligned along a straight line in the Y axis direction, which represents the predetermined path, such that they support the measurement of six types of fluorescent light, and they are provided fixed on a substrate of the nozzle head 50, such as the frame that encloses the transfer mechanism portion 52, or a member that supports the same. Therefore, depending on the mechanism provided to the transfer mechanism portion 52, the measuring device 40 does not move.

The measuring device 40 is one in which the measuring ends of the plurality of types (six in this example) of specific wavelength measuring devices $40_j$ (j=1, 2, 3, 4, 5, 6), and therefore, in this case, the specific wavelength measuring devices $40_j$ themselves are aligned in a single row form, and integrally fixed to a member joined with the nozzle head substrate 753 using fixtures $45_j$. The specific wavelength measuring devices $40_j$ have: measuring ends $44_j$ arranged along a straight line path in the Y axis direction which represents the predetermined path, such that they successively optically connect to the connecting ends $34_i$; light detectors $46_j$ in which an optical system component having an irradiation source that irradiates excitation light to the PCR tubes $231_i$ and a light receiving portion that receives the fluorescent light generated in the PCR tubes $231_i$ are built-in; and circuit boards $47_j$. The measuring ends $44_j$ have first measuring ends $42_j$ that optically connect with the irradiation source, and second measuring ends $43_j$ that optically connect with the light receiving portion. Here, the light detectors $46_j$ and the circuit boards $47_j$ correspond to the measuring device main body.

The pitch between the respective connecting ends $34_j$, assuming a pitch between the linking portions $31_i$ of 18 mm, is 9 mm, which is half thereof. Then, the pitch between the measuring ends $44_j$ is 9 mm or less for example.

There is a case where the first measuring ends $42_j$ and the second measuring ends $43_j$ of the measuring ends $44_j$ of the respective specific wavelength measuring devices $40j$ are arranged aligned in a lateral direction (Y axis direction) along the straight line of the Y axis direction along the predetermined path, and a case where they are arranged aligned in a longitudinal direction (X axis direction). In the former case, without stopping the emission of the excitation light, the respective measuring devices successively receive light at a timing for receiving light determined based on the speed of the connecting end arranging body, the pitch between the connecting ends, the distance between the first measuring ends and the second measuring ends of the measuring ends, and the pitch between the measuring ends.

On the other hand, in the latter case, as shown in FIG. 8, with respect to the connecting end, a first connecting end and a second connecting end are provided. The first connecting end connects only with the first measuring ends $42_j$, and the second measuring ends $43_j$ connect only with the second connecting end. The fixed path represents two paths. Furthermore, the optical fibers (bundles) $33_i$ have optical fibers (bundles) $331_i$ for receiving light that have the first connecting end, and optical fibers (bundles) $332_i$ for irradiation that have the second connecting end. In this case, compared to the former case, connection with the linking portions is performed by means of optical fibers in which the irradiation source and the light receiving portion are dedicated, and therefore, the control is simple, and the reliability is high since optical fibers that are respectively suitable for irradiation and receiving light can be used.

The speed of the connecting end arranging body 30 with respect to the measuring ends $44_j$ is determined with consideration of the stable light receivable time, the lifetime of the fluorescent light with respect to excitation light irradiation, the number of connecting ends, the pitch between the connecting ends, and the like (the distance of the predetermined path). In the case of a real-time PCR measurement, it is controlled such that it becomes 100 mm to 500 mm per second for example. In the present embodiment, since the movement is performed by sliding the arranging surface with respect to the measuring ends 44, the incidence of optical noise to the measuring ends 44 can be prevented. Furthermore, the connecting end arranging body 30 moves with respect to the measuring ends intermittently such that it momentarily stops at each pitch advance between the connecting ends or between the measuring ends, or continuously.

FIG. 9A is a drawing showing a state in which the linking portion $31i$ (here, i=1 for example) that protrudes on the lower side from the horizontal plate $32a$ of the light guide stage 32 is indirectly linked with the PCR tube $231i$ via the sealing lid $251i$, which has transparency, that is mounted on the aperture of the PCR tube $231i$ in the exclusive region $20i$, and the linking portion $31i$ is inserted within the indentation of the sealing lid $251i$, and the end surface thereof is adhered to the bottom surface of the indentation of the sealing lid $251i$. The PCR tube $231i$ comprises a wide-mouthed piping part $235i$ and a narrow-mouthed piping part $233i$ that is communicated with the wide-mouthed piping part $235i$ and is formed narrower than the wide-mouthed piping part $235i$. Furthermore, the narrow-mouthed piping part $233i$ is dried beforehand, or a liquid state solution for amplification $234i$ is housed beforehand. Here, the reagent for real-time amplification represents 70 μL, of a master mix (SYBR (registered trademark) Green Mix) consisting of enzymes, buffers, primers, and the like.

For the aperture of the wide-mouthed piping part $235i$, since the sealing lid $251i$ that protrudes on the lower side of the sealing lid $251i$, which has transparency, is mounted on the reaction vessel, it is mounted to the reaction vessel as a result of a tubular sealing portion $252i$, which encloses the center portion of the sealing lid $251i$ in which light passes through, being fitted. At the time the sealing portion $252i$ is fitted, it is preferable for the diameter of the optical fibers (bundle) $33i$, which represents the light guide portion that passes through the interior of the linking portion $31i$, to be the same or larger than the diameter of the aperture of the narrow-mouthed piping part $233i$. Consequently, it becomes possible to receive the light from the PCR tube $231i$ with certainty. The narrow-mouthed piping part $233i$ is housed within a block for temperature control that is heated or cooled by means of the temperature controller 29.

In this example, the optical fibers (bundle) $33i$ comprise optical fibers (bundle) for irradiation $332i$ that are connectable with the second measuring end $43j$ and optical fibers (bundle) for receiving light $331i$ that are connectable with the first measuring end $42j$.

FIG. 9B is a drawing showing an example in which the optical fibers (bundle) $33i$ comprise an optical fiber bundle in which an optical fiber bundle comprising a plurality of optical fibers for receiving light that are connectable with the second measuring end $43j$, and an optical fiber bundle comprising a plurality of optical fibers for irradiation that are connectable with the first measuring end $42j$, are combined such that they become uniform.

It is preferable for a feeding device for samples and the like to be integrated to the light measurement apparatus for a reaction vessel 10. The feeding device for samples and the like is a device for dispensing and supplying parent samples and the like with respect to the vessel group 20, and the stage in which is integrated the vessel group 20 to which the parent samples and the like have been supplied, is automatically moved to the light measurement apparatus for a reaction vessel and the like. The feeding device for samples and the like, for example, has a parent vessel group that houses parent samples and the like, a tip detaching mechanism, a suction-discharge mechanism, and a single nozzle that, in addition to the suction and the discharge of gases being performed by means of the mechanisms, is detachably mounted with dispensing tips $211i$. Furthermore, it has a nozzle head provided with a mechanism that moves along the Z axis direction with respect to the parent vessel group and the housing part group for tips and the like 21 of the vessel group 20, an X axis movable body provided with a Y axis transfer mechanism that moves the nozzle head in the Y axis direction with respect to the parent vessel group and the like, an X axis transfer mechanism that moves the X axis movable body along the X axis with respect to the parent vessel group and the like, and the parent vessel group. It is preferable for the parent vessel group to have a parent sample housing part group arranged in a 12 row×8 column matrix form that houses the parent samples to be supplied to the housing part group for tips and the like 21 of the vessel group 20, a distilled water and washing liquid group, and a reagent bottle group.

Figure 10:
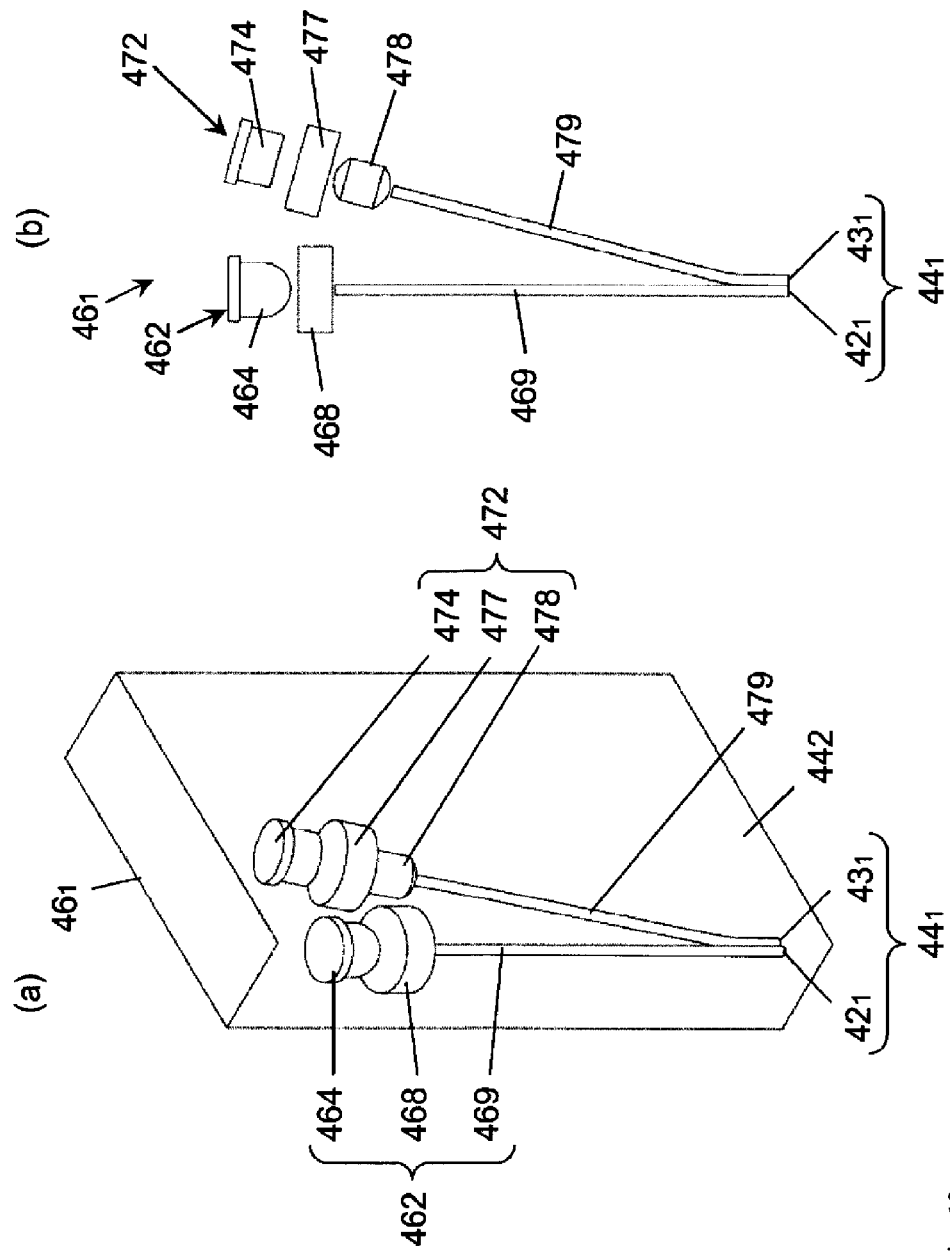
FIG. 10 is a drawing showing the specific wavelength measurement device shown in FIG. 4.

FIG. 10 is a drawing showing a light detector $46_1$ of a single specific wavelength measurement device $40_1$ belonging to the measurement device 40 according to a first exemplary embodiment of the present invention.

The specific wavelength measurement device $40_1$ according to the present exemplary embodiment, in addition to having an optical fiber 469 for excitation light to be outgoing to the PCR tube 231i and an optical fiber 479 for light from the PCR tube 231i to be incoming, has a measuring end 441 provided on the lower ends of a first measuring end 421 of the optical fiber 469 and a second measuring end 431 of the optical fiber 479, an irradiation portion 462 that has a LED 467 that irradiates excitation light through the optical fiber 469 and a filter 468, and a light receiving portion that has an optical fiber 479, a drum lens 478, a filter 477, and a photodiode 472. This example shows a case where the first measuring end 421 and the second measuring end 431 are provided along a direction (X axis direction) perpendicular to the straight line of the Y axis direction, which represents the predetermined path.

Next, a series of processing operations that perform real-time PCR of the nucleic acids of a sample containing bacteria using the light measurement apparatus for a reaction vessel 10 according to the embodiment is described. Step S1 to step S13 below correspond to separation and extraction processing.

In step S1, the drawer 15 of the light measurement apparatus for a reaction vessel 10 shown in FIG. 2 is opened, the vessel group 20 is pulled out, and by utilizing a feeding device for samples and the like, which is provided separately from the vessel group 20, the samples which are subject to testing, various washing liquids, and various reagents, are supplied beforehand, and furthermore, a liquid housing part in which reagents and the like are prepacked is mounted.

In step S2, following returning of the vessel group 20 and closing of the drawer 15, the start of the separation and extraction and amplification processing is instructed by means of the operation of the touch panel of the control panel 13 for example.

In step S3, the extraction control part 65 provided to the nucleic acid processing controller 63 of the CPU+program 60 of the light measurement apparatus for a reaction vessel 10 instructs the nozzle head transfer mechanism 51 and moves the nozzle head 50 in the X axis direction, positions the tip for punching mounted to the nozzle $71_i$ above the first liquid housing part of the liquid housing part group $27_i$ of the vessel group, and punches the film covering the aperture of the liquid housing part by lowering the nozzle by means of the nozzle Z axis transfer mechanism 75, and in the same manner, the other liquid housing parts of the liquid housing part group $27_i$ and the reaction vessel group $23_i$ are successively punched by moving the nozzle head 50 in the X axis direction.

In step S4, the nozzle head 50 is again moved in the X axis direction and moved to the housing part for tips and the like $21_i$, and the nozzles $71_i$ are lowered by means of the nozzle Z axis transfer mechanism 75, and the dispensing tips $211_i$ are mounted. Next, after being raised by the nozzle Z axis transfer mechanism 75, the dispensing tips $211_i$ are moved along the X axis by means of the nozzle head transfer mechanism 51, and advanced to the eighth liquid housing part of the liquid housing part group $27_i$. Then a predetermined amount of isopropanol is aspirated from the liquid housing part, and they are again moved along the X axis direction, and predetermined amounts are respectively dispensed into the solution components (NaCl, SDS solutions) housed in the third liquid housing part and the fifth liquid housing part, and the distilled water housed in the sixth liquid housing part, so that 500 μL of a binding buffer solution (NaCl, SDS, isopropanol), 700 μL of a washing liquid 1 (NaCl, SDS, isopropanol), and 700 μL of a washing liquid 2 (water 50%, isopropanol 50%) are respectively prepared as solutions for separating and extracting within the third, the fifth, and the sixth liquid housing parts.

In step S5, following movement to, among the housing parts for tips and the like $21_i$, the sample tube in which the sample is separately housed, the narrow diameter portion $211_i a$ of the dispensing tip $211_i$ is loweringly inserted using the nozzle Z axis transfer mechanism 75, and, with respect to the suspension of the sample housed in the sample tube, following suspension of the sample within the liquid by repeating the suction and the discharge by raising and lowering the drive plate 536 of the suction-discharge mechanism 53, the sample suspension is aspirated within the dispensing tip $211_i$. The sample suspension is moved along the X axis by means of the nozzle head transfer mechanism 51 to the first liquid housing part of the liquid housing part group $27_i$ housing the Lysis 1 (enzyme) representing the solution for separating and extracting, and the narrow diameter portion $211_i a$ of the dispensing tip $211_i$ is inserted through the hole in the punched film, and the suction and the discharge is repeated in order to stir the sample suspension and the Lysis 1.

In step S6, the entire amount of the stirred liquid is aspirated by the dispensing tip $211_i$, and incubation is performed by housing it in the reaction vessel $232_i$ comprising the reaction tubes retained in the housing holes, that is set to 55° C. by means of the constant temperature controller. Consequently, the protein contained in the sample is broken down and made a low molecular weight. After a predetermined time has elapsed, the reaction mixture is left in the reaction tube, the dispensing tip $211_i$ is moved to the second liquid housing part of the liquid housing part group $27_i$ by means of the nozzle head transfer mechanism 51, and the entire amount of the liquid housed within the second liquid housing part is aspirated by using the nozzle Z axis transfer mechanism 75 and the suction-discharge mechanism 53, and it is transferred using the dispensing tip $211_i$ by means of the nozzle head transfer mechanism 51, and the reaction solution is discharged within the third liquid housing part by penetrating the hole in the film and inserting the narrow diameter portion.

In step S7, the binding buffer solution housed within the third liquid housing part, which represents a separation and extraction solution, and the reaction solution are stirred, the solubilized protein is further dehydrated, and the nucleic acids or the fragments thereof are dispersed within the solution.

In step S8, using the dispensing tip $211_i$, the narrow diameter portion thereof is inserted into the third liquid housing part by passing through the hole in the film, the entire amount is aspirated and the dispensing tip $211_i$ is raised by means of the nozzle Z axis transfer mechanism 75, and the reaction solution is transferred to the fourth liquid housing part, and the magnetic particle suspension housed within the fourth liquid housing part is stirred with the reaction solution. A cation structure in which Na+ ions bind to the hydroxyl groups formed on the surface of the magnetic particles contained within the magnetic particle suspension is formed. Consequently, the negatively charged DNA is captured by the magnetic particles.

In step S9, the magnetic particles are adsorbed on the inner wall of the narrow diameter portion $211_i a$ of the dispensing tip $211_i$ by approaching the magnet 571 of the magnetic force part 57 to the narrow diameter portion $211_i a$ of the dispensing tip $211_i$. In a state in which the magnetic particles are adsorbed on the inner wall of the narrow diameter portion $211_i a$ of the dispensing tip $211_i$, the dispensing tip $211_i$ is raised by means of the nozzle Z axis transfer mechanism 75 and moved from the fourth liquid housing part to the fifth liquid housing part using the nozzle head transfer mechanism 51, and the narrow diameter portion $211_i a$ is inserted by passing through the hole in the film.

In a state in which the magnetic force within the narrow diameter portion $211_i a$ is removed by separating the magnet 571 of the magnetic force part 57 from the narrow diameter portion $211_i a$ of the dispensing tip $211_i$, by repeating the suction and the discharge of the washing liquid 1 (NaCl, SDS, isopropanol) housed in the fifth liquid housing part, the magnetic particles are released from the inner wall, and the protein is washed by stirring within the washing liquid 1. Thereafter, in a state in which the magnetic particles are adsorbed on the inner wall of the narrow diameter portion $211_i a$ as a result of approaching the magnet 571 of the magnetic force part 57 to the narrow diameter portion $211_i a$ of the narrow diameter portion $211_i a$ again, the dispensing tip $211_i$ is, by means of the nozzle Z axis transfer mechanism 75, moved from the fifth liquid housing part to the sixth liquid housing part by means of the nozzle head transfer mechanism 51.

In step S10, the narrow diameter portion $211_i a$ of the dispensing tip $211_i$ is inserted by passing through the hole in the film using the nozzle Z axis transfer mechanism 75. By repeating the suction and the discharge of the washing liquid 2 (isopropanol) housed in the sixth liquid housing part in a state in which the magnetic force within the narrow diameter portion $211_i a$ is removed by separating the magnet 571 of the magnetic force part 57 from the narrow diameter portion $211_i a$ of the dispensing tip $211_i$, the magnetic particles are stirred within the liquid, the NaCl and the SDS is removed, and the protein is washed. Thereafter, in a state in which the magnetic particles are adsorbed on the inner wall of the narrow diameter portion $211_i a$ by approaching the magnet 571 of the magnetic force part 57 to the narrow diameter portion $211_i a$ of the dispensing tip $211_i$ again, the dispensing tip $211_i$ is, following raising by means of the nozzle Z axis transfer mechanism 75, moved from the sixth liquid housing part to the seventh liquid housing part in which the distilled water is housed, by means of the nozzle head transfer mechanism 51.

In step S11, the narrow diameter portion $211_i a$ of the dispensing tip $211_i$ is lowered through the hole by means of the nozzle Z axis transfer mechanism 75, and by repeating the suction and the discharge of the distilled water at a slow flow rate in a state where the magnetic force is applied within the narrow diameter portion $211_i a$ of the dispensing tip $211_i$, the washing liquid 2 (isopropanol) is substituted by water and is removed. Thereafter, by stirring the magnetic particles by repeating the suction and the discharge within the distilled water which represents the dissociation liquid, in a state in which the magnet 571 of the magnetic force part 57 is separated from the narrow diameter portion $211_i a$ of the dispensing tip $211_i$ and the magnetic force is removed, the nucleic acids or the fragments thereof retained by the magnetic particles are dissociated (eluted) from the magnetic particles into the liquid. Thereafter, a magnetic field is applied within the narrow diameter portion and the magnetic particles are adsorbed on the inner wall by approaching the magnet 571 to the narrow diameter portion $211_i a$ of the dispensing tip $211_i$, and the solution containing the extracted nucleic acids, and the like, is made to remain in the eighth liquid housing part. The dispensing tip $211_i$ is moved to the storage part of the housing parts for tips and the like $21_i$ in which the dispensing tip $211_i$ was housed, by means of the nozzle head transfer mechanism 51, and the dispensing tip $211_i$ to which magnetic particles are adsorbed, is detached from the nozzle $71_i$ together with the magnetic particles and dropped into the storage part, using the detaching member 591 of the tip detaching mechanism 59.

The following step S12 to step S15 corresponds to nucleic acid amplification and measurement processing.

In step S12, a new dispensing tip $211_i$ is mounted on the nozzle $71_i$, the solution housed within the eighth liquid housing part, which contains nucleic acids and the like, is aspirated, and by transferring it to the PCR tube $231_i$ in which the solution for amplification $234_i$ is housed beforehand, and discharging it, it is introduced into the vessel. As a result of moving the nozzle head 50 by means of the nozzle head transfer mechanism 51, the nozzle $71_i$ is moved above the sealing lid housing part $25_i$ of the vessel group 20, which houses the sealing lid $251_i$. Mounting is performed by lowering using the nozzle Z axis transfer mechanism 75 and fitting an indentation for linking $258_i$ on the upper side of the sealing lid 251 to the lower end of the nozzle $71_i$. After being raised by the nozzle Z axis transfer mechanism 75, the sealing lid 251 is positioned above the PCR tube $231_i$ using the nozzle head transfer mechanism 51, and by lowering the sealing lid $234_i$ by means of the nozzle Z axis transfer mechanism 75, it is fitted with the aperture of the wide-mouthed piping part $235_i$ of the PCR tube $231_i$, mountingly sealing it.

In step S13, the nozzle head transfer mechanism 51 is instructed by means of an instruction from the measurement control portion 61, and by moving the nozzle head 50 along the X axis, the linking portion $31_i$ of the light guide stage 32 is positioned above the PCR tube $231_i$, which is mounted with the sealing lid $251_i$. Then, by lowering the light guide stage 32 by means of the stage Z axis transfer mechanism 35, the linking portion $31_i$ is inserted into the indentation of the sealing lid $251_i$, and the lower end thereof is made to make contact with, or adhere to, the bottom surface of the indentation.

In step S14, due to an instruction by the nucleic acid processing controller 63, the temperature controller 29 instructs a temperature control cycle by real-time PCR, such as a cycle in which the PCR tube $231_i$ is heated for five seconds at 96° C. and heated for 15 seconds at 60° C., to be repeated forty nine times for example.

In step S15, when temperature control at each cycle by the nucleic acid processing controller 63 is started, the measurement control portion 61 determines the start of elongation reaction processing at each cycle, and instructs the continuous or intermittent movement of the connecting end arranging body 30 with respect to the measuring ends $44_j$ of the measuring device 40. For the movement speed thereof, it is moved at a speed that is calculated based on the stable light receivable time, the fluorescence lifetime, and the number (twelve in this example) of exclusive regions $20_i$. Consequently, the receiving of light from all twelve PCR tubes $231_i$ within the stable light receivable time becomes completed.

In step S16, the measurement control portion 61 determines the moment of each optical connection between the optical fibers (bundles) $33_i$ of the linking portions $31_i$ and the first measuring end and the second measuring end of the measuring end 44, and instructs the receiving of light to the measuring device 40 for example.

This measurement is executed with respect to cycles in which exponential amplification is performed, and an amplification curve is obtained based on the measurement, and various analyses are performed based on the amplification curve. At the time of the measurement, the measurement control portion 61 heats the heater 37 built into the light guide stage 32 and prevents the condensation on the sealing lid 251, and a clear measurement can be performed.

Figure 11:
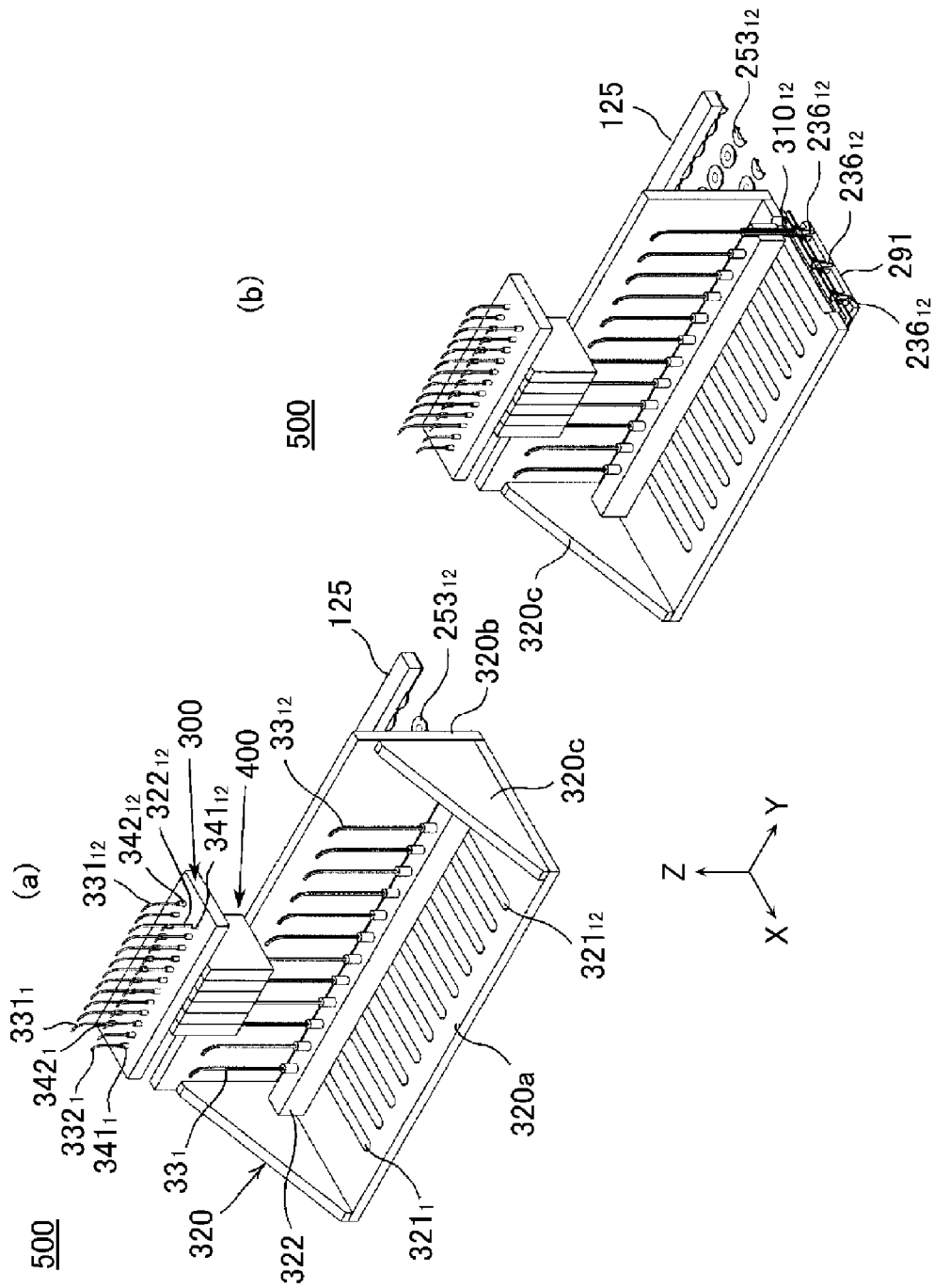
FIG. 11 is a perspective view showing a light guide stage, a connecting end arranging body, and a sealing lid transport mechanism of a light measurement apparatus for a reaction vessel according to a second exemplary embodiment.
Figure 12:
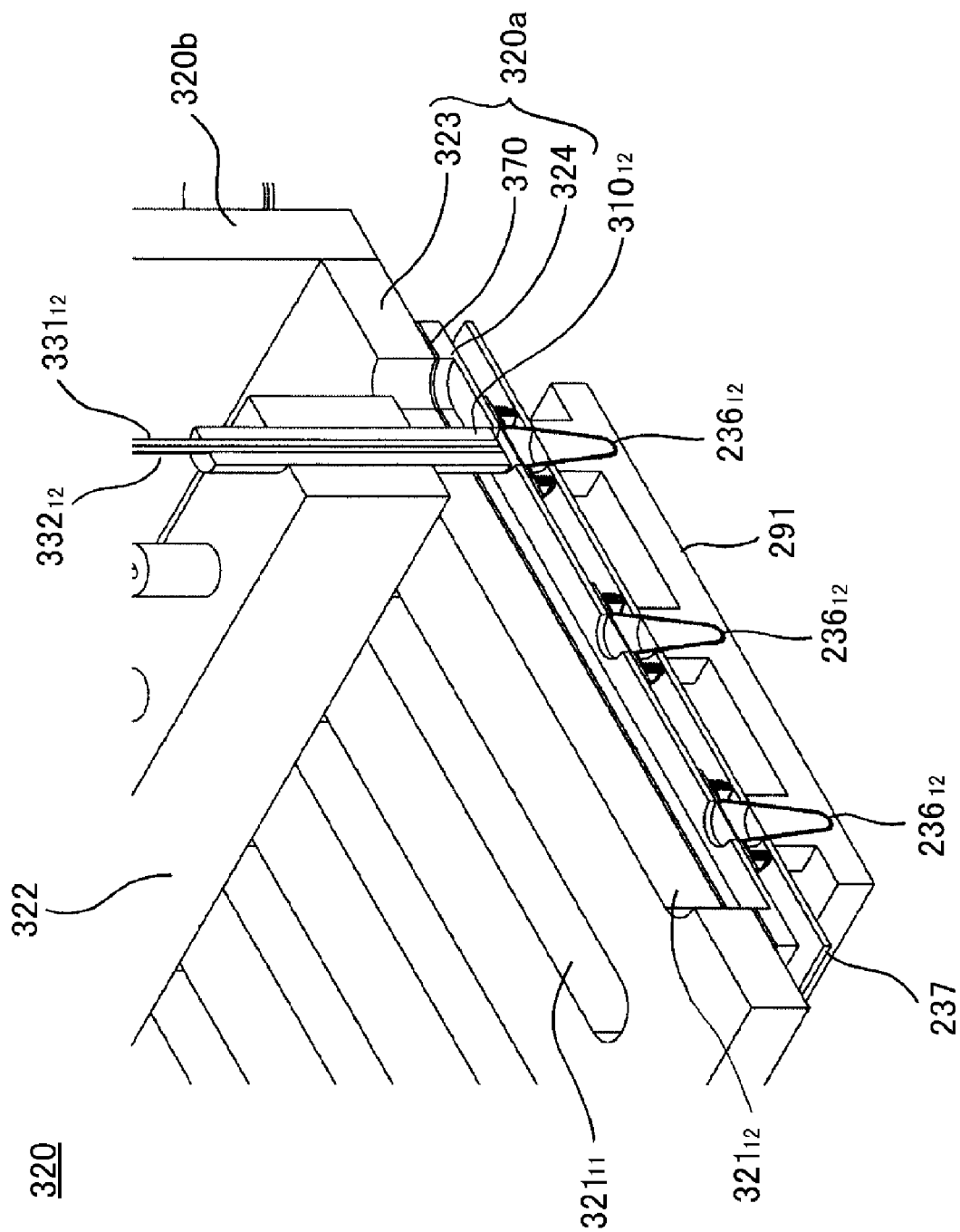
FIG. 12 is an enlarged perspective view showing the light guide stage shown in FIG. 11 with a portion cut away.

FIG. 11 is a perspective view of the front side of a nozzle head 500 of a light measurement apparatus for a reaction vessel according to a second exemplary embodiment of the present invention, and a perspective view showing a portion thereof cut away. FIG. 12 is a perspective view showing enlarged, the portion of FIG. 11 shown cut away.

As shown in FIG. 11, in this example, unlike the light measurement apparatus for a reaction vessel according to the first exemplary embodiment, the PCR tubes $236_i$, which represent the reaction vessel, have a vessel group in which three or more rows of twelve each are arranged.

There are no large differences with the first exemplary embodiment with respect to the section of the nozzle head 500 related to a dispensing device, which includes the nozzles, and the section related to the traversable nozzle, the transfer mechanisms of the nozzle head, and the arranging body transfer mechanism, and they are omitted from the descriptions. The nozzle head 500 has: a light guide stage 320; twelve linking portions $310_i$ provided on the light guide stage 320; optical fibers (bundle) $33_i$ that extend from the linking portions $310_i$ on the rear side; a connecting end arranging body 300; a measuring device 400 having a measuring end comprising six types of specific wavelength measurement devices that are aligningly mounted on the light guide stage 320; and a sealing lid transporting body 125.

The light guide stage 320 according to the second exemplary embodiment has a linking portion arranging body 322, in which two or more (twelve in this example) linking portions 310, that are simultaneously linkable with two or more (twelve in this example) PCR tubes $236_i$ representing reaction vessels, are arranged, that is movable in the horizontal direction (the X axis direction in this example) with respect to the light guide stage 320. Furthermore, by means of the movement of the linking portion arranging body 322, without moving the light guide stage 320, it is linkable with more PCR tubes $236_i$ representing reaction vessels (three rows of reaction vessels with twelve per row in this example) than the number of reaction vessels (twelve in this example) that are simultaneously linkable by the linking portion arranging body 322.

The light guide stage 320 has a horizontal plate 320a, a vertical plate 320b, and a triangular-shaped support side plate 320c. The horizontal plate 320a of the light guide stage 320, according to the arrangement of the linking portions 310, arranged on the linking portion arranging body 322, is etchingly provided with two or more, or twelve in this example, long holes $321_i$ that correspond to shielding regions.

The measurement device 400 is mounted fixed to the upper edge of the vertical plate 320b of the light guide stage 320. Therefore, since the light guide stage 320 is stationary at the time of receiving light, the measurement device 400 is immovably provided with respect to the reaction vessel and the light guide stage 320.

The optical fibers (bundle) $33_i$ having the end of the linking portion $310_i$, separate midway into optical fibers for receiving light (bundle) $331_i$ and optical fibers for irradiation (bundle) $332_i$. The optical fibers for receiving light (bundle) $331_i$ connect to a second connecting end $341_i$, and the optical fibers for irradiation (bundle) $332_i$ connect to a first connecting end $342_i$, and are arranged as two paths along the Y axis direction on a downwardly facing horizontal plane, which represents an arranging surface on the lower side of the connecting end arranging body 300. At that time, the spacing between adjacent connecting ends on these respective paths is such that they are integrated at approximately half or one-third of the spacing of the linking portions for example. The first connecting ends $342_i$ are successively connectable with the first measuring ends of the measurement device 400, and the second connecting ends $341_i$ are successively connectable with the second measuring ends.

Figure 13:
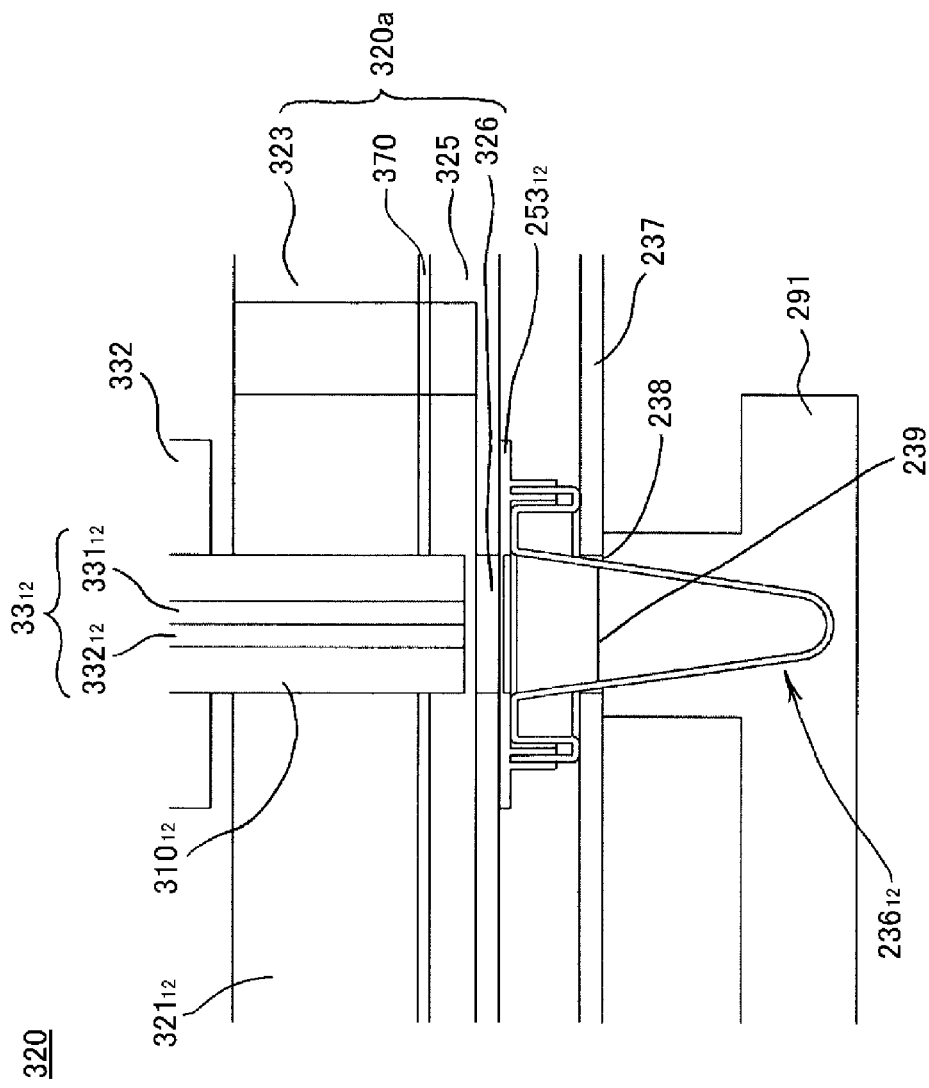
FIG. 13 is an enlarged cross-sectional view of the linking portion shown in FIG. 12.

As shown in FIG. 12 or FIG. 13, the horizontal plate 320a of the light guide stage 320 is laminatingly provided with a thermal insulation plate 323 formed by a resin and the like, a heater 370 provided on the lower side of the thermal insulation plate 323 for preventing condensation of the sealing lids $253_i$ by heating the sealing lids $253_i$, and a thermally conductive metallic plate 325 provided on the lower side of the heater 370. Reference symbol 238 is a housing hole that houses the PCR tubes $236_i$ representing reaction vessels, and is piercingly provided in the cartridge vessel. Reference symbol 239 represents a liquid surface that is controlled at a fixed height within the PCR tubes $236_i$ representing reaction vessels. Reference symbol 291 is a temperature controller for PCR.

The long holes $321_i$ that are etchingly provided in the horizontal plate 320a reach the metallic plate 325. Holes 326 for light transmission that are the same size as the apertures are piercingly provided above the apertures of the PCR tubes $236_i$ representing reaction vessels, of the metallic plate 325 on the bottom of the long holes $321_i$, and are optically communicated with the bottom of the long holes $321_i$.

The linking portions $310_i$ provided on the linking portion arranging body and the ends of the optical fibers (bundle) $33_i$ provided in the interior are, as a result of approaching the sealing lids $253_i$, linked with the PCR tubes $236_i$ representing reaction vessels.

Figure 14:
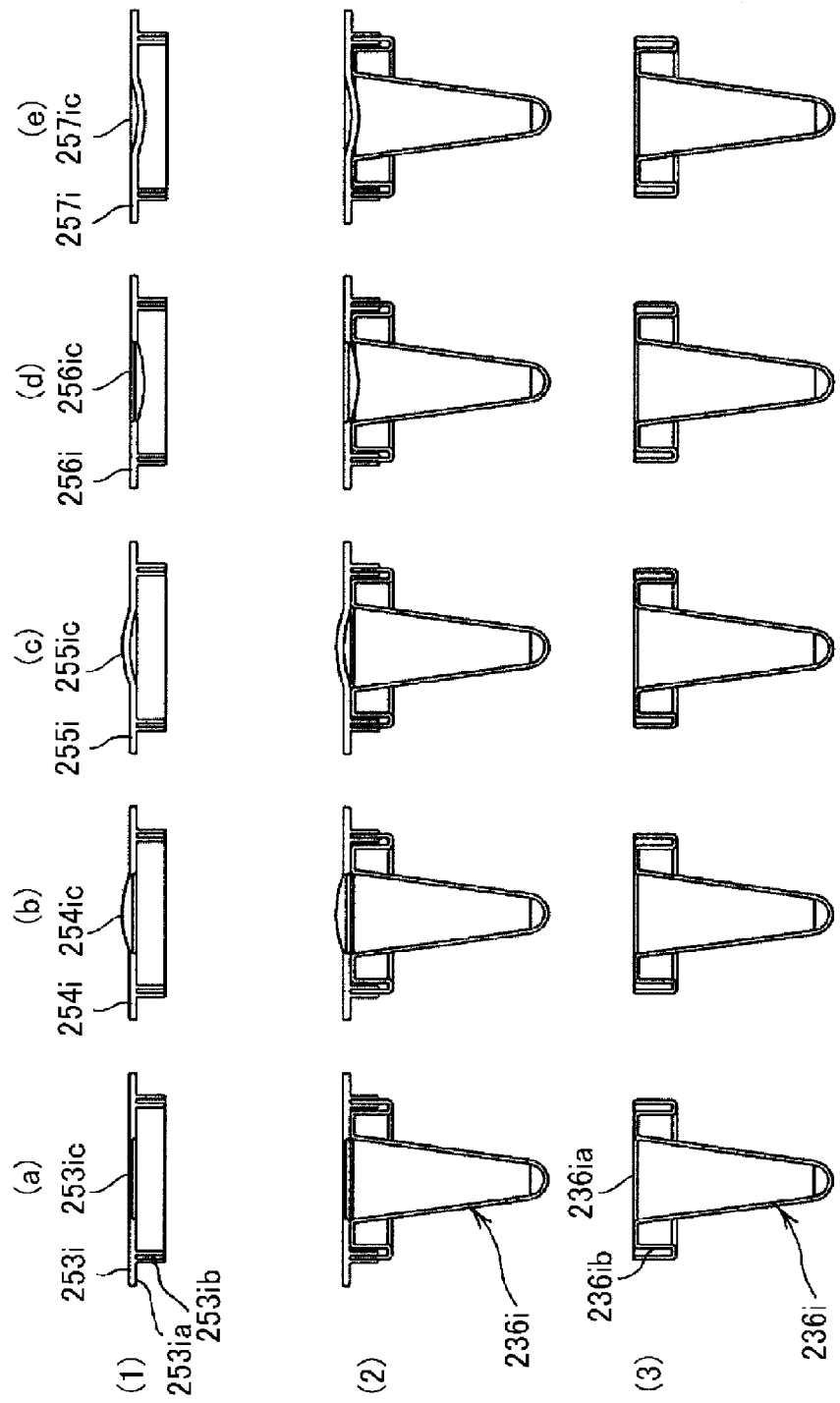
FIG. 14 is a cross-sectional view showing an example of the sealing lid shown in FIG. 11.

FIG. 14 is a drawing showing the various sealing lids $254_i$ to $257_i$ according to the second exemplary embodiment, that are mountable on the reaction vessel.

In FIG. 14A, the sealing lid $253_i$ has: a cover plate $253_ia$ that covers the aperture $236_ia$ of the PCR tube $236_i$ representing a reaction vessel; a central portion $253_ic$ that is formed at the center of the cover plate $253_ia$ and thinner than the periphery, and has an increased light transmittance; and a clamp $253_ib$ comprising a double annular wall that is provided such that it encloses the central portion $253_ic$ and protrudes on the lower side, that represents a mounting portion that is mountable to the outer edge portion $236_ib$ of the aperture of the reaction vessel.

The sealing lid $254_i$ shown in FIG. 14B is formed thick in a convex lens form having a curved surface that expands from a central portion $254_ic$ toward the vessel exterior. Consequently, the light that is generated within the reaction vessel is made to converge at the end of an optical fiber, or the excitation light from the optical fiber is made to converge at the liquid surface and the like, and the light can be efficiently collected.

The sealing lid $255_i$ shown in FIG. 14C is formed in a convex lens form having a curved surface that expands from a central portion $255_ic$ toward the vessel exterior, and consequently, the effects demonstrated in FIG. 14B are achieved.

The sealing lid $256_i$ shown in FIG. 14D is formed thick such that it has a curved surface that expands from a central portion $256_ic$ toward the vessel exterior. Consequently, the effects demonstrated in FIG. 14B are achieved.

The sealing lid $257_i$ shown in FIG. 14E is formed such that it has a curved surface that expands from a central portion $257_ic$ toward the vessel exterior, and consequently, the effects demonstrated in FIG. 14B are achieved.

Figure 15:
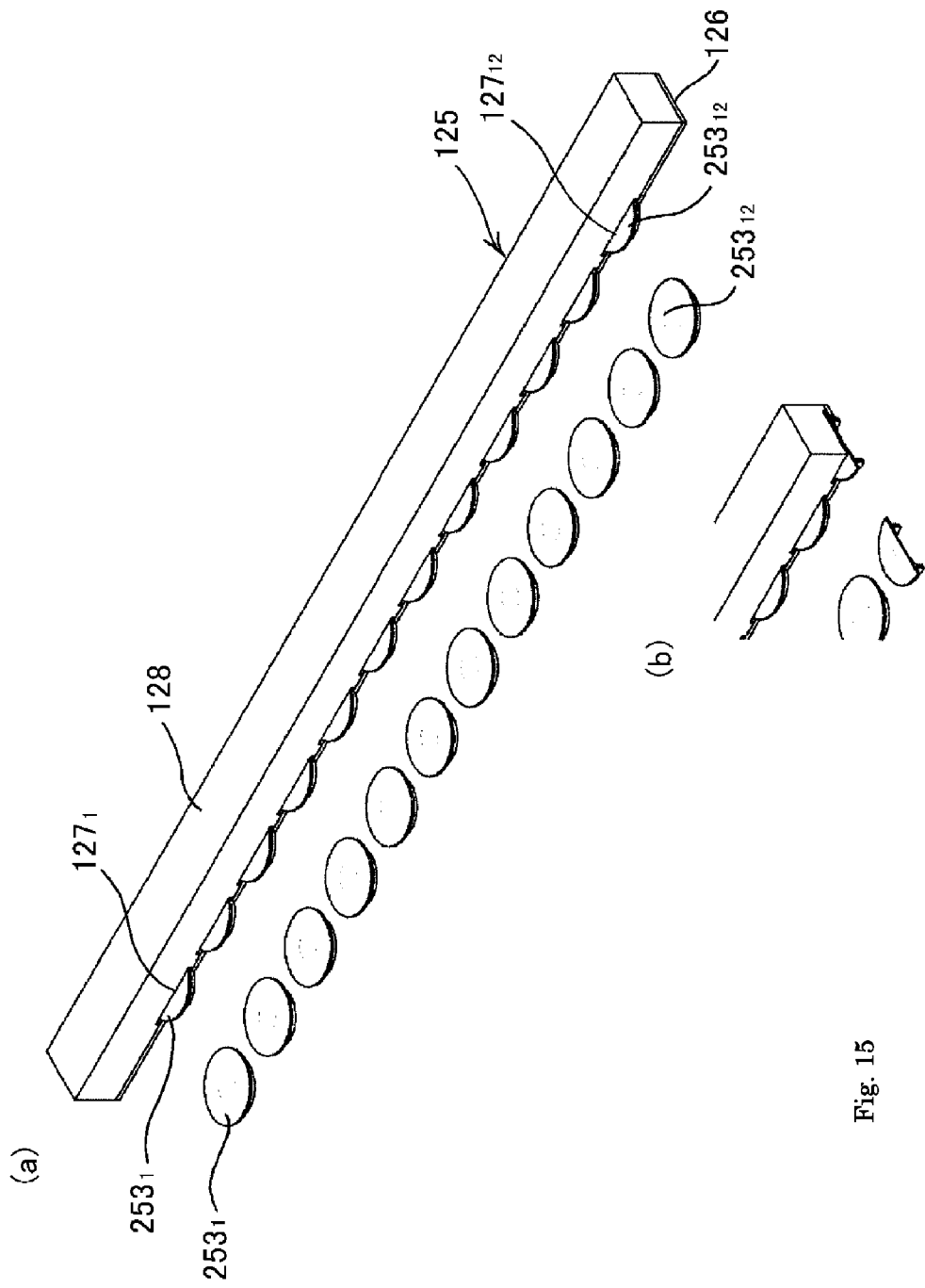
FIG. 15 is an enlarged perspective view of the sealing lid transporting body shown in FIG. 11.

FIG. 15 shows a sealing lid transporting body 125 according to the second exemplary embodiment.

The sealing lid transporting body 125 is one having: a prismatic substrate 128 that is movable in the X axis direction with respect to the vessel group 20, which has at least three rows of PCR tubes $236_i$ representing reaction vessels of twelve per row; one or two or more (twelve in this example) grippers $127_i$ arranged on the prismatic substrate 128 according to the arrangement of the reaction vessels that grip the cover plate such that, with respect to the sealing lid $253_i$ (to $256_i$), the lower side is exposed in a state in which the mounting portion is mountable to the reaction vessel; and a bottom plate 126 that is mounted on the lower side of the prismatic substrate 128.

Figure 16:
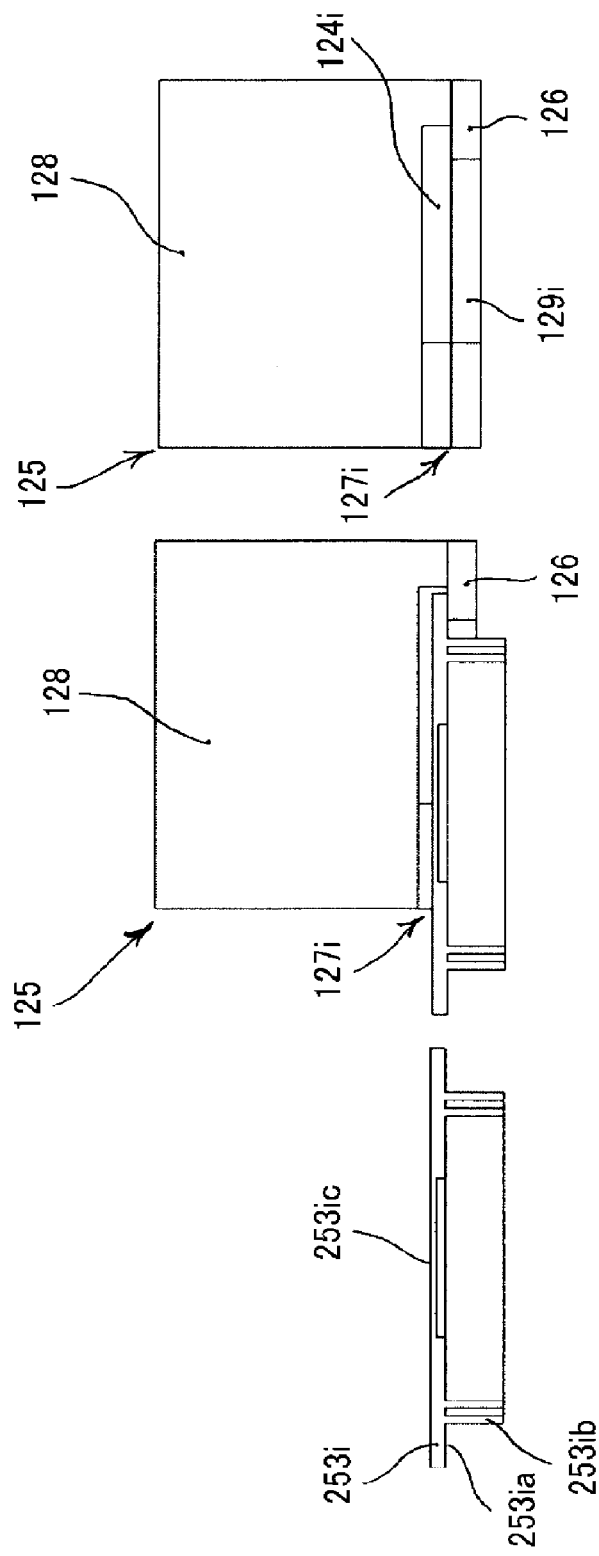
FIG. 16 is a cross-sectional view of the sealing lid transporting body shown in FIG. 15.
Figure 17:
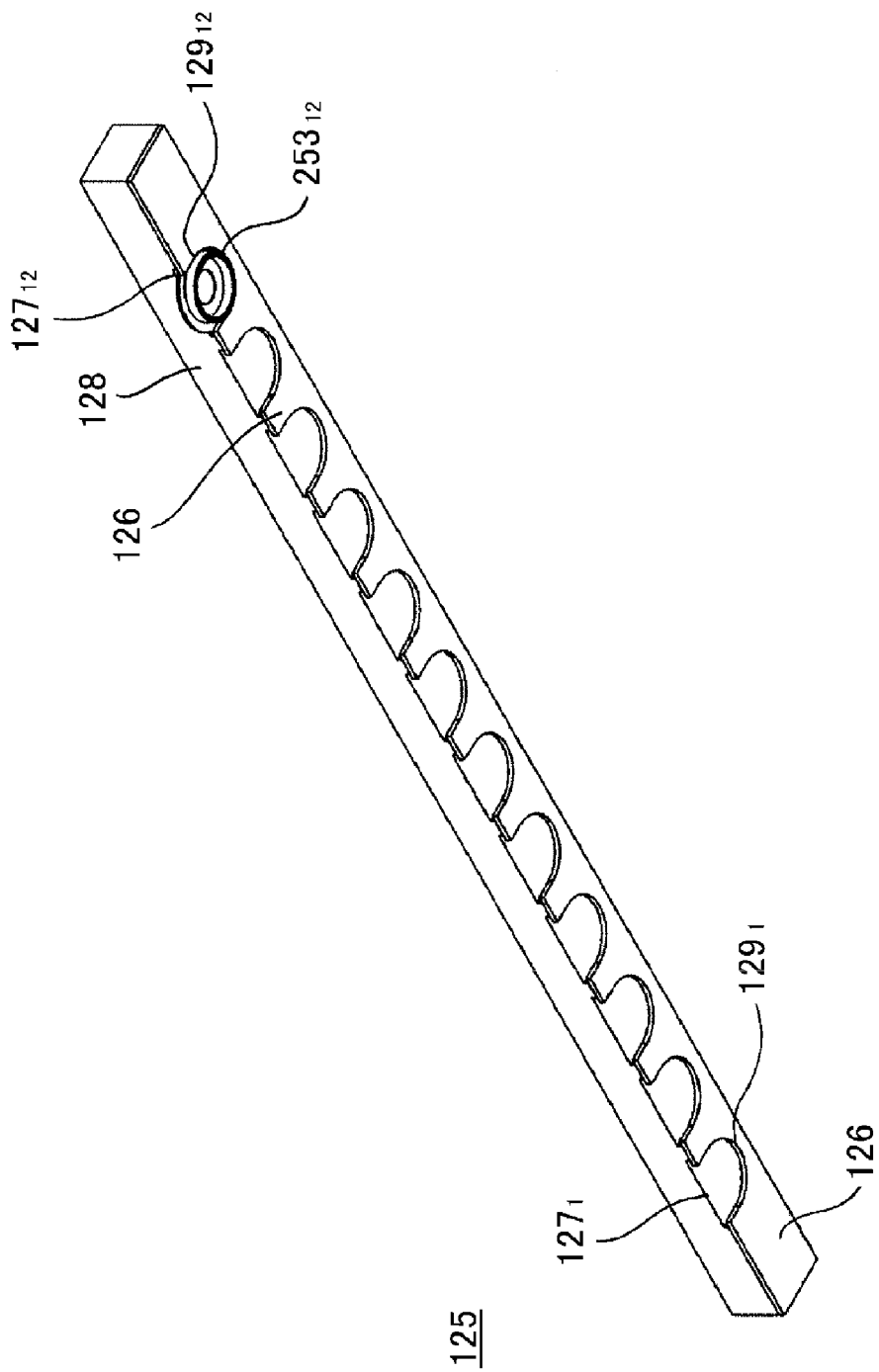
FIG. 17 is a perspective view as viewed from the lower side of the sealing lid transporting body shown in FIG. 15.

As shown in the cross-sectional view of FIG. 16 and the perspective view as viewed from the lower side of FIG. 17, the grippers $127_i$ have a cavity $124_i$ that is cut out from the prismatic substrate 128 in an approximate semicircular column shape such that most of the cover plate $253_ia$ of the sealing lid $253_i$ is housable. Furthermore, the bottom plate 126 is provided with a semicircular hole shaped notch portion $129_i$ such that the clamp $253_ib$, which represents the mounting portion of the sealing lid $253_i$, is exposable on the lower side.

Next, the processing operation using the nozzle head 500 according to the second exemplary embodiment is described.

Among the processes described in the first exemplary embodiment, the separation and extraction process is omitted, and step S'12 to step S'16, which correspond to nucleic amplification and measurement processes, are described.

In step S'12, a new dispensing tip $211_i$ is mounted on the nozzle $71_i$, the solution containing nucleic acids and the like, which is housed within the eighth liquid housing part is aspirated, transported to the PCR tube $236_i$ representing a reaction vessel in which the solution for amplification $234_i$ is housed beforehand, and discharged and introduced into the vessel. As a result of moving the nozzle head 500 by means of the nozzle head transfer mechanism 51, the sealing lids $253_i$ from the sealing lid housing part in the sealing lid transporting body 125 in which twelve sealing lids $253_i$ are housed, are simultaneously housed in the cavity $124_i$ of the grippers $127_i$, and gripped.

Since the sealing lid transporting body 125 gripping the sealing lid $253_i$ is linked with the light guide stage 320, then by using the stage Z axis transfer mechanism 35 and moving it somewhat upwardly together with the stage 320 and then moving it in the X axis direction, and by transporting it to above the PCR tubes $236_i$ representing reaction vessels and lowering it, the twelve sealing lids 253, are sealed by mounting the clamps $253_ib$, which are exposed on the lower side from the sealing lid transporting body 125, to the PCR tubes $236_i$. In the same manner, the rows of the twenty four reaction vessels of the other two rows are successively sealed by the sealing lids.

In step S'13, due to an instruction by the measurement control portion 61, as a result of instructing the nozzle head transfer mechanism 51 and moving the nozzle head 500 along the X axis, the light guide stage 320 is moved such that it covers the thirty six reaction vessels of the three rows, on which the sealing lids are mounted.

In step S'14, due to an instruction by the nucleic acid processing control portion 63, the temperature controller 29 instructs a temperature control cycle by real-time PCR, such as a cycle in which the PCR tubes $231_i$ are heated for five seconds at 96° C. and heated for fifteen seconds at 60° C., to be repeated forty nine times for example.

In step S'15, when temperature control at each cycle is started by the nucleic acid processing control portion 63, the measurement control portion 61 determines the start of the elongation reaction process at each cycle, moves the linking portion arranging body 322 provided on the light guide stage 320 over the light guide stage 320, indirectly links the respective linking portions $310_i$ that are inserted into the long holes $321_i$ provided on the light guide stage 320 via the reaction vessels and the sealing lids $253_i$, and successively receives the light from the reaction vessels while irradiating excitation light from the measurement device to the interior of the reaction vessels. At the same time, the continuous or intermittent movement of the connecting end arranging body 300 with respect to the respective measuring ends $44_j$ of the measurement device 400 is instructed. The movement speed thereof is such that movement is performed at a speed that is calculated based on the stable light receivable time, the fluorescence lifetime, the number (three rows of twelve reaction vessels per row in this example) of reaction vessels of the exclusive regions $20_i$ that are measurable by the light guide stage 320, and the like. Consequently, by moving the linking portion arranging body 322 over the light guide stage 320 within the stable light receivable time, in this example, measurements can be performed in parallel with respect to thirty six reaction vessels of three rows, with twelve per row.

In step S'16, the measurement control portion 61 determines the moment of the respective optical connections between the optical fibers (bundle) of the linking portions $310_i$ and the first measuring end and the second measuring end of the measuring end 44, and instructs the irradiation of excitation light and the receiving of light to the measurement device 400.

Figure 18:
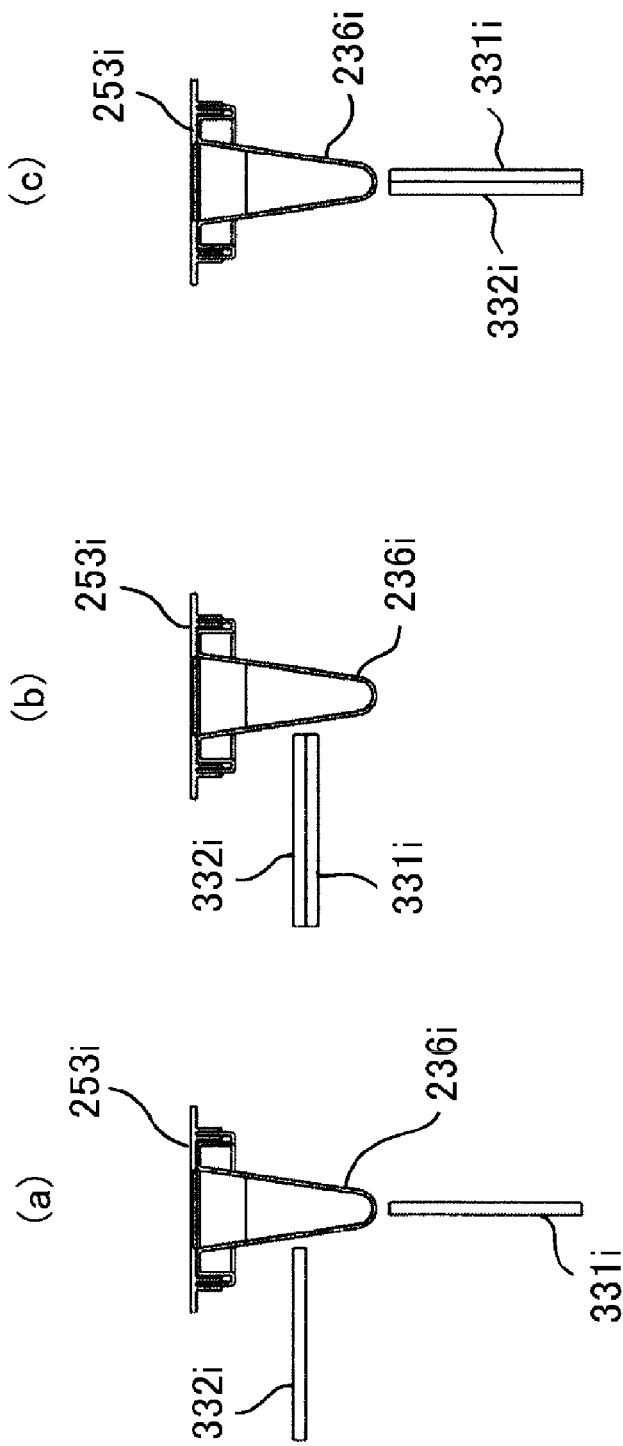
FIG. 18 is a schematic diagram showing an example of the positional relationship between the optical fiber ends provided on the linking portions and the reaction vessel.

FIG. 18 is a drawing showing an example of the position of the optical fiber front ends for receiving light and for irradiation provided to the linking portion in a case where the linking portion is linked at a location other than the aperture of the PCR tube $236_i$ representing a reaction vessel. FIG. 18A is a drawing showing a case where the optical fibers (bundle) for receiving light $331_i$ are in the vicinity of the outer bottom portion of the reaction vessel, and the optical fibers (bundle) for irradiation $332_i$ are in the vicinity of the outer wall of the reaction vessel. FIG. 18B is a drawing showing a case where the optical fibers (bundle) for receiving light $331_i$ and the optical fibers (bundle) for irradiation $332_i$ are in the vicinity of the outer wall of the reaction vessel. FIG. 18C is a drawing showing a case where the optical fibers (bundle) for receiving light $331_i$ and the optical fibers (bundle) for irradiation $332_i$ are in the vicinity of the outer bottom portion of the reaction vessel. These are only examples, and cases where they are joined with the reaction vessel by making contact, and the like, in place of being in the vicinity are also possible.

Figure 19:
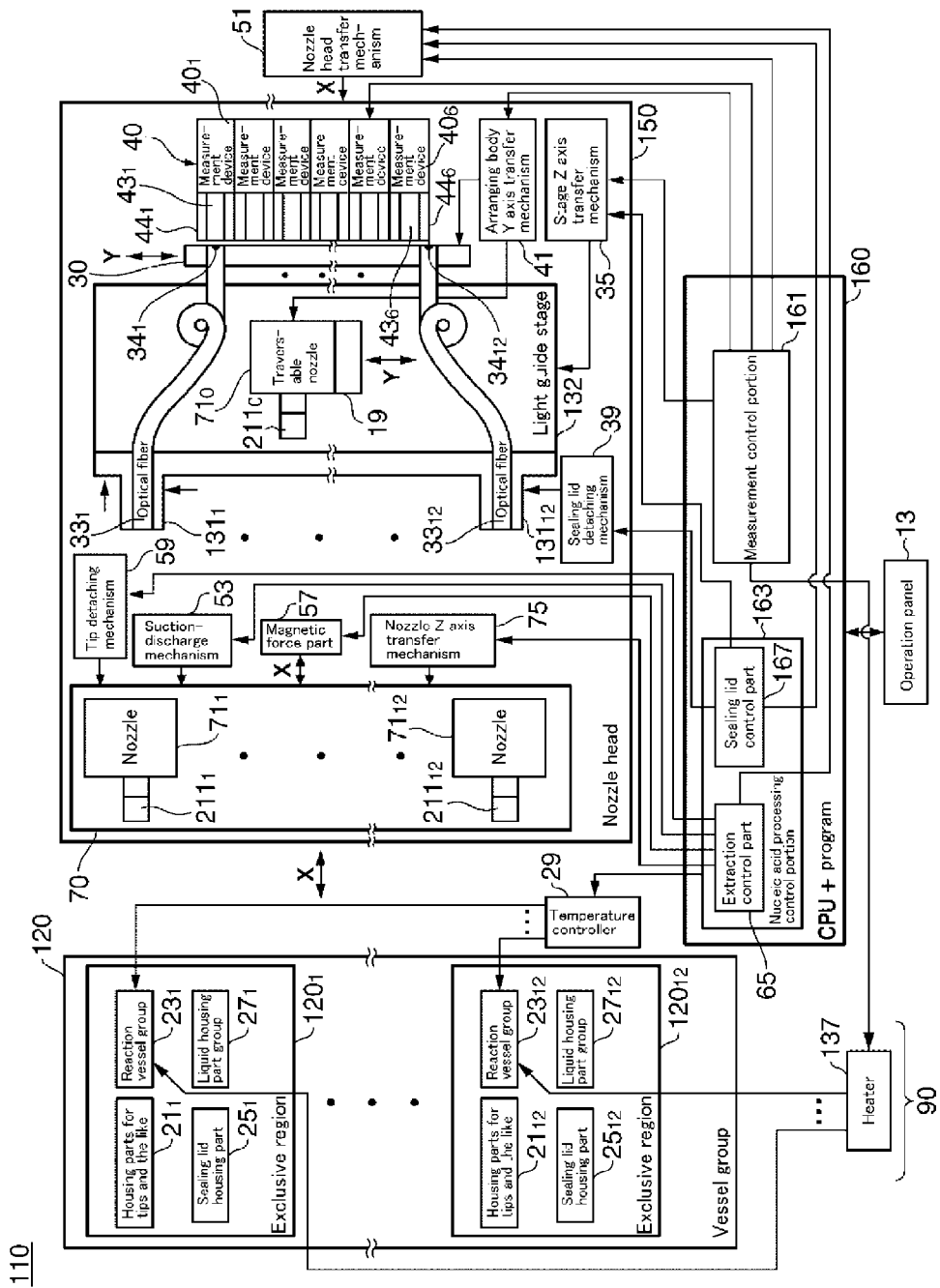
FIG. 19 is an overall block-diagram showing a light measurement apparatus for a reaction vessel according to a second embodiment of the present invention.

FIG. 19 represents a block-diagram of a light measurement apparatus for a reaction vessel 110 according to a second embodiment of the present invention. Since the same reference symbols as the reference symbols used in the first embodiment represent the same objects or similar (only differing by size) objects, the descriptions thereof are omitted.

The light measurement apparatus for a reaction vessel 110 according to the second embodiment differs from the light measurement apparatus for a reaction vessel 10 according to the first embodiment in the aspect that the nozzle head 150 thereof has a light guide stage 132 that is different from the light guide stage 32. The light guide stage 132 according to the second embodiment differs from the light guide stage 32 according to the first embodiment in the aspects that it has a plurality (twelve in this example) of linking portions $131_i$ in which the front ends of optical fibers, which represent two or more light guide portions, which have a flexibility, that optically connect with the interior of the PCR tubes $231_i$, and an optical element for collecting light are provided in the interior, and the heat source of the heater 137, which represents a heating portion for heating the reaction vessels, is provided not to the light guide stage 132, but to the vessel group 120 or the stage.

Further, it differs in the aspects that the sealing lids $251_i$ are transported not by the nozzles $71_i$ but by fitting to the linking portions $131_i$, and are detached from the linking portions by means of a dedicated sealing lid detaching mechanism 39. Therefore, the sealing lid control portion 167, and therefore, the nucleic acid processing control portion 163 and the CPU+program 160 differ from the device 10 according to the first embodiment.

The vessel group 120 is one in which twelve exclusive regions $120_i$ (i=1, . . . , 12), wherein the longitudinal direction thereof is along the X axis direction and housing parts are arranged in a single row form, are arranged in the Y axis direction for example. The respective exclusive regions $120_i$ have: a reaction vessel group $23_i$; a liquid housing part group $27_i$; a sealing lid housing part $25_i$ that houses sealing lids $251_i$, which have transparency, that are detachably mounted on the linking portions $131_i$ provided to the light guide stage 132; and housing parts for tips and the like $21_i$.

The reaction vessel $23_i$, the temperature controller 29, and the heater 137 correspond to the reaction vessel control system 90.

Figure 20:
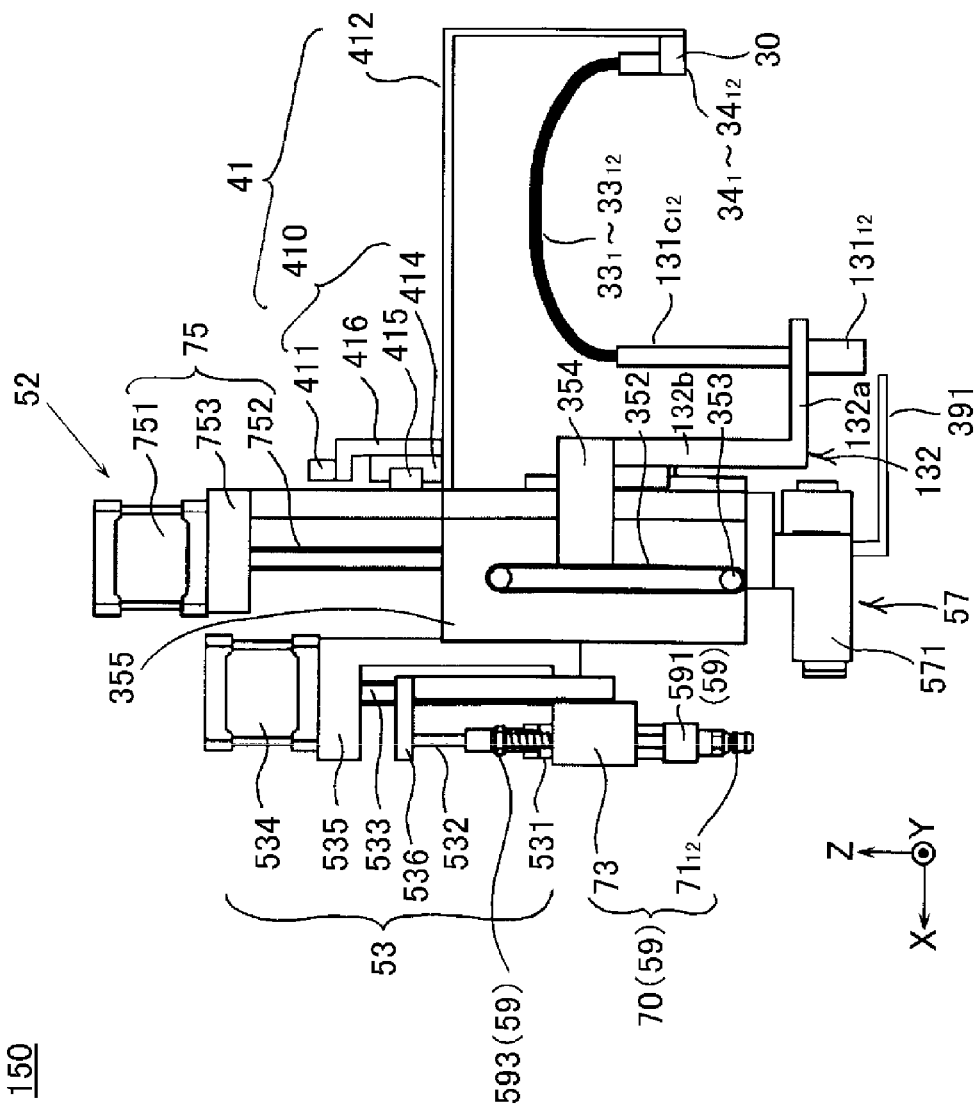
FIG. 20 is a side view showing more specifically, the transfer mechanism and the suction-discharge mechanism according to a first exemplary embodiment of FIG. 19.

FIG. 20 is a cross-sectional view primarily showing, within the nozzle head 150 according to a first exemplary embodiment of the second embodiment, the transfer mechanism and the suction-discharge mechanism.

Here, since the diameter of the linking portion $131_i$ is thicker than the nozzle $71_i$, the sealing lid $251_i$ to be mounted on the PCR tube is transported by the linking portion $131_i$. Consequently, by utilizing the transfer mechanism of the magnet 571 of the magnetic force part 57, a sealing lid detaching mechanism 39 is provided that has a comb-shaped detaching member 391 in which a notch portion, which has a semicircular-shaped arch that is approximately equivalent to the diameter of the twelve linking cylinders provided such that they can approach and separate with respect to the linking portion $131_i$, is arranged. In the present exemplary embodiment, since the detachment of the sealing lids can be performed by utilizing existing mechanisms, the expansion of the apparatus scale, and increases in complexity, can be prevented.

Figure 21:
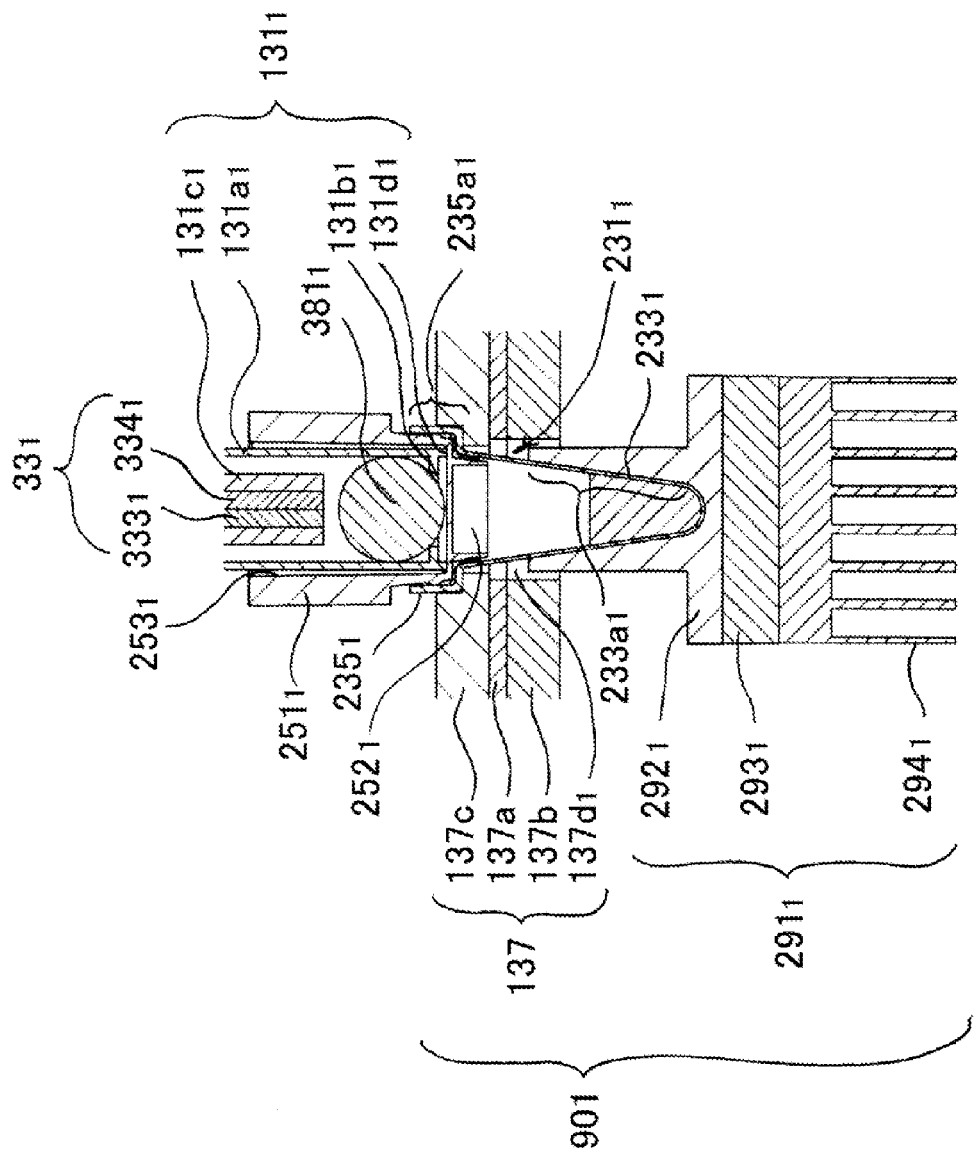
FIG. 21 is a cross-sectional view showing a state in which a linking portion according to the first exemplary embodiment of FIG. 19 is linked with a reaction vessel.

FIG. 21 is a drawing showing a reaction vessel control system 901 according to the first exemplary embodiment of the second embodiment and a state in which, to the apertures of the reaction vessel group, to which the PCR tubes $231_i$ representing a plurality (twelve in this example) of reaction vessels of the reaction vessel control system 901 are provided, the linking portions 131, (here, i=1 for example) protruding on the lower side from the horizontal plate 132a of the light guide stage 132 are indirectly linked with the PCR tubes 231i via the sealing lids 251i, which have transparency, that are mounted on the apertures of the PCR tubes $231_i$ in the exclusive regions $120_i$. As a result of the linking portions $131_i$ fitting within the indentation for linking $253_i$ of the sealing lids $251_i$, they are linked with the PCR tubes $231_i$.

As shown in FIG. 21, the linking portion $131_i$ is indirectly linked with the PCR tube $231_i$ via the sealing lid 253, and has an approximately cylinder-shaped linking cylinder $131a_i$ that is protrudingly provided further in the downward direction than the horizontal plate 132a of the light guide stage 132. Furthermore, a circular hole $131b_i$ having an aperture of a size corresponding to the liquid surface of the liquid that is housed in the narrow-mouthed piping part is piercingly provided in the center portion of the bottom plate of the linking cylinder $131a_i$, and the periphery of the bottom plate is provided with a circular edge portion $131d_i$ that is protrudingly provided below it. Consequently, the adhesion of the linking portion and the sealing lid is prevented. A spherical ball lens $381_i$ that has a diameter corresponding to the inner diameter of the linking cylinder is loosely inserted within the linking cylinder $131a_i$ and mounted on the circular hole $131b_i$. At a predetermined distance above the ball lens $381_i$, an optical fiber $33_i$, in which the end is positioned and is covered by a resin-made ferrule $131c_i$ that passes through the horizontal plate 132a and reaches the exterior, is provided. The linking cylinder $131a_i$, the circular hole $131b_i$, the ball lens $381_i$, and the optical fiber $33_i$ bundle are arranged on the same axis in the interior of the linking cylinder $131a_i$.

As shown in FIG. 21, the reaction vessel control system 901 has: PCR tubes $231_i$ that represent reaction vessels, in which target solutions of DNA having a target base sequence, and the like, are stored and reactions, such as amplification, are performed; a heater 137; and a temperature controller $291_i$ for PCR. The heater 137 is laminatingly provided with a heating block 137c comprising an aluminum plate having a high thermal conductivity, a sheet heater 137a, and a heat insulator 137b. Twelve through holes $137d_i$ that house and retain a plurality (twelve in this example) of PCR tubes $231_i$ are piercingly provided in the same heater 137, and the wide-mouthed piping parts $235_i$ are supported by the heating block 137c.

The temperature controller 291 for PCR has: a block for temperature control $292_i$ that makes contact with, and is housable in, the narrow-mouthed piping part $233_i$ of the PCR tube $231_i$, which represents the reaction vessel; a Peltier element $293_i$; and a heat sink $294_i$.

The narrow-mouthed piping part $233_i$ of the PCR tube $231_i$ has a lower side wall section $233a_i$ of the section in which the block for PCR $292_i$ is making contact and is provided. Furthermore, it has an upper side wall section $235a_i$ provided on the upper side leaving a spacing with the lower side wall section $233a_i$ that corresponds to the wall section of the wide-mouthed piping part $235_i$ that makes contact with the block for heating 137c of the heater.

According to the present exemplary embodiment, firstly, by means of an instruction by the sealing lid control portion 167 (the CPU+program 160), the nozzle head transfer mechanism 51 is instructed and following movement of the respective linking portions $131_i$ of the light guide stage 132 to the sealing lid housing parts $25_i$, the stage Z axis transfer mechanism 35 is instructed and the sealing lids $251_i$ are fitted and mounted to the linking portions $131_i$. Next, by fitting the apertures of the predetermined PCR tubes $231_i$ with the sealing lids $251_i$, the linking portions $131_i$ are simultaneously linked with the PCR tubes $231_i$.

Next, according to the temperature control by the temperature controller 29 as a result of an instruction by the measurement control portion 161, in the case of PCR, by controlling the heater 137 such that the upper side wall section 235$a_i$ is heated at a fixed temperature (100° C. for example) that is several degrees, or preferably approximately 5° C., higher than the maximum predetermined temperature (94° C. for example), the sealing lid 251$_i$ fitted to the wide-mouthed piping part 235$_i$ of the PCR tube 231$_i$ is heated, and condensation of the sealing lid can be prevented. At that time, the upper side wall section 235$a_i$ is separated by a fixed spacing from the lower side wall section 233$a_i$, in which temperature control is performed, and the upper side wall section 235$a_i$, which has a smaller surface area than the lower side wall section, is heated by bringing the heat source into contact or into its vicinity. Consequently, the effect of heating the upper side walls section 235$a_i$ is such that the lower surface of the sealing lid 251$_i$, which is provided at a position near the upper side walls section 235$a_i$, is heated, and condensation can be prevented.

On the other hand, since the linking portion 131$_i$ is only making contact with the upper side of the sealing lid 251$_i$ via the circular edge portion 131$d_i$, the effect of heating is not as much as with respect to the sealing lid 251$_i$. In the same manner, the lower side wall section 233$a_i$ is temperature controlled to the predetermined temperature using a Peltier element having a heating and cooling function, and furthermore, measurements are simultaneously performed. After completion of the measurement, then by means of an instruction by the sealing lid control portion 167, the linking portion 131$_i$ is made to approach using the detaching member 391, and then by upwardly moving the light guide stage 132 by means of the stage Z axis transfer mechanism 35, the sealing lid 251$_i$ is detached from the linking portion and while remaining on the PCR tube 231$_i$, the linking portion is moved and the linking is released.

Figure 22:
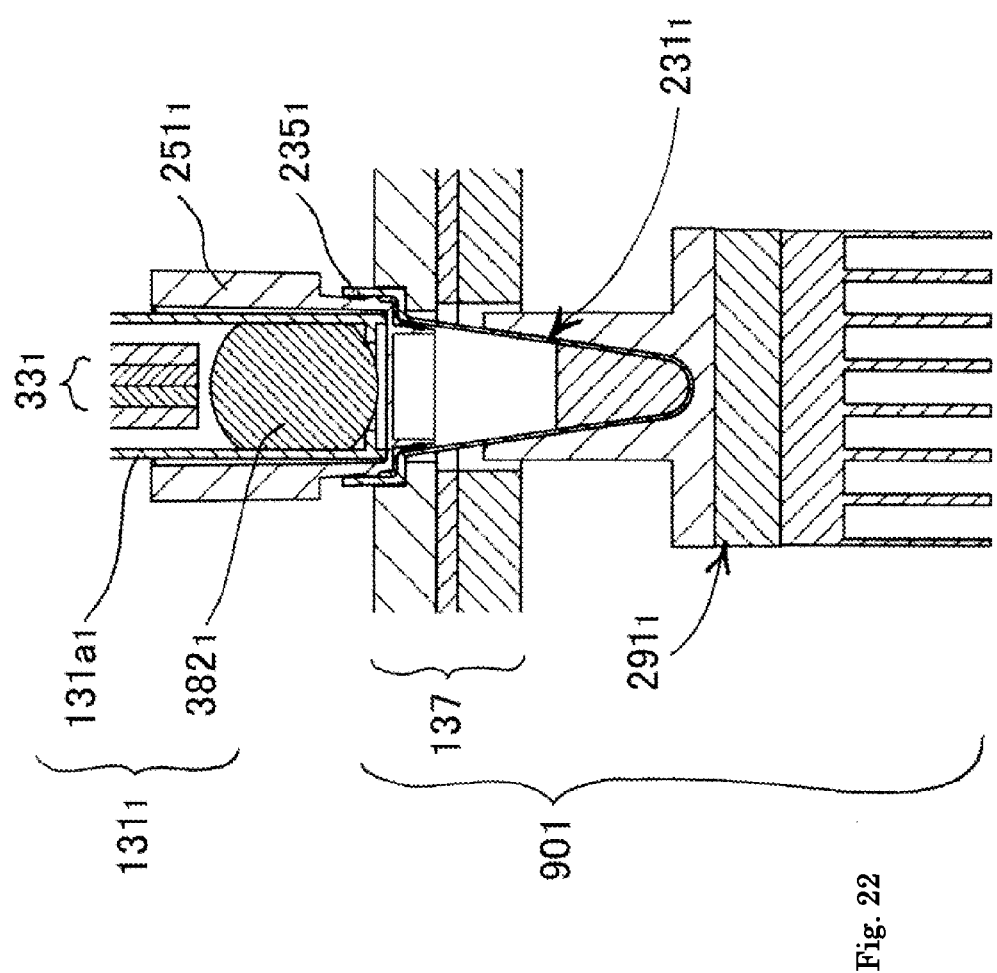
FIG. 22 is a cross-sectional view showing a state in which a linking portion according to a second exemplary embodiment of FIG. 19 is linked with a reaction vessel.

FIG. 22 is a drawing showing a second exemplary embodiment, and represents a linking portion 131$_i$ in which, in place of the ball lens 381$_i$, a drum lens 382$_i$ having a lens diameter corresponding to the inner diameter of the linking cylinder 131$a_i$ is loosely inserted within the linking cylinder 131$a_i$ and mounted on the circular hole 131$b_i$, and is provided such that light is collected at the end of the optical fiber 33$_i$.

Figure 23:
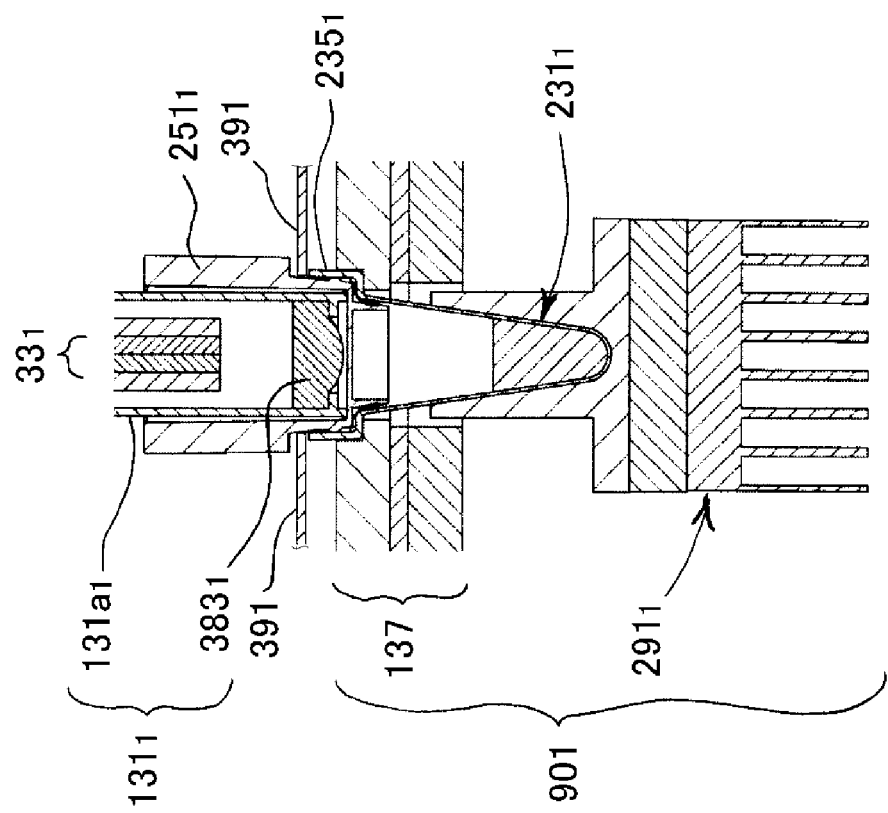
FIG. 23 is a cross-sectional view showing a state in which a linking portion according to a third exemplary embodiment of FIG. 19 is linked with a reaction vessel.

FIG. 23 is a drawing showing a third exemplary embodiment, and represents a linking portion 131$_i$ in which, in place of the ball lens 381$_i$ and the like, an aspheric surface lens 383$_i$ having a lens diameter corresponding to the inner diameter of the linking cylinder 131$a_i$ is loosely inserted within the linking cylinder 131$a_i$ and mounted on the circular hole 131$b_i$, and is provided such that light is collected at the end of the optical fiber 33$_i$. Reference symbol 391 represents a comb-shaped detaching member of the sealing lid detaching mechanism 39, and shown is a state in which it is in the vicinity of, or making contact with, the linking portion 131$_i$. In this state, by raising the linking portion 131$_i$, the sealing lid 251$_i$ engages with the sealing lid detaching member 391 and is detached from the linking portion 131$_i$, but remains still mounted on the PCR tube 231$_i$. Furthermore, the respective lenses 381$_i$ to 383$_i$ may be made to be loosely mounted within the linking cylinder 131$a_i$ by installing a tube-shaped frame from the upper side.

Figure 24:
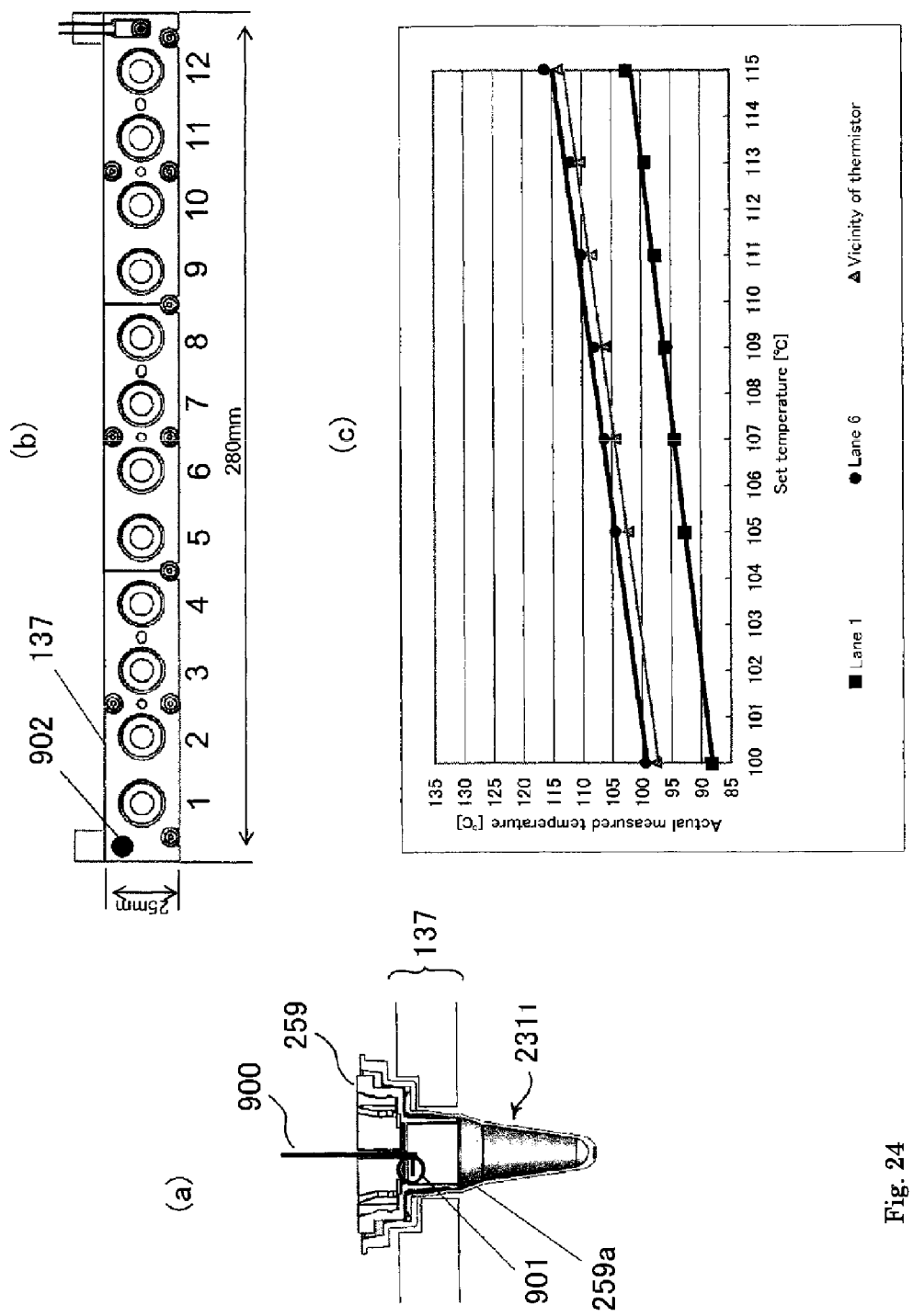
FIG. 24 is a drawing showing heating control according to a fourth exemplary embodiment of FIG. 19.

FIG. 24 is a drawing in which PCR tubes 231$_i$ (FIG. 24A) are housed and retained in twelve through holes 137$d$ provided in a heater 137 (FIG. 24B) according to the present embodiment, with the heater 137 then heated to a predetermined temperature. The top surface temperature of the sealing lid is measured at the time the heating temperature of the heater thereof is increased, and the temperature at which condensation occurs, and the temperature at which condensation is eliminated, are measured.

As shown in FIG. 24A, the apertures of the PCR tubes 231$_i$ are sealed by a sealing lid 259, which has a transparency. The diameter of the upper side of the sealing lid is 14 mm, the height of the mounting portion of the sealing lid 259 is 8.6 mm, and the height from the base of the PCR tube to the upper side of the sealing lid 259 is 21.4 mm. FIG. 24C is a drawing showing the actual measured temperature at the top surface of the sealing lid with respect to the set temperature of the heater.

In step S101, 25 μL of distilled water is dispensed into the narrow-mouthed piping parts of the respective PCR tubes 231$_i$, and as shown in FIG. 24A, the apertures of the wide-mouthed piping parts are sealed by the sealing lid 259, and the PCR tubes 231$_i$ are retained in the twelve through holes of the heater 137. The top surface temperature of the sealing lid 259 is measured by opening a small hole (diameter: 0.5 mm) in the sealing lid 259, inserting a thermocouple 900, and installing it on the inside of the top surface of the sealing lid 259.

In step S102, the temperature of blocks for PCR 292$_i$, which are provided such that the narrow-mouthed piping parts of the PCR tubes 231$_i$ are making contact, are set to 95° C., and the presence of condensation on the top surface of the sealing lid is visually observed. At this time, the set temperature of the heater 137 is gradually raised from 100° C. to 115° C., and the set temperature at which condensation is eliminated is confirmed. Reference symbol 902 represents the position of a thermistor, and a thermocouple is installed in the vicinity thereof.

In a separate experiment, the temperatures were higher, in block division units of the heater 137, in the order of lanes 1 to 4, lanes 9 to 12, and lanes 5 to 8. When the top surface temperature of the sealing lid was measured for lane 1, which had the lowest temperature, and for lane 6, which had the highest temperature, the top surface temperature of the sealing lid of lane 1 was 13° C. lower than the set temperature, and the top surface temperature of the sealing lid of lane 6 was virtually the same as the set temperature. When the set temperature was 113° C., condensation was resolved at all lanes, and it can be inferred that the top surface temperature at lane 1 at this time was approximately 100° C.

Figure 25A:
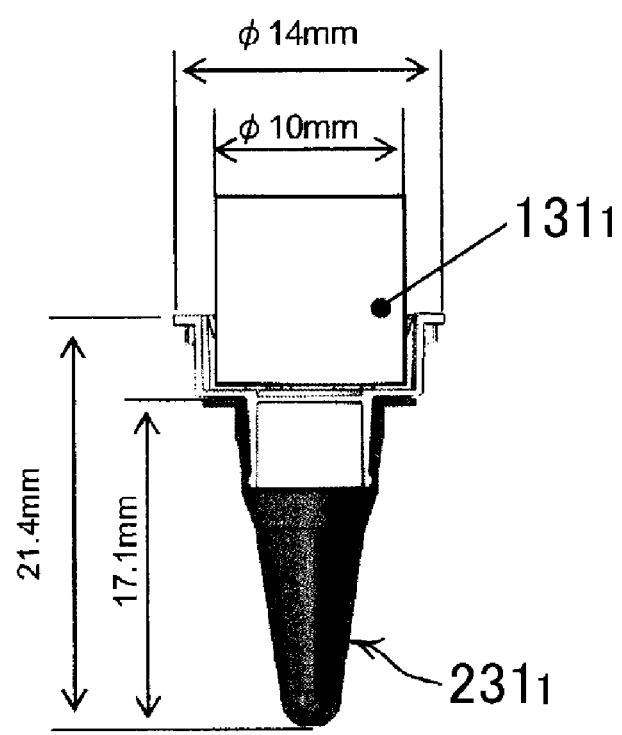
FIGS. 25A, B and C are drawings showing the temperature-fluorescence intensity characteristics within a reaction vessel according to a fifth exemplary embodiment of FIG. 19.
Figure 25B:
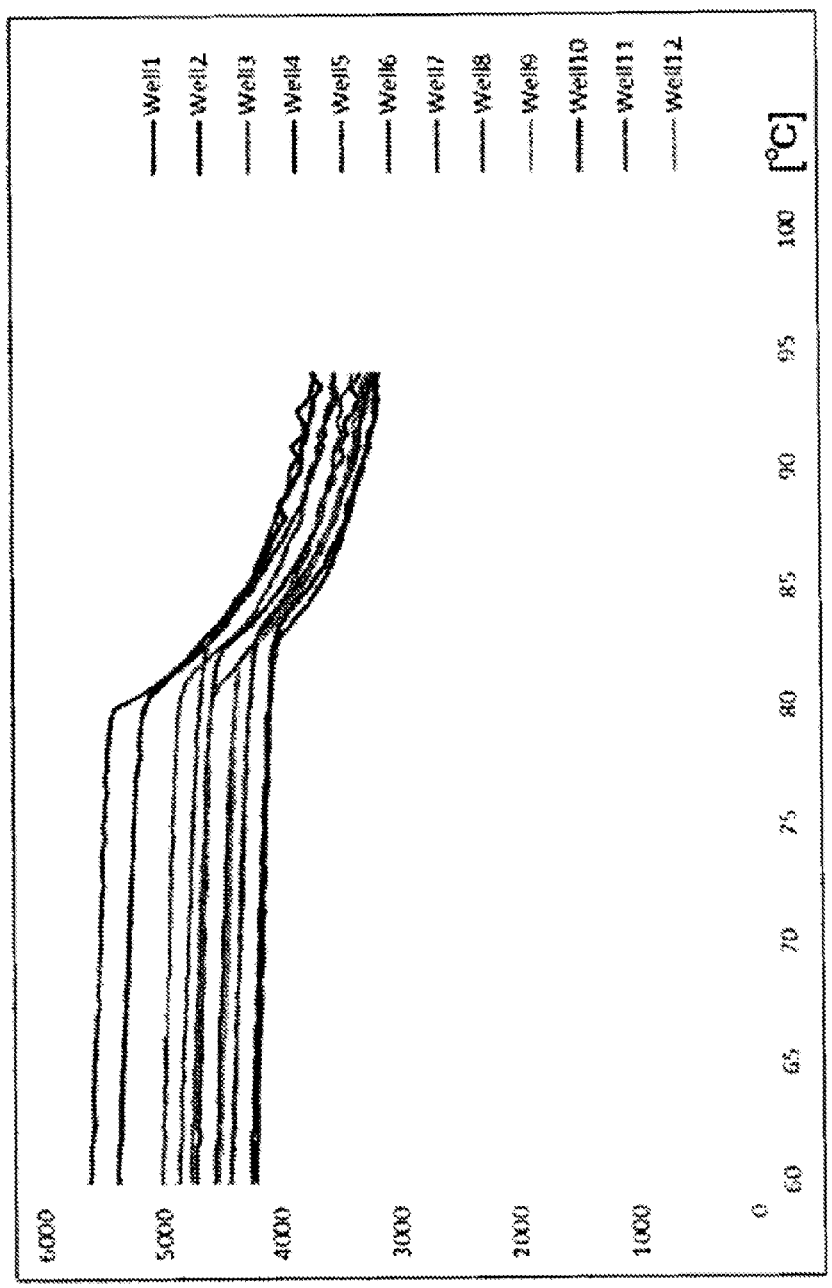
Figure 25C:
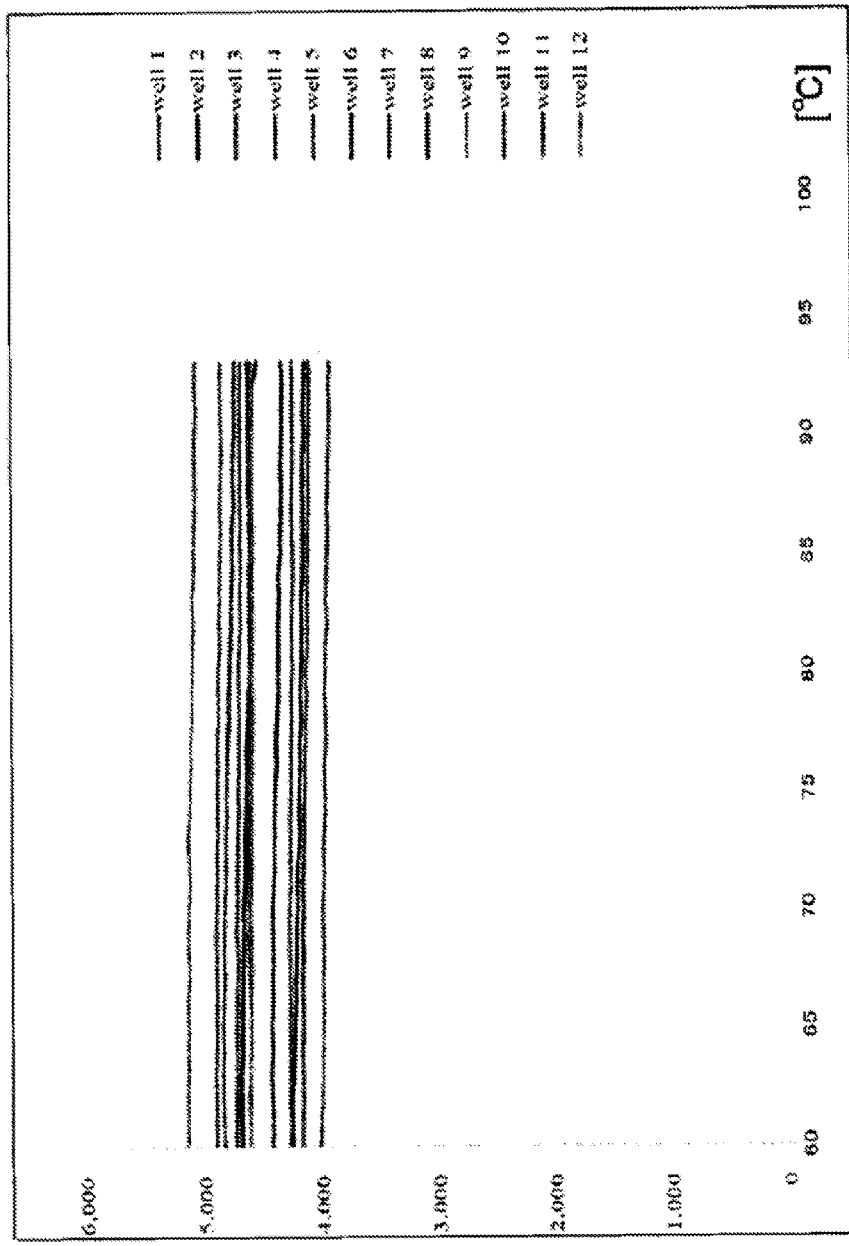

FIGS. 25A, 25B and 25C are drawings showing, when the material of the linking portions 131$_i$ is stainless steel, or when it is a resin with a lower thermal conductivity than stainless steel (PEEK), an improvement to the anti-fogging effect when they are linked with the PCR tubes 231$_i$. FIG. 25A is a drawing showing a PCR tube 231 to which a linking portion 131 is linked. FIGS. 25B and 25C respectively show the temperature-fluorescence intensity characteristics when a stainless steel-made linking portion and a PEEK-made linking portion are used. The vertical axis represents the fluorescence intensity.

In this experiment, in step S201, 20 μL of a fluorescent reagent (0.25 μL ROX) is dispensed into the PCR tubes 231$_i$ representing the reaction vessels, the apertures of which are sealed by the sealing lid 259, and the equivalent of twelve lanes are set to the temperature control block. Then, the linking portion 131 is mounted to the indentation section of the sealing lid. Here, the linking portions 131$_i$ have an outer diameter of 10 mm.

In step S202, the block temperature is raised from 60° C. to 95° C. by means of the temperature control block, and the fluorescence intensity is measured for the respective lanes every 1° C. Consequently, in contrast to a marked decrease in the fluorescence intensity being observed at a PCR block temperature of approximately 80° C. or higher when a stainless steel-made linking portion is used, this is improved when a PEEK-made linking portion is used. Here, in comparison to the thermal conductivity (approximately 16.7 W/(m·K)) of stainless steel (SUS303), the thermal conductivity of PEEK of approximately 0.25 W/(m·K) is very low. Therefore, it is considered that the anti-fogging properties are improved as a result of a decrease in the heat release from the heater 137 that occurs by transmission to the linking portion, and the heating effect toward the sealing lid thereby improving.

Figure 26:
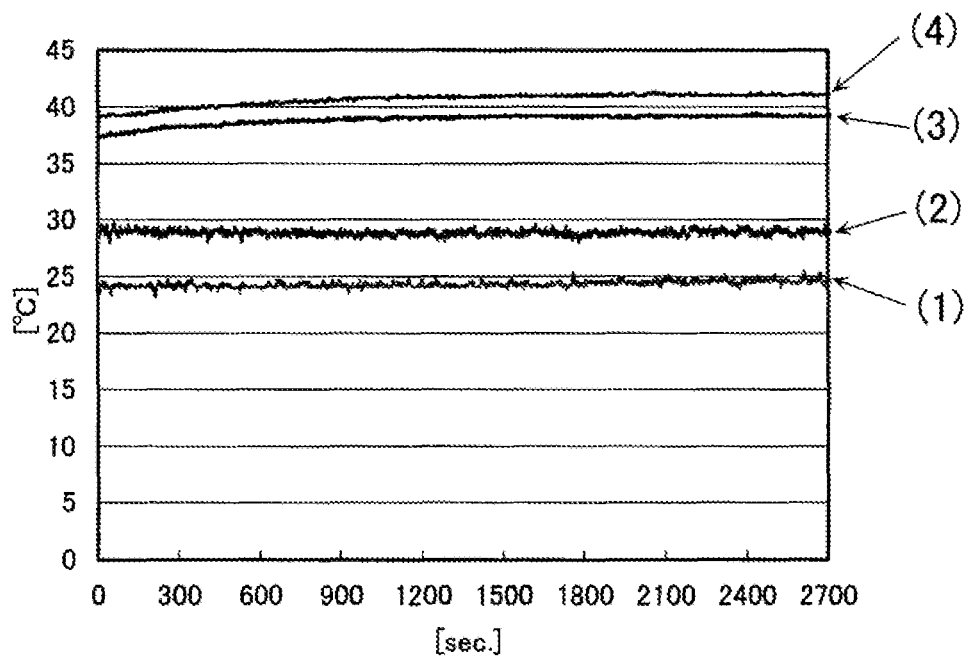
FIG. 26 is a drawing showing temperature measurement results of a ferrule within a linking portion according to a sixth exemplary embodiment of FIG. 19.

FIG. 26 is a drawing showing the thermal effects of heat transfer from the heater 137 imparted on an optical fiber 33 representing the light guide portion, which is provided within the linking portion 131 and surrounded by a ferrule 131c.

In conclusion, the temperature within the ferrule is a maximum of 41° C. at the time of execution of temperature control by a thermal cycle. This is sufficiently lower than the heat resistance temperature of 70° C. of the optical fiber 33 representing the light guide portion, and it is considered that heat transfer from the heater imparts no effects on the degradation of the optical fiber.

The experiment was performed using a thermo-recorder (KEYENCE NR-250(K05003)), an extra fine thermocouple 01-K manufactured by Ninomiya Electric Wire Co., Ltd. as a temperature sensor, and a ferrule (front end outer diameter: 3.5 mm, length: 32.5 mm) not containing a fiber.

The thermocouple was inserted into the ferrule. A Teflon (registered trademark) tube was pressed into the ferrule, and one of the thermocouples was pressed and fixed against the inner wall of the ferrule. Two such ferrules were prepared and installed within the linking portion 131. The linking portions were mounted onto lane 6, which had the highest temperature on the heater 137, and lane 1, which had the lowest temperature. Then, after PCR temperature control to 95° C. (2 min), a thermal cycle that repeats 50 times a cycle from 60° C. (30 sec) to 95° C. (5 sec) was executed, and the temperature change within the ferrule was recorded. The temperature of the heater 137 was set to 113° C., at which condensation was eliminated.

In FIG. 26, (1) represents room temperature, (2) represents the temperature within the apparatus, (3) represents the temperature of lane 1, and (4) represents the temperature of lane 6.

As a result of this experiment, the temperature within the ferrule 131c at completion of the thermal cycle had risen by approximately 2° C. compared to the start. Therefore, the temperature within the ferrule at completion of the thermal cycle was a maximum of approximately 41° C. (steady state). Consequently, this temperature is sufficiently lower than the heat resistance temperature of 70° C. of the optical fibers $33_i$ of the light guide portions, and it is considered that heat transfer from the heater 137 imparts no effects on the degradation of the optical fibers $33_i$ within the linking portions $131_i$.

Figure 27:
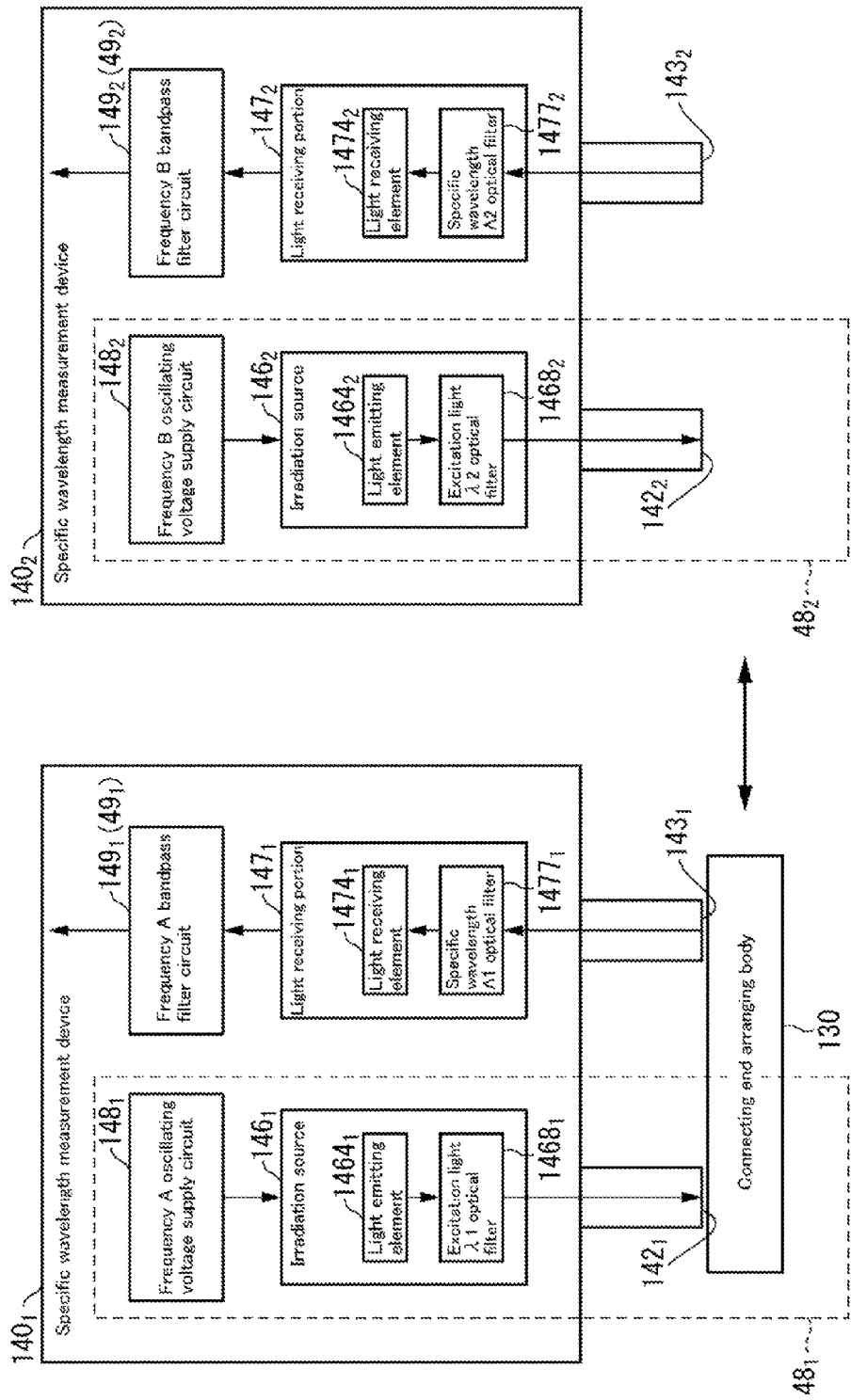
FIG. 27 is a block diagram showing a measurement device of a light measurement apparatus for a reaction vessel according to a third embodiment of the present invention.

FIG. 27 is a drawing showing extracted two adjacent specific wavelength measurement devices $140_1$ and $140_2$ among the six specific wavelength measurement devices $140_j$ (j=1, ..., 6) that correspond to the plurality of types of measurement devices 140 according to a fourth embodiment of the present invention.

The specific wavelength measurement devices $140_1$ and $140_2$ are directly or indirectly linkable with the two or more reaction vessels $231_i$, and are provided corresponding to two or more linking portions $131_i$, to which are provided the front ends of two or more light guide portions $133_i$, which have a flexibility, that optically connect with the interior of the linked reaction vessels $231_i$. The configuration is such that the two or more connecting ends $134_i$, which are provided with the rear ends of the light guide portions that have the front ends provided to the linking portions $131_i$, are provided in the vicinity of, or making contact with, the arranging surface of the connecting end arranging body 130, which maintains them along the predetermined path in a specifiable array, and have one or two or more measuring ends $142_1$ and $143_1$ ($142_2$ and $143_2$) that are successively optically connectable with the respective connecting ends $134_i$ along the predetermined path. They are thus able to receive the light based on the optical state within the reaction vessels by means of an optical connection between the connecting ends $134_j$ and the measuring ends $142_i$ and $143_i$.

There are provided corresponding to the respective specific wavelength measurement devices $140_1$ and $140_2$, at the very least between adjacent specific wavelength measurement devices, modulators $48_1$ and $48_2$ that modulate the intensity of the light of the specific wavelengths Λ1 and Λ2 to be received by the respective specific wavelength measurement devices at the mutually different predetermined frequencies A and B, and tuners $49_1$ and $49_2$ that perform tuning from the received light to the frequency of the light intensity of the modulated specific wavelengths Λ1 and Λ2.

In a case where the light based on the optical state is a fluorescent light, the respective specific wavelength measurement devices $140_1$ and $140_2$ are provided with irradiation sources $146_1$ and $146_2$ that irradiate the predetermined excitation light λ1 and λ2 that excite fluorescent light of the corresponding specific wavelengths or specific wavelength bands Λ1 and Λ2, and light receiving portions $147_1$ and $147_2$ that are able to receive fluorescent light of the specific wavelengths or the specific wavelength bands Λ1 and Λ2. Generally, the wavelength of the excitation light λ is shorter than the specific wavelength Λ.

The irradiation sources $146_1$ and $146_2$ are provided with light emitting elements $1464_1$ and $1464_2$, such as an LED or an incandescent bulb, that emit light containing the corresponding excitation lights λ1 and λ2, and an excitation light λ1 optical filter $1468_1$ and an excitation light λ2 optical filter $1468_2$ that extract and transmit the excitation lights λ1 and λ2 from the emissions of the light emitting elements $1464_1$ and $1464_2$.

The light receiving portions $147_1$ and $147_2$ are provided with a specific wavelength Λ1 optical filter $1477_1$ and a specific wavelength Λ2 optical filter $1477_2$ that extract and transmit light of the corresponding specific wavelengths or the specific wavelength bands Λ1 and Λ2, and light receiving elements $1474_1$ and $1474_2$, such as a photodiode, a phototransistor, a photomultiplier tube, a photoelectric cell, or a photoconductive cell, which convert the light transmitted by the specific wavelength Λ1 optical filter $1477_1$ and the specific wavelength Λ2 optical filter $1477_2$ into a corresponding electrical signal.

Consequently, the modulators $48_1$ and $48_2$ have a frequency A oscillating voltage supply circuit $148_1$ and a frequency B oscillating voltage supply circuit $148_2$ representing the excitation light modulation portions, which supply to the irradiation sources $146_1$ and $146_2$ voltages that oscillate with a predetermined waveform at mutually different predetermined frequencies A and B, which are voltages for driving the light emitting elements of the irradiation sources $146_1$ and $146_2$. The modulators $48_1$ and $48_2$ also include the irradiation sources $146_1$ and $146_2$, and in addition, the reaction vessels $231_i$ in which the fluorescent compound is housed.

On the other hand, the tuners $49_1$ and $49_2$ tune the electrical signals converted from the light received by the light receiving portions $147_1$ and $147_2$ to the frequency A or the frequency B by passing them through a frequency A bandpass filter circuit or a frequency B bandpass filter circuit. Then, of the fluorescent light emitted based on the excitation lights λ1 and λ2 from the specific wavelength measurement devices $140_1$ and $140_2$, the light intensity data (electrical signals) for the frequency A or the frequency B that is received is extracted, which prevents crosstalk between adjacent specific wavelength measurement devices $140_1$ and $140_2$, and measurements with a high reliability can be performed.

Figure 28:
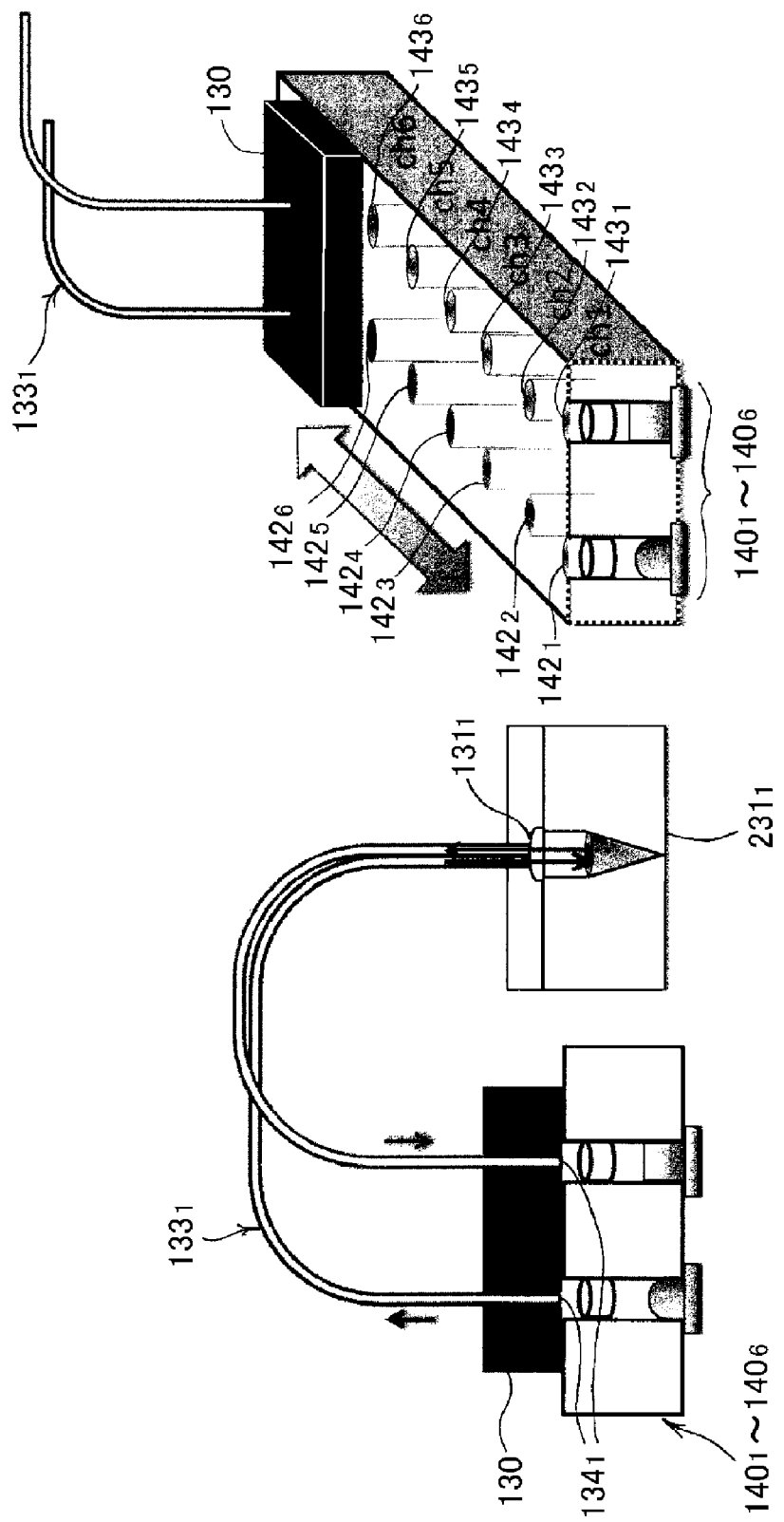
FIG. 28 is a drawing showing connection between the connecting end arranging body and a measuring end according to a first exemplary embodiment of FIG. 27.

FIG. 28, which corresponds to FIG. 27, shows the movement direction between six pairs of measuring ends $142_j$ and $143_j$ of the plurality of types (six types in this example) of specific wavelength measurement devices $140_j$ (j=1, . . . 6), and the connecting ends $134_i$ of the connecting end arranging body 130.

In FIGS. 29A, 29B, 29C, 29D, and 29E the respective modulators corresponding to the six pairs of specific wavelength measurement devices $140_j$ (j=1, . . . 6) shown in FIG. 28 are set to the respective frequencies A to F (A, B, C, D, E, F)=(1 kHz, 4 kHz, 7 kHz, 4 kHz, 1 kHz). In a case where the intensity of the excitation light is modulated as a blinking signal, a non-reflective sheet housed within the reaction vessels is irradiated instead of a sample, and data that is tuned to the respective frequencies from the electrical signal of the light received at a sampling rate of 5 ms is extracted. Then, the crosstalk between the specific wavelength measurement devices $140_j$ was measured by measuring the intensity (data that corresponds to intensity data of the received fluorescent light) of the corresponding excitation light. Here, the intensity of the excitation light is overwhelmingly higher (on the order of several hundred times) than the intensity of the fluorescent light. Furthermore, the wavelength of the excitation light is short compared to the wavelength of the fluorescent light that is excited. However, if several types of fluorescent light are used, there are cases where the wavelength or the wavelength band of the excitation light overlaps with the wavelength or the wavelength band of the fluorescent light used in an adjacent measurement device that does not support the excitation light thereof. In such a case, there is a concern of the excitation light not being able to be excluded at the time the fluorescent light is received, generating crosstalk between the measurement devices.

Figure 29A:
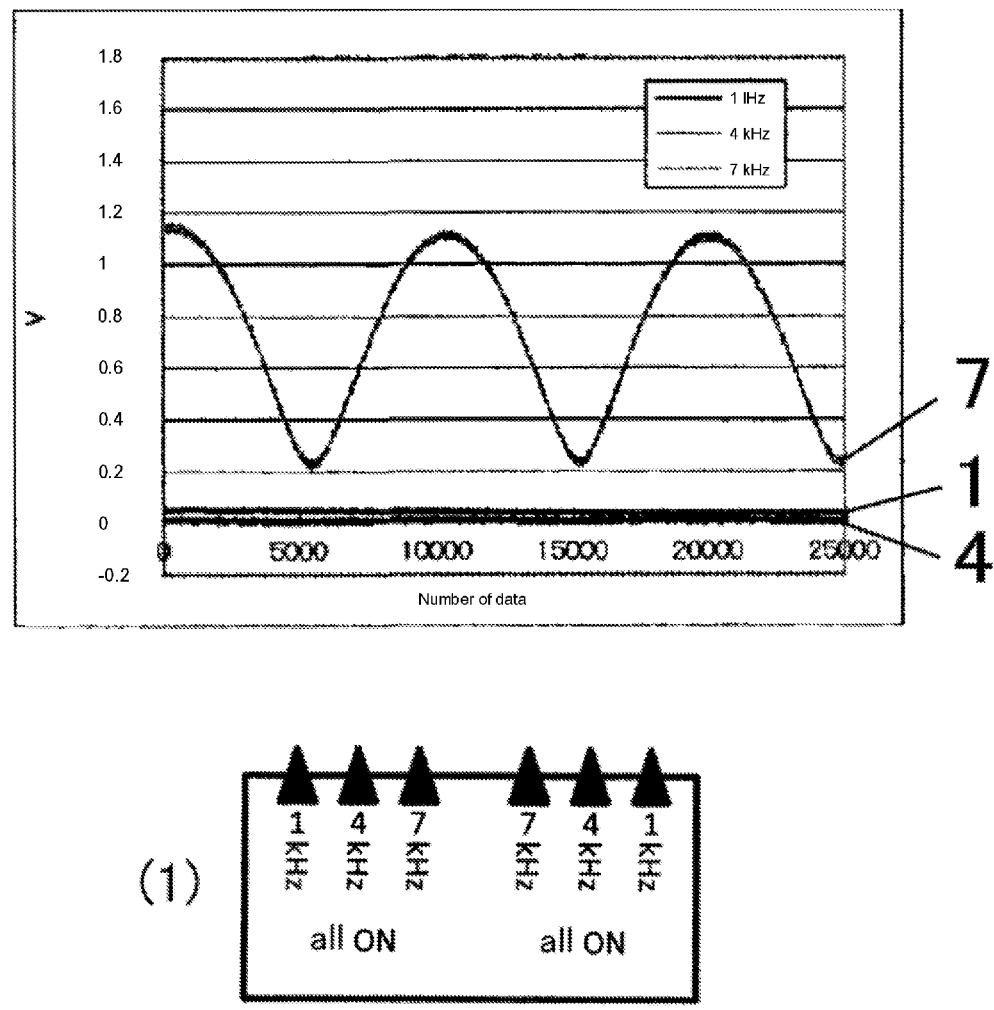
FIGS. 29A, B, C, D, and E are drawings showing the effects between measurement devices with regard to the light to be received by the measurement devices of FIG. 27.

In the case of FIG. 29A (1), only the specific wavelength measurement devices $140_1$, $140_2$, and $140_3$ provided on the substrate 1 are set with mutually different frequencies A, B, and C (=1 kHz, 4 kHz, 7 kHz), and for the case where the respective excitation lights λ1, λ2, and λ3 are irradiated, there is shown the intensities of the excitation lights received by the respective measurement devices as a result of leaks, scattering, reflection, and the like. In this case, as shown in the graph of (1), light of a constant intensity is respectively obtained. Therefore, crosstalk from the respective adjacent specific wavelength measurement devices was not observed.

Figure 29B:
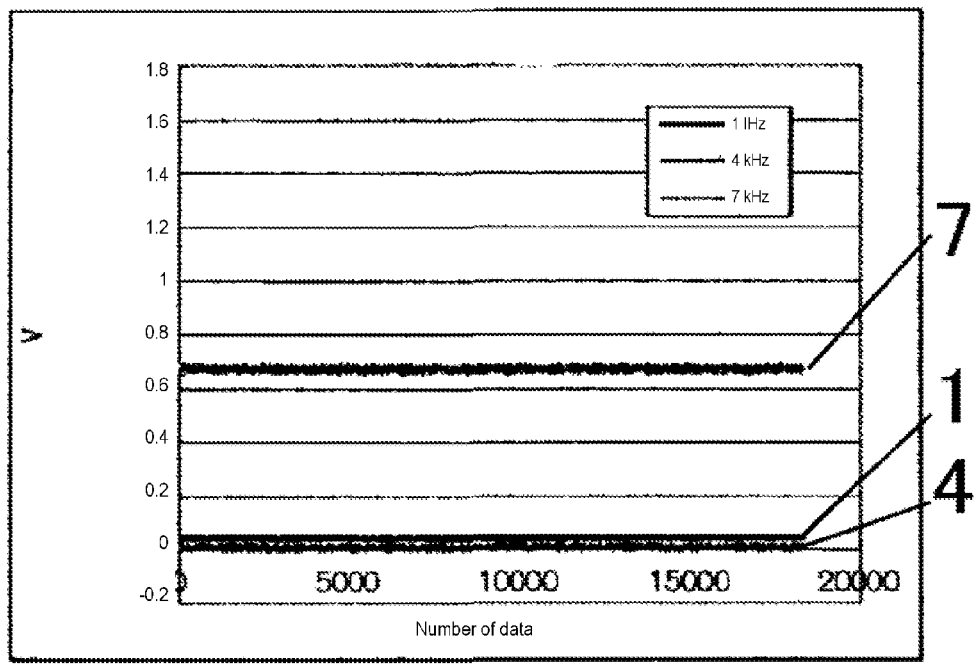
Figure 29B:
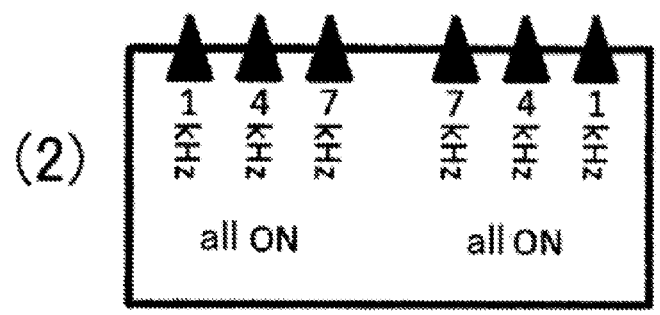

In the case of FIG. 29B (2), all of the specific wavelength measurement devices $140_1$, $140_2$, and $140_3$ provided on the substrate 1 and $140_4$, $140_5$, and $140_6$ provided on the substrate 2 are set with the frequencies A to F as described above. Then, the respective excitation lights λ1, λ2, and λ3 are irradiated, and shown are the intensities of the excitation lights measured at the specific wavelength measurement devices $140_1$, $140_2$, and $140_3$ provided on the substrate 1. In this case, as shown in the graph of (2), the specific wavelength measurement device $140_3$ is such that crosstalk of the excitation light exists with the adjacent specific wavelength measurement device $140_4$ due to the excitation light being modulated at the same frequency of 7 kHz, and it is observed that there is a fluctuation in the intensity resulting from a combination of an offset in the phases of the modulated waveforms (blinking type) of the two devices.

Figure 29C:
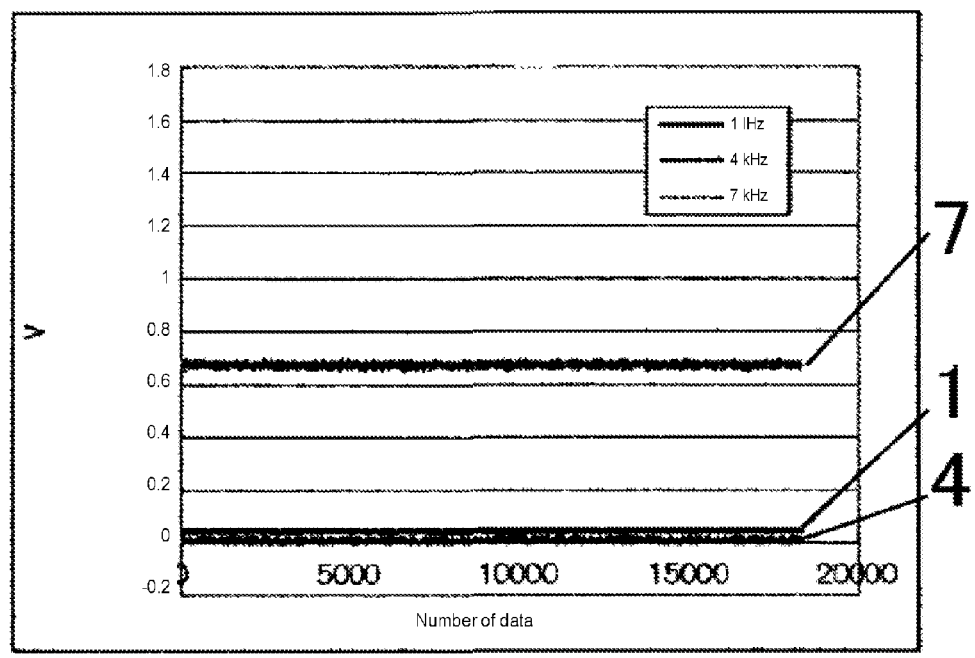
Figure 29C:
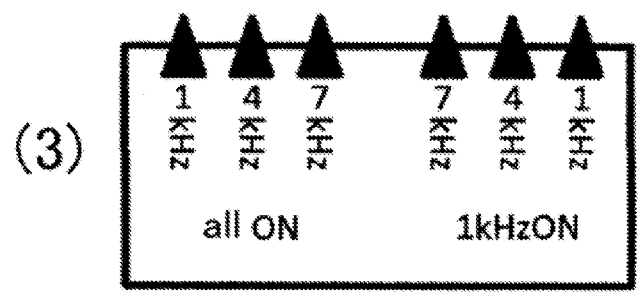

In the case of FIG. 29C (3), shown is a case where all of the specific wavelength measurement devices $140_1$, $140_2$, and $140_3$ provided on the substrate 1, and only the specific wavelength measurement device $140_6$ provided on the substrate 2 are driven, and a measurement is performed at the specific wavelength measurement devices provided on the substrate 1. As shown in the graph of (3), crosstalk of the excitation light is not observed since the spacing between measurement devices having the same frequency is long.

Figure 29D:
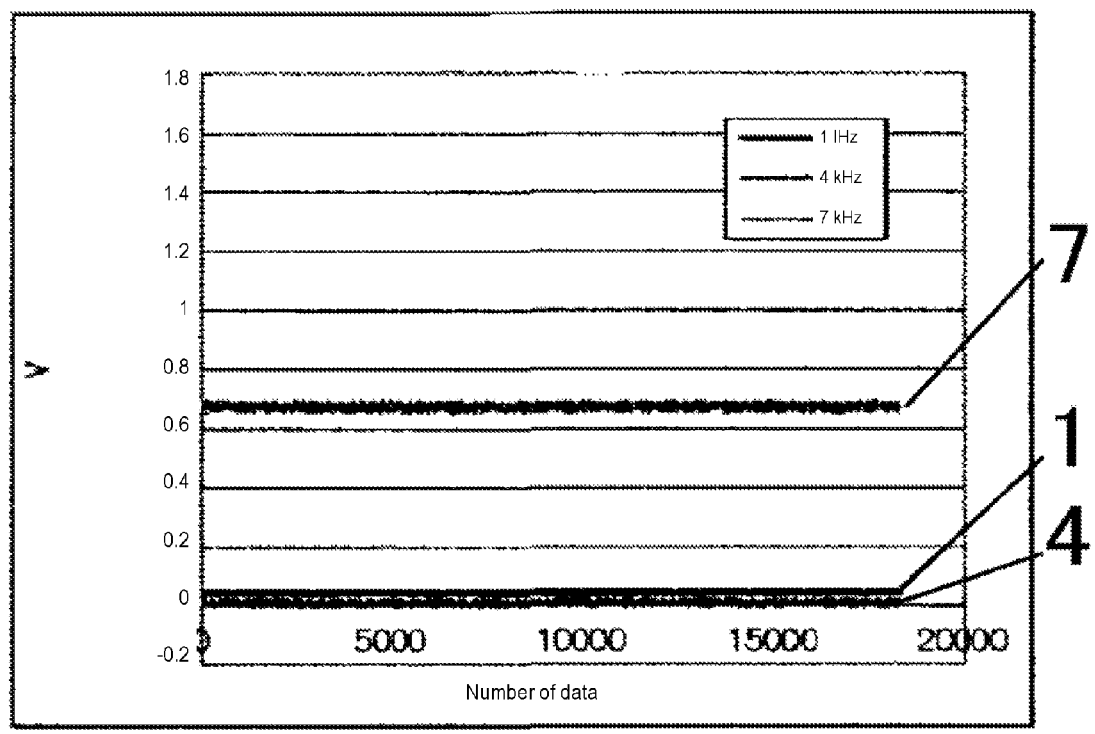
Figure 29D:
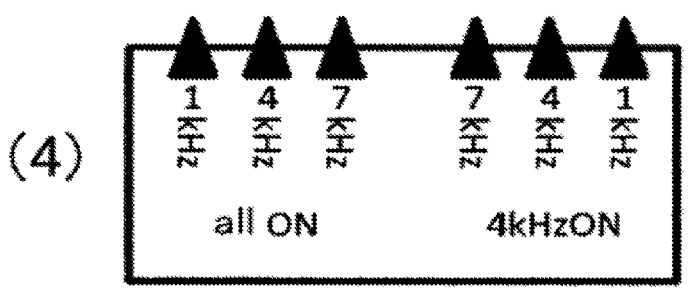

In the case of FIG. 29D (4), shown is a case where all of the specific wavelength measurement devices $140_1$, $140_2$, and $140_3$ provided on the substrate 1, and only the specific wavelength measurement device $140_5$ provided on the substrate 2 are driven, and a measurement is performed at the specific wavelength measurement devices provided on the substrate 1. As shown in the graph of (4), crosstalk of the excitation light is not observed.

Figure 29E:
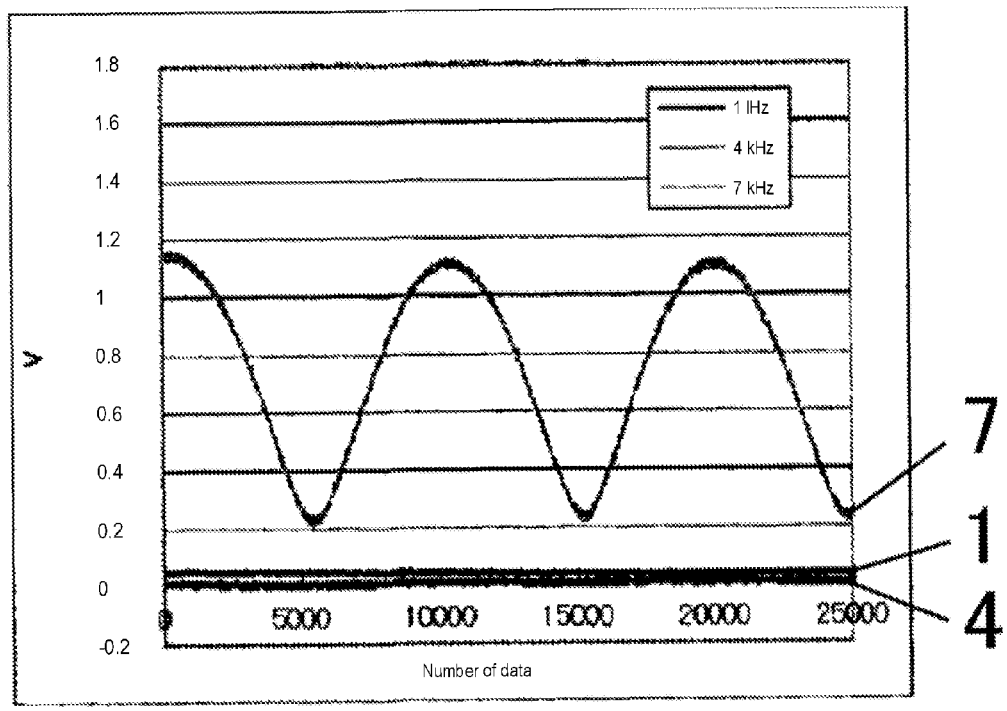
Figure 29E:
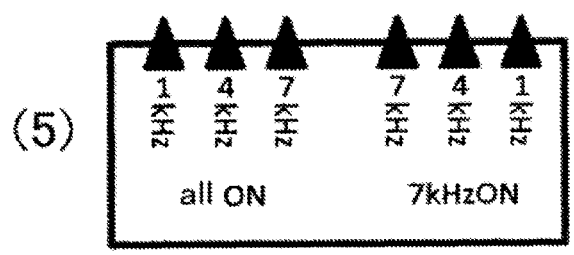

In the case of FIG. 29E (5), shown is a case where all of the specific wavelength measurement devices $140_1$, $140_2$, and $140_3$ provided on the substrate 1, and only the specific wavelength measurement device $140_4$ provided on the substrate 2 are driven, and a measurement is performed at the specific wavelength measurement devices provided on the substrate 1. As shown in the graph of (5), the specific wavelength measurement device $140_3$ is such that crosstalk of the excitation light exists with the adjacent specific wavelength measurement device $140_4$ due to the excitation light being modulated at the same frequency of 7 kHz, and it is observed that there is a fluctuation in the intensity resulting from a combination of an offset in the phases of the modulated waveforms of the two devices.

Figure 30:
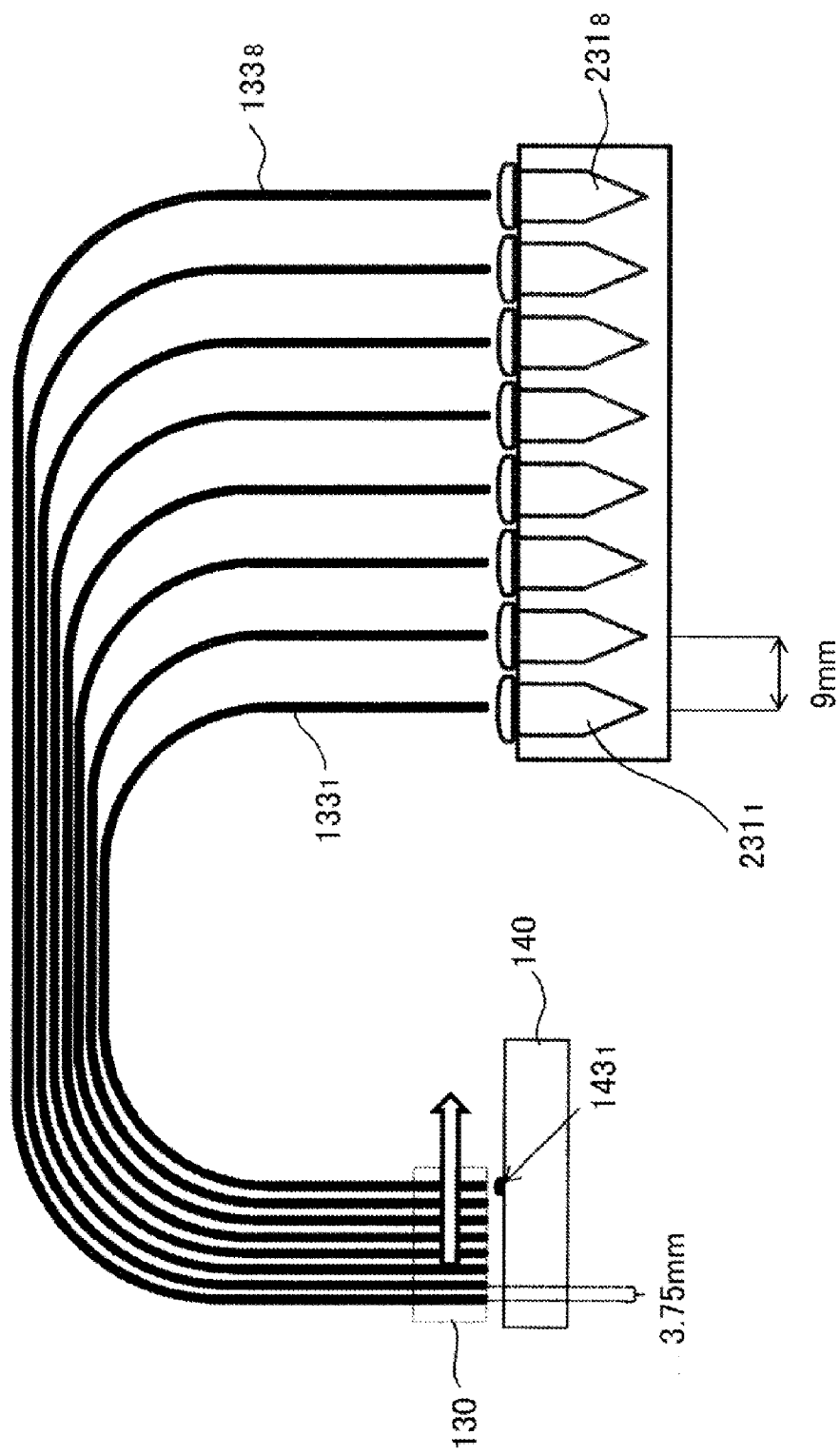
FIG. 30 is a drawing showing the spacing of the linking portions and the spacing of the connecting ends of the connecting end arranging body of FIG. 27.
Figure 31:
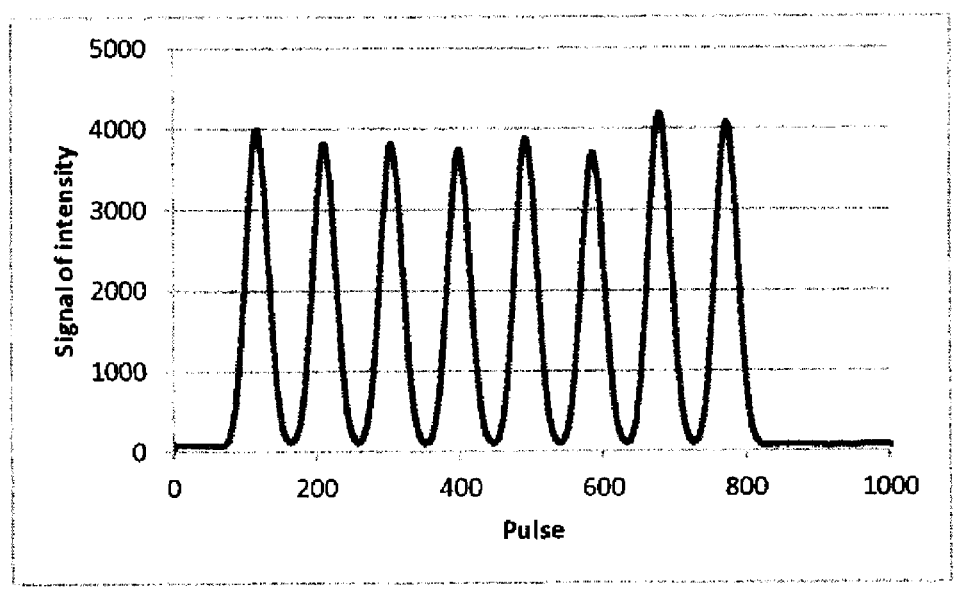
FIG. 31 is a drawing showing a measurement possibility of a measurement device for the case of FIG. 30.

In FIG. 30, shown is a case where, in accordance with 96-well microplates that are utilized as an international standard, the linking portions 131 are arranged with a 9 mm pitch corresponding to the pitch of 9 mm when the PCR tubes 231, representing the reaction vessels are arranged, and the spacing of the connecting ends $134_i$ on the arranging surface of the connecting end arranging body 130 is integrated to 3.75 mm when the diameter of the optical fiber 133, which represents the light guide portion, that is arranged on the connecting end arranging body 130 with one end thereof provided to the linking portion 131, and the other end to the connecting end 134, is 1.5 mm. Even with such a spacing, as shown in FIG. 31, the data of the light received by the measuring end $143_1$ of a given specific wavelength measurement device $140_1$ of the measurement device 140 identifies with certainty the light from the eight connecting ends.

Figure 32:
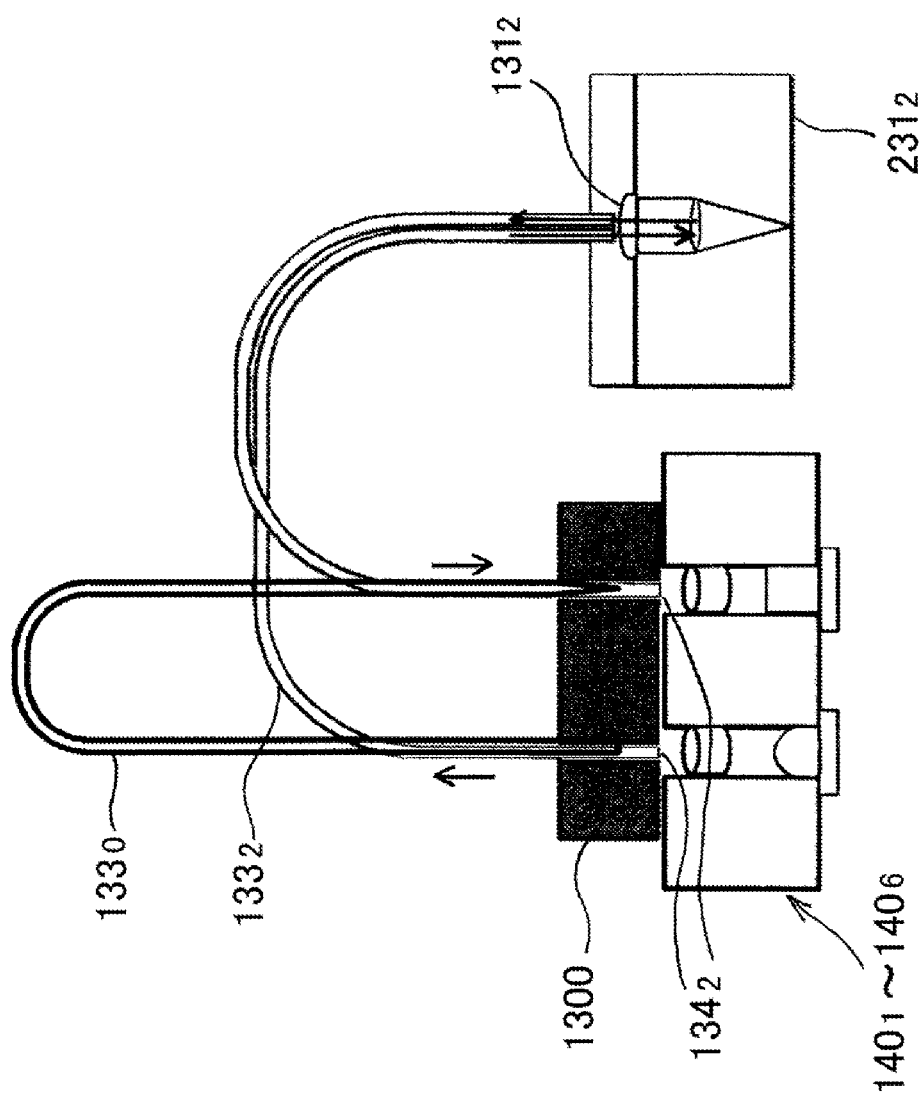
FIG. 32 is a drawing showing connection between the connecting end arranging body and a measuring end according to a seventh embodiment of the present invention.

FIG. 32 is a drawing showing a connecting end arranging body 1300 according to a fourth embodiment of the present invention, and the movement thereof The respective linking portions $131_2$ to $131_{12}$ are provided with the front ends of light guide portion bundles $133_2$ to $133_{12}$ comprising a plurality of light guide portions. Among the light guide portion bundles, a portion of the rear ends of the light guide portion bundles is provided to a first connecting end of the connecting end arranging body 1300, and the remaining light guide portion bundles are provided to a second connecting end of the connecting end arranging body 1300. The predetermined path comprises a linear first path and a linear second linear path for example. The connecting end arranging body is such that, with regard to the eleven pairs of first connecting ends and second connecting ends that are optically connected with the eleven linking portions $131_2$ to $131_{12}$, and a single pair of third connecting ends and fourth connecting ends that are optically mutually connected by means of a light guide portion $133_0$, the eleven first connecting ends and the single third connecting end are arranged along the linear first path, and the eleven second connecting ends and the single fourth connecting end are arranged along the linear second path, which is parallel to the first path leaving a predetermined spacing. In this example, for simplicity, the connecting end arranging body 1300 of the present embodiment has been achieved by removing the light guide bundle $133_1$ provided to the first pair of the first connecting end and the second connecting end of the connecting end arranging body 130 according to the embodiment described above, and further replacing it with the light guide portion $133_0$ that optically mutually connects between the third connecting end and the fourth connecting end.

As a result of movement of the connecting end arranging body 1300, the first measuring ends $140_1$ respectively provided to the measurement devices $140_1$ to $140_6$ relatively move along the first path comprising the eleven first connecting ends and the single third connecting end, and the second measuring ends respectively provided to the measurement devices $140_1$ to $140_6$ relatively move along the second path comprising the eleven second connecting ends and the single fourth connecting ends, respectively. The first measuring ends are optically connected with the irradiation source of the measurement device, and the second measuring ends are connected with the light receiving portion of the measurement device. In contrast to a device in which the pairs of first measuring ends and second measuring ends respectively provided to the measurement devices $140_1$ to $140_6$ are integrally provided, as a result of movement of the connecting end arranging body 1300, for each pair, the first measuring ends of the respective measurement devices successively connect with the eleven first connecting ends and the single third connecting end, and at the same time, the second measuring ends of the respective measurement devices successively connect with the corresponding eleven second connecting ends and the single fourth connecting end. Therefore, together with measurements of the fluorescence intensity by the eleven pairs of first connecting ends and second connecting ends, it becomes possible, by means of the single pair of the third connecting end and the fourth connecting end, for the light receiving portion to directly receive the excitation light via the light guide portion $133_0$ without it being diverted to the reaction vessels, and a genuine excitation light intensity can be measured.

Figure 33:
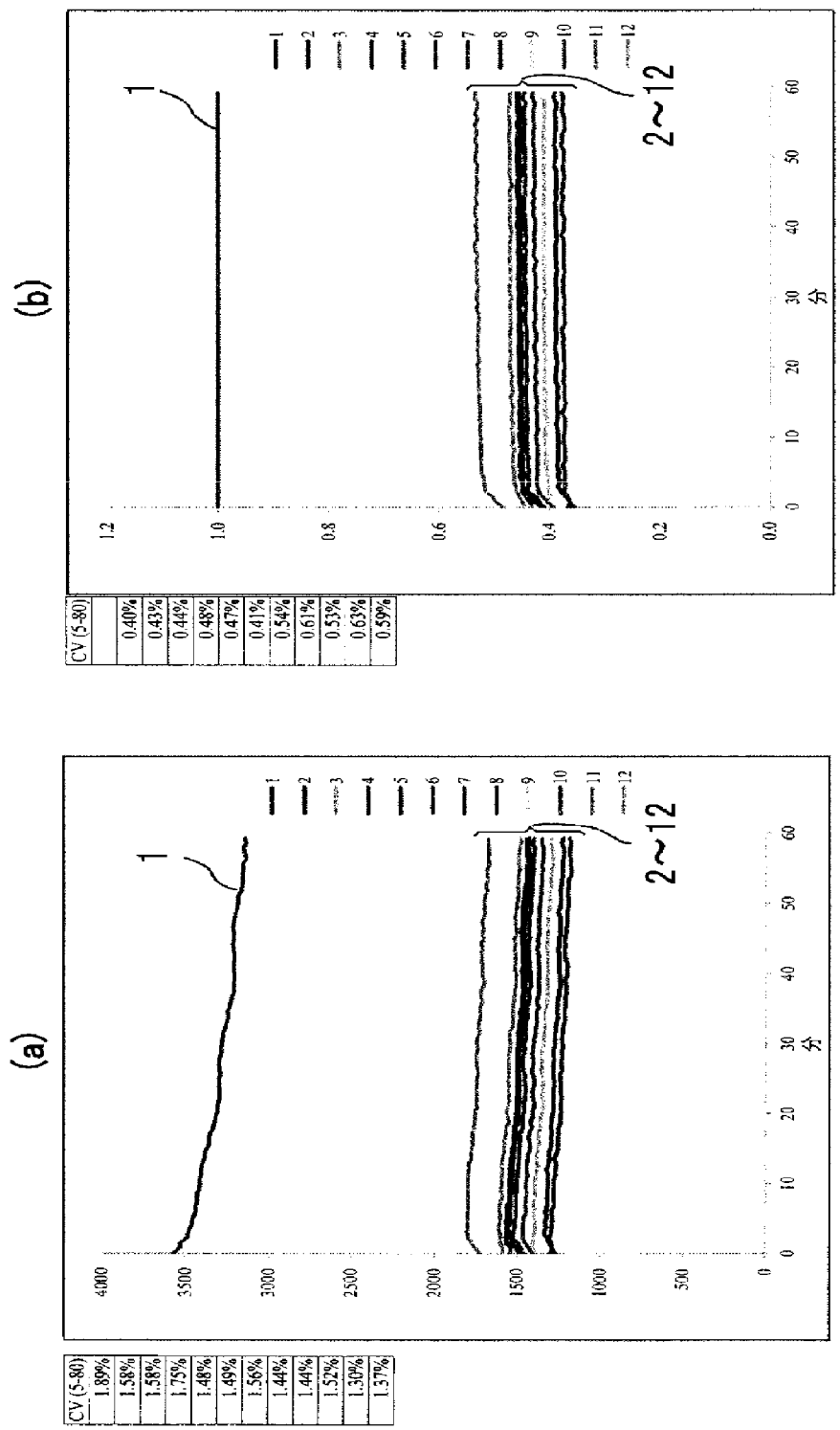
FIG. 33 is a graph showing fluorescence intensities within the reaction vessels using the connecting end arranging body according to FIG. 32, and the standardized fluorescence intensities.

FIG. 33A is a graph plotting, in a case where the temperature of the surroundings of the LED has been intentionally raised (by stopping the cooling fan for example), the intensity of excitation light measured by the light receiving portion using the pair of the third connecting end and the fourth connecting end, and data measured for the intensity of fluorescent light obtained from the respective reaction vessels by irradiating excitation light using the eleven pairs of first connecting ends and second connecting ends with respect to the reaction vessels via the linking portions $131_2$ to $131_{12}$. In the case of this example, the center wavelength of the LED is 590 nm, and a modulated frequency of 7 kHz is added to the excitation light of the LED circuit. Furthermore, distilled water is housed in the respective tubes, and after heating for 5 min at 95° C., a temperature control of 95° C. for 5 sec and 60° C. for 30 sec is repeated for 80 cycles. FIG. 33B is a graph plotting the fluorescence intensities, which have been normalized by removing a fluctuating component of the excitation light by dividing the fluorescence intensity by the measured intensity of the excitation light.

As shown in FIG. 33A, together with the temperature increase of the LED, the intensity of the excitation light measured by the receiving portion using the single pair of the third connecting end and the fourth connecting end is gradually becoming weaker. Consequently, in that case, the nature of the fluctuations in the intensity of the excitation light and the respective fluorescent light from 5 min to 80 min after stabilization of the intensity is expressed as approximately 1.89% to 1.37% as a CV value, in which the standard deviation is divided by the average value. In contrast, as shown in FIG. 33B, looking at the value of the intensity of the fluorescent light divided by the intensity of the excitation light measured using the single pair of the third connecting end and the fourth connecting end, the nature of the fluctuations in the intensity of the fluorescent light shows approximately 0.40% to 0.63% as a CV value. Therefore, the fluctuations in the fluorescence intensity are small. That is to say, it shows that fluorescence intensities that have excitation light fluctuations removed, which are mainly determined by the fluorescent material concentration, are obtained.

Figure 34:
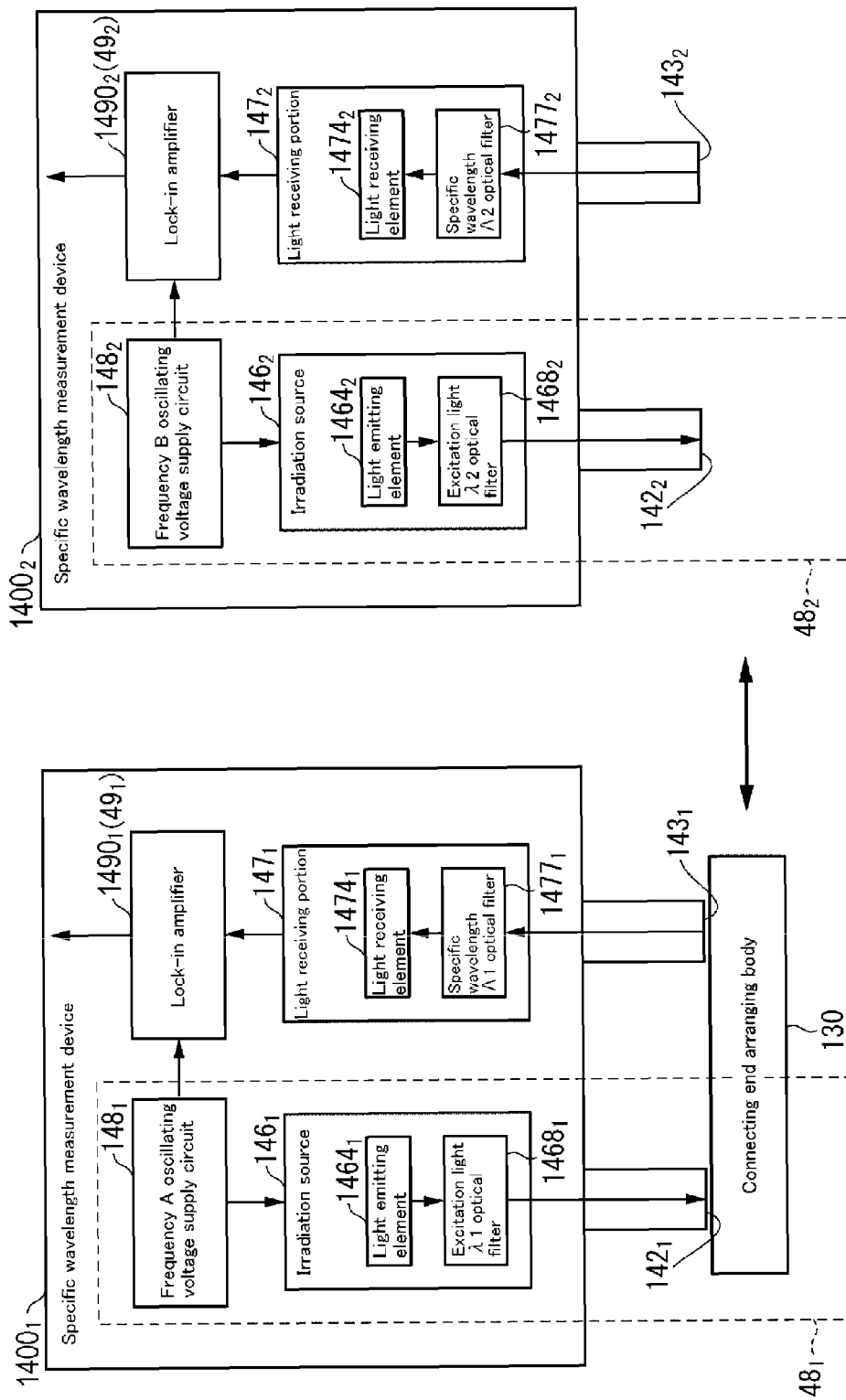
FIG. 34 is a block diagram showing a measurement device of a light measurement apparatus for a reaction vessel according to an eighth embodiment of the present invention.

FIG. 34 shows specific wavelength measurement devices $1400_1$ and $1400_2$ in a case where, as tuners $49_1$ and $49_2$, lock-in amplifiers $1490_1$ and $1490_2$ are used instead of bandpass filter circuits. In this case, the reference signal can utilize the outputs of the frequency A and B oscillating voltage supply circuits $148_1$ and $148_2$ of the modulators $48_1$ and $48_2$. Therefore, the configuration is simplified as a whole, and measurements with a high reliability can be performed.

The foregoing exemplary embodiments have been specifically described in order to better understand the present invention, and they are in no way limiting of other embodiments. Therefore, modifications are possible within a scope that does not depart from the gist of the invention. The configurations, shapes, materials, arrangements, numbers, and amounts of the nozzles, the dispensing tips, the punching tips, the vessel group, the exclusive regions thereof, the housing parts, the measuring ends, the measurement devices, the specific wavelength measurement devices, the suction-discharge mechanism, the transfer mechanism portion, the magnetic force part, the heating portion, the reaction vessels, the sealing lids, the light guide stage, the linking portions, the light guide portions, the connecting ends, the connecting end arranging body, the linking portion arranging body, the nozzle head, the temperature controller, the nozzle detaching mechanism, the sealing lid detaching mechanism, the modulators, the tuners, and the like, and the utilized reagents and samples are also in no way limited by the examples illustrated in the exemplary embodiments. Furthermore, although the nozzles were made to move with respect to the vessel group, it is possible to also move the vessel group with respect to the nozzles.

Furthermore, in the foregoing descriptions, although the amplification solution was sealed using a sealing lid for the sealing of the reaction vessel for PCR, it may be made such that, in its place or in combination, it is sealed using a sealing liquid, such as mineral oil. Furthermore, in place of punching by mounting a tip for punching on the nozzles, it is possible to use a punching pin that is driven by the suction-discharge mechanism. Moreover, although a real-time PCR measurement was described in the foregoing descriptions, it is in no way limited to this measurement, and it can be applied to other various measurements in which temperature control is performed. In the foregoing descriptions, although a case where the measurement device is provided to a dispensing device was described, it is not necessarily limited to this. Although only an optical system using optical fibers was described, it is possible to also employ an optical system using a lens system in the interior of the measurement device.

Furthermore, the apparatuses described in the respective exemplary embodiments of the present invention, the components that form these apparatuses, or the components that form these components, can be appropriately selected, and can be mutually combined by applying appropriate modifications. The spatial representations within the present application, such as "above", "below", "interior", "exterior", "X axis", "Y axis", and "Z axis" are for illustration only, and are in no way limiting of the specific spatial directions or arrangements of the construction.

INDUSTRIAL APPLICABILITY

The present invention is related to fields in which the processing, testing, and analysis of nucleic acids, which primarily includes DNA, RNA, mRNA, rRNA, and tRNA for example, is required, and is related to industrial fields, agricultural fields such as food, agricultural products, and fishery processing, chemical fields, pharmaceutical fields, health care fields such as hygiene, insurance, diseases, and genetics, and scientific fields such as biochemistry or biology for example. The present invention is, in particular, able to be used in processing and analysis that handles various nucleic acids, and the like, such as PCR and real-time PCR.

BRIEF DESCRIPTION OF THE REFERENCE SYMBOLS 10, 110 Light measurement apparatus for reaction vessel
20, 120 Vessel group
$20_i$, $120_i$ (i=1, . . . , 12) Exclusive regions
$211_i$ (i=1, . . . , 12) Dispensing tips
$231_i$, $236_i$ (i=1, . . . , 12) PCR tubes (reaction vessels)
30, 300, 130, 1300 Connecting end arranging body
$31_i$, $131_i$ (i=1, . . . , 12) Linking portions
32, 320, 132 Light guide stage
$33_i$ Optical fibers (example of light guide portions)
40, 400, 140 Measurement device
$40_j$, $400_j$, $1400_j$ (j=1, . . . , 6) Specific wavelength measurement devices
44 Measuring end
$48_j$ Modulator
$49_j$ Tuner
50, 500, 150 Nozzle head
52 Transfer mechanism portion
53 Suction-discharge mechanism
59 Tip detaching mechanism
61, 161 Measurement control portion
70 Nozzle arranging portion
$71_i$ (i=1, . . . , 12) Nozzle

The invention claimed is:

1. A light measurement apparatus for a reaction vessel comprising:
two or more linking portions to which is provided front ends of one or two or more light guide portions that are directly or indirectly linkable with two or more reaction vessels and optically connect with the interior of the reaction vessel to which it is linked;
a connecting end arranging body that has an arranging surface that arranges and supports along a predetermined path, two or more connecting ends, to which is provided back ends of the light guide portions, in which the front ends thereof are provided to the linking portions, the connecting ends are provided corresponding to the respective linking portions;
a measurement device that has one or two or more measuring ends that are successively optically connectable with the respective two or more connecting ends along the predetermined path on the arranging surface, and in which light based on an optical state within the reaction vessels is receivable by means of optical connections between the two or more connecting ends and the measuring ends, the measuring ends are provided approaching or making contact with the arranging surface; and
a light guide switching mechanism that relatively moves the respective two or more connecting ends arranged on the connecting end arranging body and the respective measuring ends along the predetermined path on the arranging surface such that they are successively optically connected, in a state that the two or more linking portions are held to be linked to the respective two or more reaction vessels,
wherein the measurement device comprises a plurality of types of measurement devices each including a photoelectric element, and provided with respect to the respective measurement devices, and at the very least between adjacent measurement devices, are a modulator that modulates the intensity of the light to be received by the photoelectric elements provided in the interior of the respective measurement devices at mutually different predetermined frequencies, and a tuner that, with regard to the light received by the respective measurement devices, performs tuning to the predetermined frequencies, and obtains the corresponding intensity of the received light, such that optical crosstalk mainly due to the entry of excitation light from adjacent measurement devices is prevented.

2. A light measurement apparatus for a reaction vessel according to claim 1, wherein at least a portion of the light guide portion has flexibility.

3. A light measurement apparatus for a reaction vessel according to claim 1, wherein the measurement device comprises a plurality of types of specific wavelength measurement devices that are able to receive the respective light of specific wavelengths or specific wavelength bands, the specific wavelength measurement devices having at least one measuring end that is successively optically connectable with the connecting ends along the predetermined path, and the respective predetermined frequencies of the modulators corresponding to the specific wavelength measurement devices being mutually different, at least between adjacent specific wavelength measurement devices, and in a case where the light based on the optical state is a fluorescent light, the specific wavelength measurement devices are provided with an irradiation source that irradiates a predetermined excitation light that excites the corresponding fluorescent light of a specific wavelength or a specific wavelength band, and a light receiving portion that is able to receive the fluorescent light of the specific wavelength or the specific wavelength band, and the modulators that correspond to the respective specific wavelength measurement devices are provided with an excitation light modulation portion that modulates the predetermined excitation lights at the predetermined frequency, and the tuners are provided with a bandpass filter circuit or a lock-in amplifier that, with respect to the light received by the light receiving portion, extracts the intensity data of the light having the predetermined frequencies.

4. A light measurement apparatus according to claim 1, that has two or more linking portions provided on a light guide stage, and a stage transfer mechanism that relatively moves the light guide stage with respect to the reaction vessels such that the linking portion is simultaneously directly or indirectly linked with the two or more reaction vessels.

5. A light measurement apparatus for a reaction vessel according to claim 1, provided with a temperature controller having a temperature source that is provided making contact with or approaching the lower side wall sections of the reaction vessels, and a heating portion provided such that it is able to make contact with or approach the upper side wall sections of the reaction vessels positioned further on an upper side than the lower side wall sections of the reaction vessels, and that has a heat source that is able to heat the upper side wall sections.

6. A light measurement apparatus for a reaction vessel according to claim 1, wherein a linking portion, which is directly or indirectly linkable with the reaction vessels and is provided with an optical element in the interior, is made from a material that is usable to a temperature higher than the dew point of water vapor, and has a thermal conductivity smaller than 1.0 W/(m·K).

7. A light measurement apparatus for a reaction vessel according to claim 1, wherein front ends of a light guide portion bundle which comprises a plurality of light guide portions, are provided to the respective linking portions, back ends of a light guide portion bundle of a portion of the light guide portion bundle are provided to first connecting ends of the connecting end arranging body, a portion or all of the remainder of the light guide portion bundle is provided to second connecting ends of the connecting end arranging body, the predetermined path comprises a first path and a second path, and the connecting end arranging body has a plurality of pairs of first connecting ends and second connecting ends that are optically connected with the linking portion, and a single pair of a third connecting end and a fourth connecting end that is optically mutually connected by means of the light guide portion, and the first measuring end provided to the measurement device is provided relatively movable along a first path, which comprises a plurality of the first connecting ends and a single third connecting end, and the second measuring end provided to the measurement device is provided relatively movable along a second path, which comprises a plurality of the second connecting ends and a single fourth connecting end, and the first measuring end is optically connect with the irradiation source of the measurement device, and the second measuring end is connected with the light receiving portion of the measurement device, and for each pair, the first measuring end is successively connectable with the plurality of first connecting ends and the single third connecting end, and the second measuring end is successively connectable with the plurality of second connecting ends and the single fourth connecting end.

8. A light measurement apparatus for a reaction vessel comprising:
a nozzle head provided with a suction-discharge mechanism that performs suction and discharge of gases, and one or two or more nozzles that detachably mount dispensing tips in which the suction and the discharge of liquids is possible by means of the suction-discharge mechanism;
a vessel group having at the very least one or two or more liquid housing parts that house reaction solutions used for various reactions, a liquid housing part that houses a magnetic particle suspension in which magnetic particles that are able to capture a target compound are suspended, a liquid housing part that houses a sample, one or two or more liquid housing parts that house a solution for separating and extracting of the target compound, and two or more reaction vessels;
a nozzle head transfer mechanism that makes an interval between the nozzle head and the vessel group relatively movable;
a magnetic force part that is able to adsorb the magnetic particles on an inner wall of dispensing tips mounted on the nozzles;
a light guide stage provided to the nozzle head and having two or more linking portions to which ends of one or two or more light guide portions, which have a flexibility, that are directly or indirectly linkable with the respective reaction vessels and optically connect with the interior of the linked reaction vessels, are provided;
a connecting end arranging body having an arranging surface that arranges and supports along a predetermined path two or more connecting ends, to which back ends of the light guide portions, in which front ends thereof are provided to the linking portions, are provided, the connecting ends are provided corresponding to the respective linking portions;
a measurement device having one or two or more measuring ends that are successively optically connectable with the respective two or more connecting ends along the predetermined path on the arranging surface, that is able to receive light based on an optical state within the reaction vessels by means of optical connections between the two or more connecting ends and the measuring ends, the measuring ends are provided approaching or making contact with the arranging surface; and
a light guide switching mechanism provided along the predetermined path of the connecting end arranging body that relatively moves the respective two or more connecting ends and the respective measuring ends along the predetermined path on the arranging surface such that they become successively optically connected, in a state that the two or more linking portions are held to be linked to the respective two or more reaction vessels,
wherein the measurement device comprises a plurality of types of measurement devices each including a photoelectric element, and the apparatus is configured to at the very least between adjacent measurement devices, modulate the intensity of the light to be received by the photoelectric elements provided in the interior of the respective measurement devices at mutually different predetermined frequencies, tune the light received by the measurement devices to the predetermined frequencies, and obtain the corresponding intensity of the received light, such that optical crosstalk mainly due to the entry of excitation light from adjacent measurement devices is prevented.

9. A light measurement method for a reaction vessel comprising:

moving two or more linking portions provided with an end of one or two or more light guide portions, with respect to two or more reaction vessels;

simultaneously directly or indirectly linking the reaction vessels and the linking portions and optically connecting the interior of the linked reaction vessels and the light guide portions;

performing temperature control within the reaction vessels;

guiding light from the reaction vessels to a connecting end arranging body having an arranging surface that arranges and supports along a predetermined path two or more connecting ends which are directly or indirectly optically linked to two or more reaction vessels, and to which back ends of the light guide portions, in which front ends thereof are provided to the linking portions, are provided, the connecting ends are provided corresponding to the respective linking portions; and successively optically connecting along the predetermined path the one or two or more measuring ends provided to a measurement device, which are provided approaching or in contact with the arranging surface, and the respective two or more connecting ends, in a state that the two or more linking portions are held to be linked to the respective two or more reaction vessels, by relatively moving the connecting end arranging body along the predetermined path on the arranging surface, to thereby make a plurality of types of measurement devices receive light based on an optical state within the reaction vessels, wherein the measurement device comprises a plurality of types of measurement devices each including a photoelectric element, and the method comprises at the very least between adjacent measurement devices, modulating the intensity of the light to be received by the photoelectric elements provided in the interior of the respective measurement devices at mutually different predetermined frequencies, tuning the light received by the measurement devices to the predetermined frequencies, and obtaining the corresponding intensity of the received light, such that optical crosstalk mainly due to the entry of excitation light from adjacent measurement devices is prevented.

10. A light measurement method for a reaction vessel according to claim 9, wherein an optical connection between the reaction vessel and the connecting ends is directly or indirectly linkable with two or more reaction vessels, and back ends of one or two or more light guide portions that optically connect with the interior of the linked reaction vessels, are provided on the connecting ends, and the optical connection is performed by relatively moving a light guide stage on which is provided the two or more linking portions provided with front ends of the light guide portions, with respect to the reaction vessel.

11. A light measurement method for a reaction vessel according to claim 9, wherein the front ends of a light guide portion bundle comprising a plurality of light guide portions are provided to the respective linking portions, the light guide portion bundle is such that the rear ends of a portion of the light guide portion bundle are provided to first connecting ends of the connecting end arranging body, a portion or all of the remaining rear ends of the light guide portion bundle are provided to second ends of the connecting end arranging body, the predetermined path comprises a first path and a second path, the connecting end arranging body has a plurality of pairs of first connecting ends and second connecting ends that are optically connected with the linking portion, and a single pair of a third connecting end and a fourth connecting end that is mutually optically connected by means of the light guide portion, and at the time the first measuring end provided to the measurement device relatively moves along the first path, which comprises a plurality of the first connecting ends and a single third connecting end, and the second measuring end provided to the measurement device relatively moves along the second path, which comprises the plurality of second connecting ends and a single fourth connecting end, the first measuring ends optically connect with the irradiation source of the measurement device, and the second measuring ends connect with the light receiving portion of the measurement device, and for each pair, the first measuring end successively connects with the plurality of first connecting ends and the single third connecting end, and the second measuring end successively connects with the plurality of second connecting ends and the single fourth connecting end.

12. A light measurement method for a reaction vessel according to claim 9, comprising: directly or indirectly linking an aperture of the reaction vessel and the linking portion; and at the time of performing temperature control within the reaction vessels, according to temperature control by a temperature controller, which has a temperature source provided making contact with or approaching lower side wall sections of the reaction vessels, heating upper side wall sections of the reaction vessels, which are positioned further on an upper side than the lower side wall sections, by means of a heat source of a heating portion, which is provided making contact with or approaching the upper side wall sections, and thereby preventing direct or indirect condensation of the linking portions.

13. A light measurement method for a reaction vessel comprising:

detachably mounting dispensing tips on respective nozzles, which are provided to a nozzle head and perform the suction and the discharge of gases;

separating a target compound by using a magnetic force part, a nozzle head transfer mechanism that relatively moves an interval between the nozzle head and a vessel group, a magnetic particle suspension housed within a vessel group, in which magnetic particles that are able to capture a target compound are suspended, a sample, and a solution for separating and extracting of a target compound;

introducing the separated target compound and a reaction solution used for reactions to a plurality of reaction vessels provided to a vessel group;

moving a light guide stage, which has two or more linking portions that are provided to the nozzle head and in which front ends of one or two or more light guide portions are also provided, with respect to the reaction vessels by means of, at the very least, the nozzle head transfer mechanism;

directly or indirectly simultaneously linking the respective reaction vessels and the linking portions, and optically connecting the interior of the reaction vessels and the light guide portions that are linked;

performing temperature control within the reaction vessels;

guiding light from the reaction vessels to a connecting end arranging body that arranges and supports along a predetermined path two or more connecting ends, to which back ends of the light guide portions, in which front ends thereof are provided to the linking portions, are provided, the connecting ends are provided corresponding to the respective linking portions; and successively optically connecting one or two or more measuring ends that are provided to a measurement device, and provided approaching or making contact with an arranging surface, and the respective two or more connecting ends, in a state that the two or more linking portions are held to be linked to the respective two or more reaction vessels, along the predetermined path by moving the connecting end arranging body, to thereby make the measurement device receive the light based on an optical state within the reaction vessels, wherein the measurement device comprises a plurality of types of measurement devices each including a photoelectric element, and the method comprises, at the very least between adjacent measurement devices, modulating the intensity of the light to be received by the photoelectric elements provided in the interior of the respective measurement devices at mutually different predetermined frequencies, tuning the light received by the respective measurement devices to the predetermined frequencies, and obtaining the corresponding intensity of the received light, such that optical crosstalk mainly due to the entry of excitation light from adjacent measurement devices is prevented.

14. A light measurement method for a reaction vessel according to claim 13, wherein the measurement device comprises a plurality of types of measurement devices, and the method comprises at the time of guiding light from the reaction vessels to a connecting end arranging body, at the very least between adjacent measurement devices, modulating the intensity of the light to be received by the measurement devices at mutually different predetermined frequencies, and at the time the measurement device receives the light based on an optical state within the reaction vessels, tuning the light received by the measurement devices to the predetermined frequencies, and obtaining the corresponding intensity of the received light.

* * * * *